(12) United States Patent
Rege et al.

(10) Patent No.: US 11,931,460 B2
(45) Date of Patent: Mar. 19, 2024

(54) AMINOGLYCOSIDE ANTIBIOTIC-DERIVED MICROBEAD-ENCAPSULATED SPHEROIDS AND METHODS OF MAKING AND USING THE SAME

(71) Applicant: Arizona Board of Regents on behalf of Arizona State University, Scottsdale, AZ (US)

(72) Inventors: Kaushal Rege, Chandler, AZ (US); Rajeshwar Nitiyanandan, Tempe, AZ (US); Tanya Nanda, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 119 days.

(21) Appl. No.: 17/529,930

(22) Filed: Nov. 18, 2021

(65) Prior Publication Data

US 2022/0151927 A1 May 19, 2022

Related U.S. Application Data

(60) Provisional application No. 63/115,504, filed on Nov. 18, 2020.

(51) Int. Cl.
| | | |
|---|---|---|
| A61K 35/12 | (2015.01) | |
| A61K 9/127 | (2006.01) | |
| A61K 47/69 | (2017.01) | |

(52) U.S. Cl.
CPC ............ *A61K 9/1273* (2013.01); *A61K 35/12* (2013.01); *A61K 47/6903* (2017.08)

(58) Field of Classification Search
None
See application file for complete search history.

(56) References Cited

U.S. PATENT DOCUMENTS

2018/0021753 A1* 1/2018 Rege ..................... B01J 20/285
528/409

FOREIGN PATENT DOCUMENTS

| CN | 103328626 B | 2/2017 |
|---|---|---|
| JP | 2019517278 | 6/2019 |
| KR | 20190106800 | 9/2019 |

OTHER PUBLICATIONS

Abbot, "Biology's New Dimension." Nature, 424, 870-872 (2003).
Adelöw, C., Segura, T., Hubbell, J. A. & Frey, P. The effect of enzymatically degradable poly(ethylene glycol) hydrogels on smooth muscle cell phenotype. Biomaterials 29, 314- 326 (2008).
Alessandri, K. et al., Cellular capsules as a tool for multicellular spheroid production and for investigating the mechanics of tumor progression in vitro. Proc National Acad Sci 110, 14843-114848 (2013).
Ayala, P., Lopez, J. I. & Desai, T. A. Microtopographical Cues in 3D Attenuate Fibrotic Phenotype and Extracellular Matrix Deposition: Implications for Tissue Regeneration. Tissue Eng Pt A 16, 2519-2527 (2010).
Bhise, N. S. et al. A liver-on-a-chip platform with bioprinted hepatic spheroids. Biofabrication 8, 014101 (2016). 13 pages.
Bissell, M. J., Rizki, A. & Mian, I. S. Tissue architecture: the ultimate regulator of breast epithelial function. Curr Opin Cell Biol 15, 753-762 (2003).
Breslin, S. & O'Driscoll, L. Three-dimensional cell culture: the missing link in drug discovery. Drug Discov Today 18, 240-249 (2013).
Carlsson, J. & Acker, H. Relations between ph, oxygen partial pressure and growth in cultured cell spheroids. Int J Cancer 42, 715-720 (1988).
Cesarz, Z. & Tamama, K. Spheroid Culture of Mesenchymal Stem Cells. Stem Cells Int 2016, 1-11 (2016).
Chan, H. F et al. Rapid formation of multicellular spheroids in double-emulsion droplets with controllable microenvironment. Sci Rep-uk 3, 3462 (2013).
Chan, H. F., Zhang, Y. & Leong, K. W. Efficient One-Step Production of Microencapsulated Hepatocyte Spheroids with Enhanced Functions. Small 12, 2720-2730 (2016).
Chang, T. T. & Hughes-Fulford, M. Monolayer and Spheroid Culture of Human Liver Hepatocellular Carcinoma Cell Line Cells Demonstrate Distinct Global Gene Expression Patterns and Functional Phenotypes. 559-567 (2009).
Choe, G., Park, J., Park, H. & Lee, J. Y. Hydrogel Biomaterials for Stem Cell Microencapsulation. Polymers-basel 10, 997 (2018).
Curcio, E et al. Mass transfer and metabolic reactions in hepatocyte spheroids cultured in rotating wall gas-permeable membrane system. Biomaterials 28, 5487-5497 (2007).
Darling, D. et al. Low-speed centrifugation of retroviral vectors absorbed to a particulate substrate: a highly effective means of enhancing retroviral titre. Gene Ther 7, 914-923 (2000).
Goodwin, T. J., Prewett, T. L., Wolf, D. A. & Spaulding, G. F. Reduced shear stress: A major component in the ability of mammalian tissues to form three-dimensional assemblies in simulated microgravity. J Cell Biochem 51, 301-311 (1993).
Grandhi, T. S. P et al. Aminoglycoside Antibiotic-Derived Anion-Exchange Microbeads for Plasmid DNA Binding and in Situ DNA Capture. Acs Appl Mater Inter 6, 18577-18589 (2014).

(Continued)

*Primary Examiner* — Brian Gulledge
(74) *Attorney, Agent, or Firm* — Riverside Law LLP

(57) ABSTRACT

The instant disclosure is directed to compositions comprising an encapsulated spheroid, and methods of making and using the same. A composition may comprise a spheroid comprising a plurality of cells and aminoglycoside antibiotic-derived hydrogel beads, wherein the spheroid is encapsulated by the aminoglycoside antibiotic-derived hydrogel beads to form an encapsulated spheroid. A method may comprise administering the composition to a subject in need thereof. Another method may comprise administering a compound to the encapsulated spheroid. A method of creating an encapsulated spheroid may comprise coating a surface with an aminoglycoside antibiotic-derived hydrogel, culturing a plurality of cells on the surface, thereby creating a spheroid, and encapsulating the spheroid with a plurality of aminoglycoside antibiotic-derived hydrogel beads.

18 Claims, 40 Drawing Sheets
(20 of 40 Drawing Sheet(s) Filed in Color)

(56) References Cited

OTHER PUBLICATIONS

Grandhi, T. S. P., Potta, T., Nitiyanandan, R., Deshpande, I. & Rege, K. Chemomechanically engineered 3D organotypic platforms of bladder cancer dormancy and reactivation. Biomaterials 142, 171-185 (2017).
Grukienė et al. Quaternization of chitosan and partial destruction of the quaternized derivatives making them suitable for electrospinning. Chemija 24, 325-334 (2013).
Han, H.-W., Asano, S. & Hsu, S. Cellular Spheroids of Mesenchymal Stem Cells and Their Perspectives in Future Healthcare. Appl Sci 9, 627 (2019).
Harrison, R. G. the Developing Nerve. read before the Society for Experimental Biology and Medicine (1907). 13 pages.
Ho, Y. K., Zhou, L. H., Tam, K. C. & Too, H. P. Enhanced non-viral gene delivery by coordinated endosomal release and inhibition of B-tubulin deactylase. Nucleic Acids Res. 45, e38-e38 (2017).
Hsu, et al., Self-assembled adult adipose-derived stem cell spheroids combined with biomaterials promote wound healing in a rat skin repair model. Wound Repair Regen 23, 57-64 (2015).
Hu, G. & Li, D. Three-dimensional modeling of transport of nutrients for multicellular tumor spheroid culture in a microchannel. Biomed Microdevices 9, 315-323 (2007).
Ivascu, A. & Kubbies, M. Rapid Generation of Single-Tumor Spheroids for High-Throughput Cell Function and Toxicity Analysis. J Biomol Screen 11, 922-932 (2006).
J.Bissell, M., C.Radisky, D., Rizki, A., M.Weaver, V. & W.Petersen, O. The organizing principle: microenvironmental influences in the normal and malignant breast. Differentiation 70, 537-546 (2002).
Jacks, T. & Weinberg, R. A. Taking the Study of Cancer Cell Survival to a New Dimension. Cell 111, 923-925 (2002).
Jiang, Y., Pjesivac-Grbovic, J., Cantrell, C. & Freyer, J. P. A Multiscale Model for Avascular Tumor Growth. Biophys J 89, 3884-3894 (2005).
Joshi, P. & Lee, M.-Y. High Content Imaging (HCI) on Miniaturized Three-Dimensional (3D) Cell Cultures. Biosensors 5, 768-790 (2015).
Katsen-Globa, A., Ehrhart, F., Zimmermann, H., Feilen, P. & Weber, M. M. Alginate encapsulation improves viability and integrity of cryopreserved pancreatic islets and multicellular spheroids: combined fluorescence, scanning and block-face scanning electron microscopy. Microsc Microanal 13, 190-191 (2007).
Kelm, J. M., Timmins, N. E., Brown, C. J., Fussenegger, M. & Nielsen, L. K. Method for generation of homogeneous multicellular tumor spheroids applicable to a wide variety of cell types. Biotechnol Bioeng 83, 173-180 (2003).
Kim, H. et al. Mesenchymal stem cell 3D encapsulation technologies for biomimetic microenvironment in tissue regeneration. Stem Cell Res Ther 10, 51 (2019).
Kim, J. B. Three-dimensional tissue culture models in cancer biology. Semin Cancer Biol 15, 365-377 (2005).
Kleinman, H. K. & Martin, G. R. Matrigel: Basement membrane matrix with biological activity. Semin Cancer Biol 15, 378-386 (2005).
Kühlcke, K et al. Highly Efficient Retroviral Gene Transfer Based on Centrifugation-Mediated Vector Preloading of Tissue Culture Vessels. Mol Ther 5, 473-478 (2002).
Kurosawa, H. Methods for inducing embryoid body formation: in vitro differentiation system of embryonic stem cells. J Biosci Bioeng 103, 389-398 (2007).
Laschke, M. W. & Menger, M. D. Life is 3D: Boosting Spheroid Function for Tissue Engineering. Trends Biotechnol 35, 133-144 (2017).
Law, S. & Chaudhuri, S. Mesenchymal stem cell and regenerative medicine: regeneration versus immunomodulatory challenges. 22-38 (2013).
Lee et al., The use of injectable spherically symmetric cell aggregates self-assembled in a thermos-responsive hydrogel for enhanced cell transplantation. Biomaterials 30, 5505-5513 (2009).
Lee, K. H et al. Diffusion-mediated in situ alginate encapsulation of cell spheroids using microscale concave well and nanoporous membrane. Lab Chip 11, 1168-1173 (2011).
Li et al. Survival advantages of multicellular spheroids vs. monolayers of HepG2 cells in vitro. Oncol Rep 20, 1465-1471 (2008).
Lin, R.-Z., Chou, L.-F., Chien, C.-C. M. & Chang, H.-Y. Dynamic analysis of hepatoma spheroid formation: roles of E-cadherin and β1-integrin. Cell Tissue Res 324, 411-422 (2006).
Lin, R.-Z., Lin, R.-Z. & Chang, H.-Y. Recent advances in three-dimensional multicellular spheroid culture for biomedical research. Biotechnol J 3, 1172-1184 (2008).
Lv, D., Hu, Z., Lu, L., Lu, H. & Xu, X. Three-dimensional cell culture: A powerful tool in tumor research and drug discovery. Oncol Lett 14, 6999-7010 (2017).
Massie, I., Selden, C., Hodgson, H. & Fuller, B. Cryopreservation of Encapsulated Liver Spheroids for a Bioartificial Liver: Reducing Latent Cryoinjury Using an Ice Nucleating Agent. Tissue Eng Part C Methods 17, 765-774 (2011).
Mueller-Klieser, W. Method for the determination of oxygen consumption rates and diffusion coefficients in multicellular spheroids. Biophys J 46, 343-348 (1984).
Murphy, K. C., Whitehead, J., Zhou, D., Ho, S. S. & Leach, J. K. Engineering fibrin hydrogels to promote the wound healing potential of mesenchymal stem cell spheroids. Acta Biomater 64, 176-186 (2017).
Nath, S. & Devi, G. R. Three-dimensional culture systems in cancer research: Focus on tumor spheroid model. Pharmacol Therapeut 163, 94-108 (2016).
National Center for Biotechnology Information. PubChem Compound Summary for CID 37768, Amikacin. Retrieved Oct. 15, 2020 from https://pubchem.ncbi.nlm.nih.gov/compound/Amikacin (2020).
Pampaloni, F., Reynaud, E. G. & Stelzer, E. H. K. The third dimension bridges the gap between cell culture and live tissue. Nat Rev Mol Cell Bio 8, 839-845 (2007).
Paca, S. P. The rise of three-dimensional human brain cultures. Nature 553, 437-445 (2018).
Patra, B., Peng, C.-C., Liao, W.-H., Lee, C.-H. & Tung, Y.-C. Drug testing and flow cytometry analysis on a large number of uniform sized tumor spheroids using a microfluidic device. Sci Rep-uk 6, 21061 (2016). 12 pages.
Place, E. S., George, J. H., Williams, C. K. & Stevens, M. M. Synthetic polymer scaffolds for tissue engineering. Chem Soc Rev 38, 1139-1151 (2009).
Potta, T. et al. Discovery of antibiotics-derived polymers for gene delivery using combinatorial synthesis and cheminformatics modeling. Biomaterials 35, 1977-1988 (2014).
Qutub, A. A. & Popel, A. S. Elongation, proliferation & migration differentiate endothelial cell phenotypes and determine capillary sprouting. Bmc Syst Biol 3, 13 (2009).
Rege, K. et al. Investigation of DNA-Binding Properties of an Aminoglycoside-Polyamine Library Using Quantitative Structure-Activity Relationship (QSAR) Models. J Chem Inf Model 45, 1854-1863 (2005).
Rege, K., Hu, S., Moore, J. A., Dordick, J. S. & Cramer, S. M. Chemoenzymatic Synthesis and High-Throughput Screening of an Aminoglycoside-Polyamine Library: Identification of High-Affinity Displacers and DNA-Binding Ligands. J Am Chem Soc 126, 12306-12315 (2004).
Ryu, N.-E., Lee, S.-H. & Park, H. Spheroid Culture System Methods and Applications for Mesenchymal Stem Cells. Cells 8, 1620 (2019). 13 pages.
Skardal, A., Sarker, S. F., Crabbé, A., Nickerson, C. A. & Prestwich, G. D. The generation of 3-D tissue models based on hyaluronan hydrogel-coated microcarriers within a rotating wall vessel bioreactor. Biomaterials 31, 8426-8435 (2010).
Suenaga, H., Furukawa, K. S., Suzuki, Y., Takato, T. & Ushida, T. Bone regeneration in calvarial defects in a rat model by implantation of human bone marrow-derived mesenchymal stromal cell spheroids. J Mater Sci Mater Medicine 26, 254 (2015). 9 pages.
Tan, W., Krishnaraj, R. & Desai, T. A. Evaluation of Nanostructured Composite Collagen-Chitosan Matrices for Tissue Engineering. Tissue Engineering 7, 203-210 (2001).

(56) References Cited

OTHER PUBLICATIONS

Tokuyama, H. & Yazaki, N. Preparation of poly(N-isopropylacrylamide) hydrogel beads by circulation polymerization. React Funct Polym 70, 967-971 (2010).

Tostões, R. M et al. Perfusion of 3D encapsulated hepatocytes-A synergistic effect enhancing long-term functionality in bioreactors. Biotechnol Bioeng 108, 41-49 (2011).

Trevino, A. E et al. Chromatin accessibility dynamics in a model of human forebrain development. Science 367, eaay1645 (2020). 13 pages.

Tseng, T.-C. & Hsu, S. Substrate-mediated nanoparticle/gene delivery to MSC spheroids and their applications in peripheral nerve regeneration. Biomaterials 35, 2630-2641 (2014).

Wästfelt, M., Fadeel, B. & Henter, J.-I. A journey of hope: lessons learned from studies on rare diseases and orphan drugs. J Intern Med 260, 1-10 (2006).

Weaver, V. M. et al. Reversion of the Malignant Phenotype of Human Breast Cells in Three-Dimensional Culture and In Vivo by Integrin Blocking Antibodies. The Journal of Cell Biology 137, 131-145 (1997).

Weigelt, B., Ghajar, C. M. & Bissell, M. J. The need for complex 3D culture models to unravel novel pathways and identify accurate biomarkers in breast cancer. Adv Drug Deliver Rev 69, 42-51 (2014).

Williams et al., Encapsulation of Adipose Stromal Vascular Fraction Cells in Alginate Hydrogel Spheroids Using a Direct-Write Three-Dimensional Printing System. Bioresearch Open Access 2, 448-454 (2013).

Yamaguchi, Y., Ohno, J., Sato, A., Kido, H. & Fukushima, T. Mesenchymal stem cell spheroids exhibit enhanced in-vitro and in-vivo osteoregenerative potential. Bmc Biotechnol 14, 105 (2014). 10 pages.

Zhang, Q. et al. Three-Dimensional Spheroid Culture of Human Gingiva-Derived Mesenchymal Stem Cells Enhances Mitigation of Chemotherapy-Induced Oral Mucositis. Stem Cells Dev 21, 937-947 (2012).

* cited by examiner

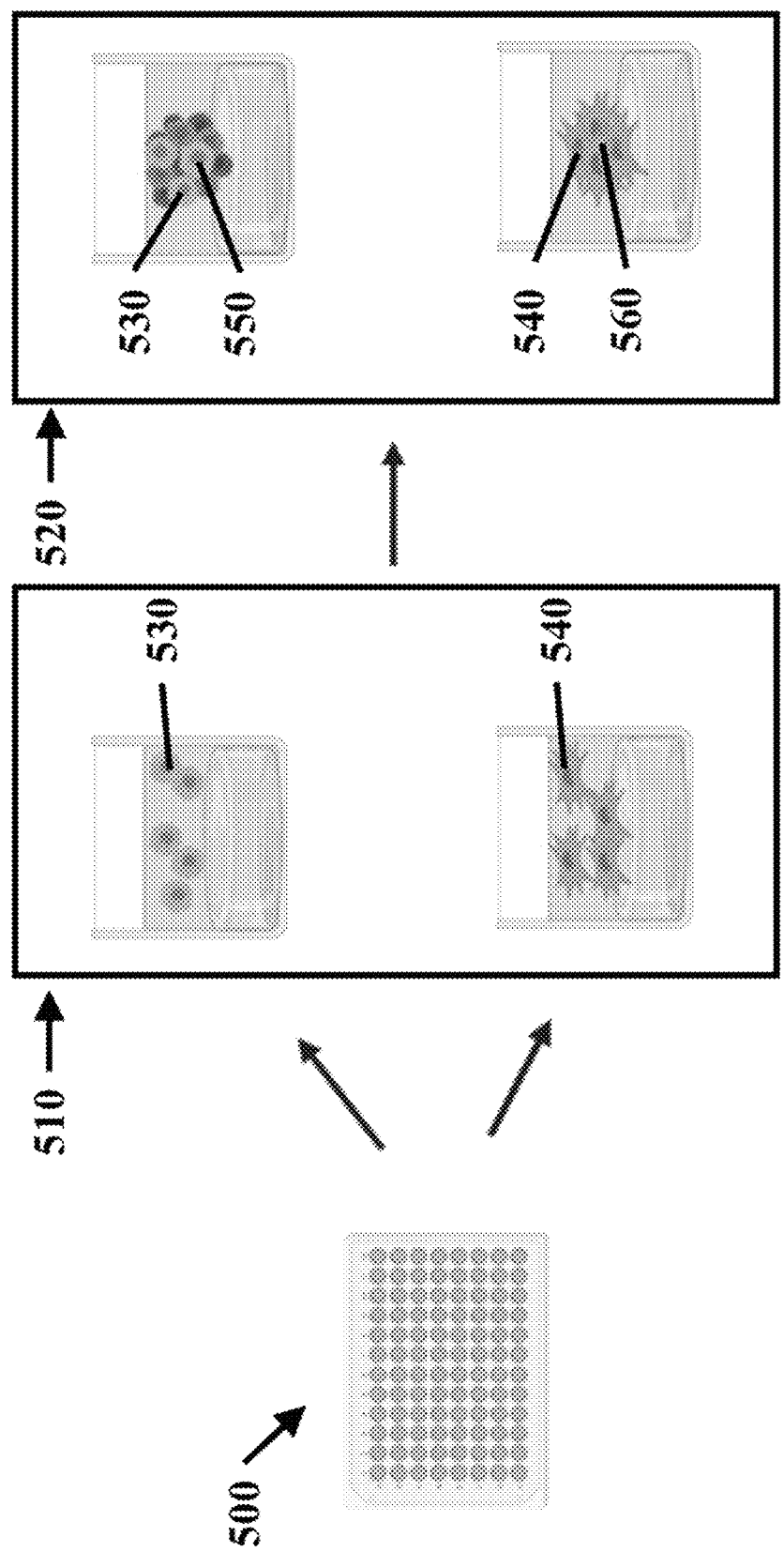

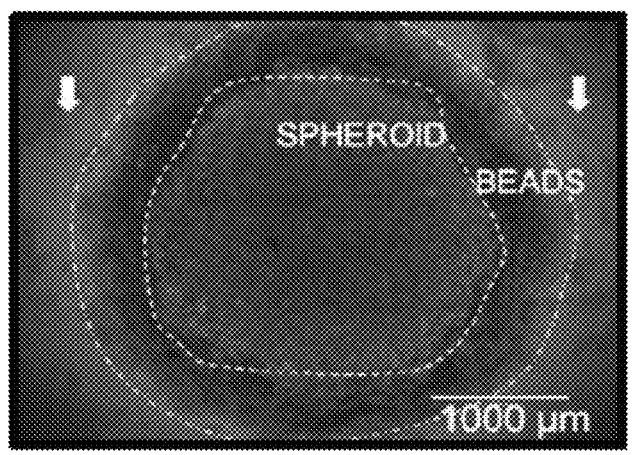
FIG. 13A
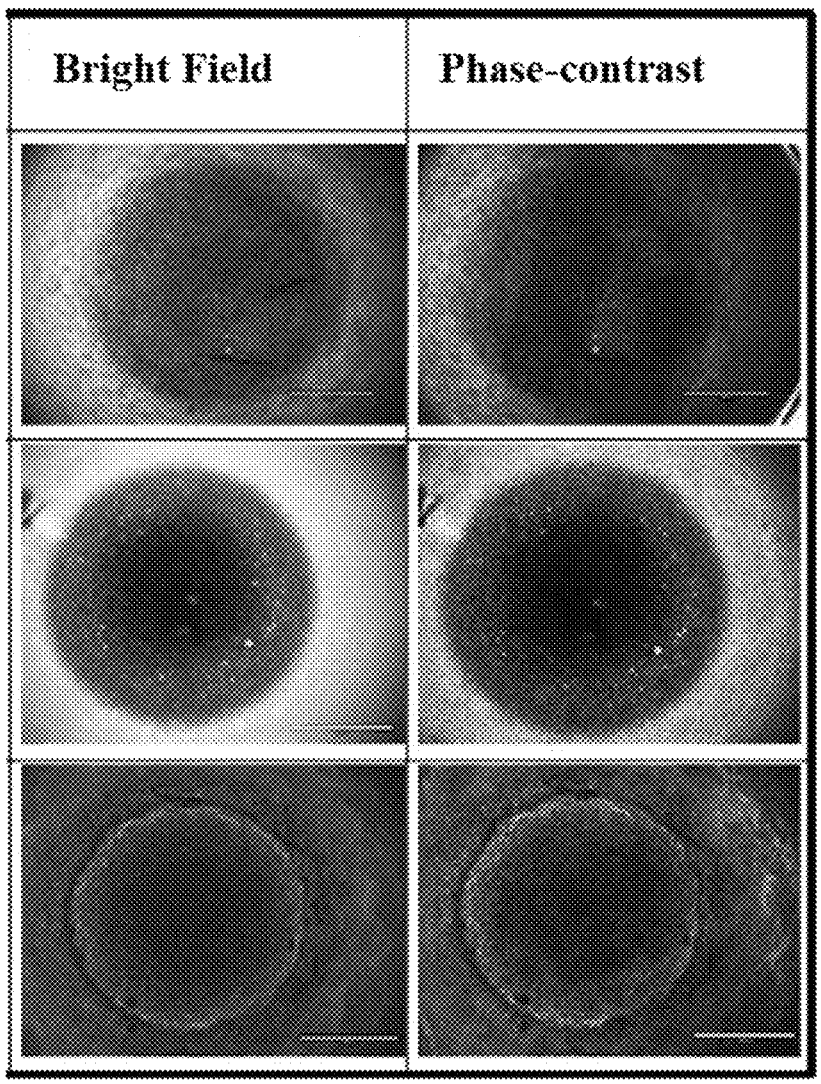
FIG. 13B
FIG. 13C
FIG. 13D

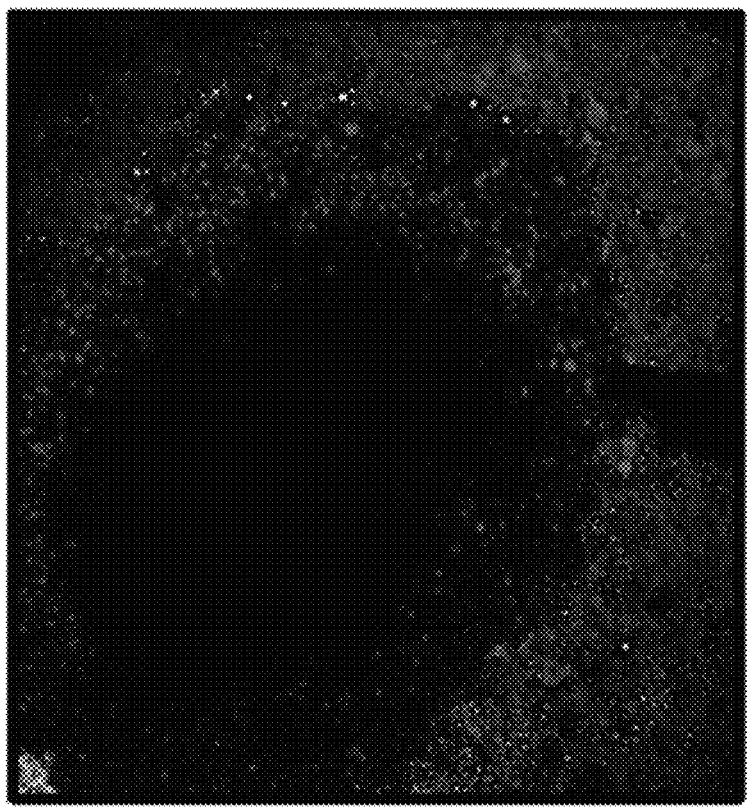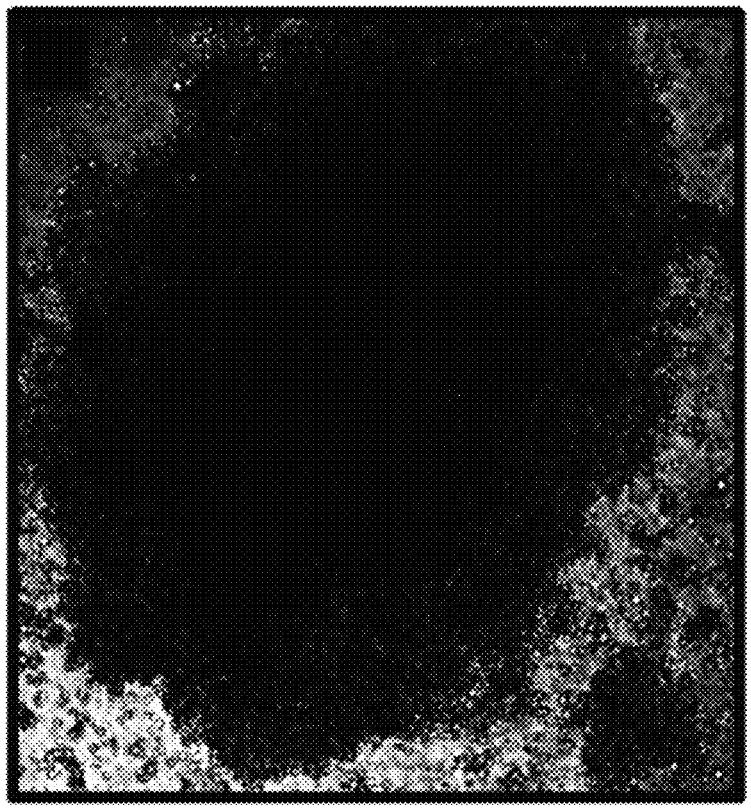
FIG. 22A

AMINOGLYCOSIDE ANTIBIOTIC-DERIVED MICROBEAD-ENCAPSULATED SPHEROIDS AND METHODS OF MAKING AND USING THE SAME

CROSS-REFERENCE TO RELATED APPLICATIONS

This application claims priority to and benefit of U.S. Provisional Application Ser. No. 63/115,504, filed Nov. 18, 2020, entitled "Encapsulation of Spheroids Using Aminoglycoside Antibiotic-Derived Microbeads," which is incorporated herein by reference in its entirety.

TECHNICAL FIELD

The present disclosure is directed to compositions comprising an encapsulated spheroid, methods of creating an encapsulated spheroid, and methods of using an encapsulated spheroid. More particularly, the present disclosure is related to a spheroid encapsulated by aminoglycoside antibiotic-derived hydrogel beads, and methods of making and using the same.

BACKGROUND

Cellular assays are the backbone of biological studies—be it for tissue modeling, drug discovery, therapeutics, or diagnostics. Two-dimensional (2D) cell culture has been deployed for several decades to garner physiologically relevant information and predict data before the cost-intensive animal testing. Although 2D techniques have been valuable for cellular assays, they have a colossal limitation—they do not adequately consider the natural three-dimensional (3D) microenvironment of the cells. As a result, they sometimes provide misleading statistics. Therefore, it is important to develop a 3D model that predicts cellular behaviors and their interaction with neighboring cells and extracellular matrix (ECM) in a more realistic manner. In recent biomedical research, various platforms have been modeled to generate 3D prototypes of tissues, spheroids, in vitro that could allow the study of cellular responses resembling in vivo environments, such as matrices, scaffolds, and devices. But most of these platforms have drawbacks such as lack of spheroid size control, low yield, or high cost associated with them.

On the other hand, aminoglycoside antibiotic-derived hydrogel is a low cost, high-fidelity platform that can facilitate the convenient generation of tumor and stem cell spheroids. Aminoglycoside antibiotic-derived hydrogel is a chemo mechanically engineered versatile platform for generation of 3D tumor spheroids (Grandhi, T. S. P., et al. "Chemomechanically engineered 3D organotypic platforms of bladder cancer dormancy and reactivation," *Biomaterials* 142: 171-185 (2017), which is hereby incorporated by reference in its entirety). It is a polymer of amikacin hydrate (AH) and poly(ethylene glycol) diglycidyl ether (PEGDE) and acts as a multipurpose technology to facilitate the identification of different therapeutic approaches for the ablation of spheroids as well as escaped cells. Furthermore, aminoglycoside antibiotic-derived hydrogel beads are derived from the same monomers as aminoglycoside antibiotic-derived hydrogel. They are a versatile platform with several chemical groups that can be exploited for encapsulating the spheroids and investigating the delivery of bioactive compounds to the cells.

Significant research has been conducted on encapsulating spheroids to study cellular progression and dormancy in 3D culture. Most commonly, microfluidic devices have been exploited to encapsulate spheroids in biocompatible materials such as alginate, but the devices are expensive and complex. Recently, cellular capsules have been used as a substitute tool for spheroid encapsulation and study of tumor progression in vivo (Alessandri, K. et al. "Cellular capsules as a tool for multicellular spheroid production and for investigating the mechanics of tumor progression in vitro," *Proc National Acad Sci* 110: 14843-14848 (2013), which is hereby incorporated by reference in its entirety). The capsules consisted of encapsulating cells in an aqueous core enclosed by an alginate shell in gentle, oil-free conditions. The gel allowed permeability of nutrients into the capsule and cell proliferation in a scaffold-free environment, thus integrating mechanical cues from the tumor microenvironment.

While there are various studies available on encapsulation of spheroids in alginate, their encapsulation in hydrogel microbeads is a novel concept that this research aims to achieve, as illustrated in FIG. 1. The present disclosure features novel compositions comprising spheroids encapsulated in aminoglycoside antibiotic-derived hydrogel beads that can be used in a variety of applications, including as three-dimensional tumor and stem cell models for applications in tissue engineering and regenerative medicine.

SUMMARY

The present disclosure is directed to compositions comprising an encapsulated spheroid, methods of creating an encapsulated spheroid, and methods of using an encapsulated spheroid. In an embodiment, a composition may comprise a spheroid. The spheroid comprises a plurality of cells and aminoglycoside antibiotic-derived hydrogel beads, wherein the spheroid is encapsulated by the aminoglycoside antibiotic-derived hydrogel beads to form an encapsulated spheroid.

In another embodiment, a method of creating an encapsulated spheroid may comprise coating a surface with an aminoglycoside antibiotic-derived hydrogel, culturing a plurality of cells on the surface, thereby creating a spheroid comprising the plurality of cells, and encapsulating the spheroid with a plurality of aminoglycoside antibiotic-derived hydrogel beads, thereby creating the encapsulated spheroid.

In a further embodiment, a method may comprise administering a compound to an encapsulated spheroid. In an embodiment, the encapsulated spheroid comprises a spheroid comprising a plurality of cells, and aminoglycoside antibiotic-derived hydrogel beads. In an embodiment, the spheroid is encapsulated by the aminoglycoside antibiotic-derived hydrogel beads to form the encapsulated spheroid. In an embodiment, the spheroid comprises an organoid.

BRIEF DESCRIPTION OF THE DRAWINGS

The file of this patent application contains at least one drawing/photograph executed in color. Copies of this patent application with color drawing(s)/photograph(s) will be provided by the Office upon request and payment of the necessary fee.

FIG. 5 illustrates an embodiment of a method of generating spheroids using aminoglycoside antibiotic-derived hydrogel, in accordance with the present disclosure.

FIG. 13A is a representative bright field image demonstrating an encapsulated spheroid, in accordance with the present disclosure.

FIG. 13B includes representative bright field (left; 4×, scale bar is 1000 μm) and phase-contrast (right; 4×, scale bar is 1000 μm) images of encapsulated spheroids cultured in 0.15 mg/mL quaternized aminoglycoside antibiotic-derived hydrogel beads, in accordance with the present disclosure.

FIG. 13C includes representative bright field (left; 4×, scale bar is 1000 μm) and phase-contrast (right; 4×, scale bar is 1000 μm) images of encapsulated spheroids cultured in 0.75 mg/mL quaternized aminoglycoside antibiotic-derived hydrogel beads, in accordance with the present disclosure.

FIG. 13D includes representative bright field (left; 4×, scale bar is 1000 μm) and phase-contrast (right; 4×, scale bar is 1000 μm) images of encapsulated spheroids cultured in 1.5 mg/mL quaternized aminoglycoside antibiotic-derived hydrogel beads, in accordance with the present disclosure.

FIG. 22A includes representative images of an encapsulated spheroid, in accordance with the present disclosure.

DETAILED DESCRIPTION

Figure 1:
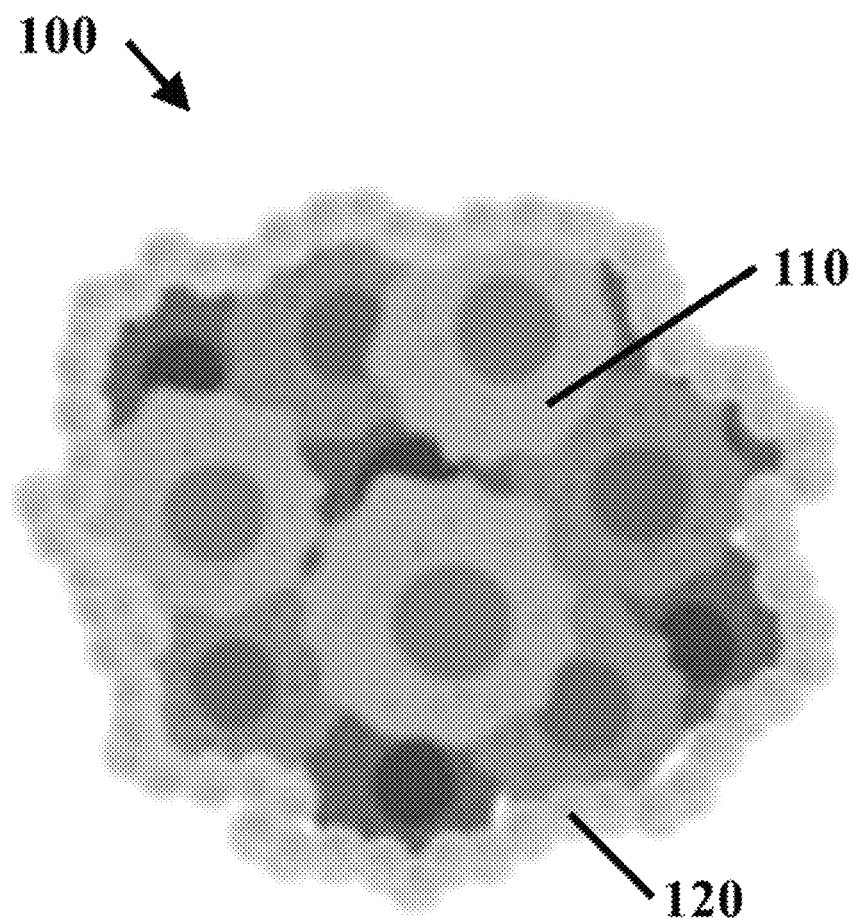
FIG. 1 is a schematic representation of an embodiment of an encapsulated spheroid, in accordance with the present disclosure.

This disclosure is not limited to the particular systems, devices and methods described, as these may vary. The terminology used in the description is for the purpose of describing the particular versions or embodiments only, and is not intended to limit the scope.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, "spheroid" refers to a mass of cells in a sphere-like structure. A spheroid comprises cells. A spheroid may also comprise non-cellular components. In certain embodiments, a spheroid may comprise an organoid, as described herein.

As used herein, "cell type" refers to cells that share morphological and/or phenotypical features. A cell type is a classification used to identify cells.

As used herein, "organoid" refers to a miniaturized and simplified version of an organ produced in vitro in three dimensions that shows realistic micro-anatomy. Organoids may be derived from one cell or a few cells from a tissue, embryonic stem cells, or induced pluripotent stem cells. The cells in organoids can self-organize in three-dimensional culture owing to their self-renewal and differentiation capacities.

As used herein, "bioactive agent" refers to any molecule or compound that has an effect on a living cell or organism. A bioactive agent may be selected from a pharmaceutical composition, a small molecule compound, a biologic compound, a peptide or protein.

As used herein, "conjugate" refers to the reversible combination of two molecules. The term "to conjugate" refers to the act of joining two molecules. The term "conjugated" may be used to describe the compound resulting from the act of joining two molecules.

The term "plurality" encompasses multiple species. As used herein, for example, the term "plurality" may encompass multiple cell types or multiple aminoglycoside antibiotic-derived hydrogel beads.

As used herein, the terms "administer," "administering" or "administration" as used herein refer to directly administering a compound or a composition to a subject.

As used herein, the term "effective amount" refers to an amount that results in measurable inhibition of at least one symptom or parameter of a specific disorder or pathological process. As used herein the term "therapeutically effective amount" of compositions of the application is an amount, which confers a therapeutic effect on the treated subject, at a reasonable benefit/risk ratio applicable to any medical treatment. The therapeutic effect may be objective (that is, measurable by some test or marker) or subjective (that is, subject gives an indication of or feels an effect or physician observes a change).

As used herein, "parental aminoglycoside antibiotic-derived hydrogel beads" refers to aminoglycoside antibiotic-derived hydrogel beads prior to further processing after formation.

As used herein, "quarternized aminoglycoside antibiotic-derived hydrogel beads" refers to the aminoglycoside antibiotic-derived hydrogel beads after quaternization of the amines and hydroxyls present in parental aminoglycoside antibiotic-derived hydrogel beads.

In an embodiment, a composition may comprise a spheroid, as described herein. In some embodiments, the spheroid may comprise a plurality of cells, as described herein. In certain embodiments, the composition may further comprise aminoglycoside antibiotic-derived hydrogel beads, as described herein. In some embodiments, the spheroid may be encapsulated by the aminoglycoside antibiotic-derived hydrogel beads to form an encapsulated spheroid, as described herein.

In certain embodiments, the spheroid may have a diameter of from about 100 µm to about 2,000 µm. The spheroid may have a diameter of, for example, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, about 1,000 µm, about 1,050 µm, about 1,100 µm, about 1,150 µm, about 1,200 µm, about 1,250 µm, about 1,300 µm, about 1,350 µm, about 1,400 µm, about 1,450 µm, about 1,500 µm, about 1,550 µm, about 1,600 µm, about 1,650 µm, about 1,700 µm, about 1,750 µm, about 1,800 µm, about 1,850 µm, about 1,900 µm, about 1,950 µm, about 2,000 µm, or any range between any two of these values, including endpoints. In certain embodiments, the diameter of the spheroid may be from about 300 µm to about 1,200 µm.

In certain embodiments, the plurality of cells may comprise a plurality of cell types. In some embodiments, the plurality of cells may comprise one cell type. In some embodiments, the plurality of cells may comprise more than one cell types. In some embodiments, the plurality of cells may comprise two or more cell types. In certain embodiments, the plurality of cells may be, for example, mesenchymal stem cells, T-47D cells, and A375 cells.

In certain embodiments, the plurality of cells types may be evenly distributed throughout the spheroid. In certain embodiments, the plurality of cell types may be randomly distributed throughout the spheroid. In certain embodiments, the plurality of cell types may be arranged in defined layers, wherein a first layer of cells is fully encapsulated by a second layer of cells. In some embodiments, the plurality of cell types are arranged in two or more layers of cells.

In certain embodiments, the spheroid may comprise an organoid. In certain embodiments, the organoid comprises vasculature, immune cells, or a combination thereof. In certain embodiments, the organoid may function like an organ. In an embodiment, the organ may be selected from a lung, a liver, a heart, and a kidney.

In certain embodiments, the spheroid may further comprise a non-cellular component. In some embodiments, the non-cellular component may be a bioactive agent, as described herein.

In certain embodiments, the aminoglycoside antibiotic-derived hydrogel beads may have a diameter from about 2 µm to about 20 µm. The aminoglycoside antibiotic-derived hydrogel beads are spherical aminoglycoside antibiotic-derive hydrogels. In certain embodiments, the diameter of the aminoglycoside antibiotic-derived hydrogel beads may be at least about 1 µm. In certain embodiments, the diameter of the aminoglycoside antibiotic-derived hydrogel beads may be about 5 µm to about 15 µm. In certain embodiments, the diameter of the aminoglycoside antibiotic-derived hydrogel beads may be about 9 µm.

In certain embodiments, the aminoglycoside antibiotic-derived hydrogel may comprise amikacin hydrate (AH) and poly(ethylene glycol) diglycidyl ether (PEGDE) in stoichiometric ratios ranging from about 1:1 to about 1:6 AH:PEGDE. In certain embodiments, the aminoglycoside antibiotic-derived hydrogel may comprise amikacin hydrate (AH) and poly(ethylene glycol) diglycidyl ether (PEGDE) in a stoichiometric ratio of about 1:1 AH:PEGDE. In certain embodiments, the aminoglycoside antibiotic-derived hydrogel may comprise amikacin hydrate (AH) and poly(ethylene glycol) diglycidyl ether (PEGDE) in a stoichiometric ratio of about 1:1.5 AH:PEGDE. In certain embodiments, the aminoglycoside antibiotic-derived hydrogel may comprise amikacin hydrate (AH) and poly(ethylene glycol) diglycidyl ether (PEGDE) in a stoichiometric ratio of about 1:2 AH:PEGDE. In certain embodiments, the aminoglycoside antibiotic-derived hydrogel may comprise amikacin hydrate (AH) and poly(ethylene glycol) diglycidyl ether (PEGDE) in a stoichiometric ratio of about 1:2.7 AH:PEGDE. In certain embodiments, the aminoglycoside antibiotic-derived hydrogel may comprise amikacin hydrate (AH) and poly(ethylene glycol) diglycidyl ether (PEGDE) in a stoichiometric ratio of about 1:3 AH:PEGDE. In certain embodiments, the aminoglycoside antibiotic-derived hydrogel may comprise amikacin hydrate (AH) and poly(ethylene glycol) diglycidyl ether (PEGDE) in a stoichiometric ratio of about 1:4 AH:PEGDE. In certain embodiments, the aminoglycoside antibiotic-derived hydrogel may comprise amikacin hydrate (AH) and poly(ethylene glycol) diglycidyl ether (PEGDE) in a stoichiometric ratio of about 1:5 AH:PEGDE. In certain embodiments, the aminoglycoside antibiotic-derived hydrogel may comprise amikacin hydrate (AH) and poly(ethylene glycol) diglycidyl ether (PEGDE) in a stoichiometric ratio of about 1:6 AH:PEGDE. In certain embodiments, the plurality of the aminoglycoside antibiotic-derived hydrogel beads may be cross-linked.

In certain embodiments, the at least one of the aminoglycoside antibiotic-derived hydrogel beads may be conjugated to an additional molecule. In certain embodiments, the additional molecule may be selected from the group consisting of a fluorescent protein, a magnetic particle, derivatives thereof, and combinations thereof. In certain embodiments, the fluorescent protein may be Rhodamine-B or Fluorescein.

In certain embodiments, the encapsulated spheroid further may comprise a bioactive agent. In certain embodiments, the bioactive agent may be a small molecule, biologic, cell or gene therapy. In certain embodiments, the bioactive agent may be selected from the group consisting of vascular endothelial growth factor (VEGF), derivatives thereof, and combinations thereof. In certain embodiments, the bioactive agent may be encapsulated by the aminoglycoside antibiotic-derived hydrogel beads. In certain embodiments, the bioactive agent may be conjugated to at least one of the aminoglycoside antibiotic-derived hydrogel beads.

In certain embodiments, the composition may further comprise a second layer of cells, wherein the second layer of cells at least partially encases the encapsulated spheroid. In some embodiments, the second layer of cells partially encases the encapsulated spheroid. In other embodiments, the second layer of cells fully encases the encapsulated spheroid.

In certain embodiments, a method may comprise administering, to a subject in need thereof, an effective amount of the composition. In certain embodiments, the route administration may be selected from the group consisting of surgical implantation, injection, or any route of administration known to skilled artisan. In certain embodiments, the administering may be a single administration. In certain embodiments, the administering may be two or more administrations. In certain embodiments, the administering may occur on a routine basis as determined by a physician.

In certain embodiments, the subject may be a mammal. In certain embodiments, the subject may be a human. In certain embodiments, the subject may be a non-human mammal. Any non-human mammal may be suitable, such as mice, rats, guinea pigs and other small rodents, dogs, cats, sheep, goats, and monkeys.

In certain embodiments, the subject is in need of tissue repair and/or regeneration.

In certain embodiments, the spheroid may be configured to mimic a diseased tissue, and the composition may be configured to model a disease.

In an embodiment, a method of creating an encapsulated spheroid may comprise coating a surface with an aminoglycoside antibiotic-derived hydrogel. In certain embodiments, the aminoglycoside antibiotic-derived hydrogel comprises AH and PEGDE. Stoichiometric ratios may range from about 1:1 to about 1:6 AH:PEGDE. In some embodiments, the aminoglycoside antibiotic-derived hydrogel may have a thickness of about 1 mm.

In some embodiments, the method may further comprise culturing a plurality of cells on the surface, thereby creating a spheroid comprising the plurality of cells, as described herein. In certain embodiments, the plurality of cells may comprise T-47D or A375 cells, wherein the plurality of cells may be seeded onto aminoglycoside antibiotic-derived hydrogel at densities ranging from about 30,000 to about 100,000 cells per well in a 96-well plate. In certain embodiments, the plurality of cells are T-47D or A375 cells, wherein the plurality of cells may be seeded onto aminoglycoside antibiotic-derived hydrogel at densities ranging from about 750,000 to about 1,000,000 cells per well in a 24-well plate. In certain embodiments, the plurality of cells are hMSCs, wherein the plurality of cells may be seeded onto aminoglycoside antibiotic-derived hydrogel at densities of about 30,000 cells per well in a 96 well plate.

In certain embodiments, the spheroid is created after about 12 hours to 72 hours of culturing on aminoglycoside antibiotic-derived hydrogel. In certain embodiments, the spheroid is created after about 24 hours of culturing on aminoglycoside antibiotic-derived hydrogel. In certain embodiments, the spheroid is created after about 48 hours of culturing on aminoglycoside antibiotic-derived hydrogel.

In certain embodiments, the method may further comprise synthesizing the plurality of aminoglycoside antibiotic-derived hydrogel beads. In certain embodiments, the aminoglycoside antibiotic-derived hydrogel beads are synthesized using emulsion polymerization. In an embodiment, the emulsion polymerization may employ a AH:PEGDE ration of 1:2 to create a pre-gel formation. The pre-gel formation is collected in a syringe and dispensed slowly into a solution of mineral oil and 1% (w/v) Span-80 through a 27G1 ¼ needle and 5 mL syringe while stirring. The AH:PEGDE pre-gel forms parental aminoglycoside antibiotic-derived hydrogel beads. The mineral oil-surfactant solution is maintained at 65° C. Aminoglycoside antibiotic-derived hydrogel beads are washed extensively after gelling.

In certain embodiments, the aminoglycoside antibiotic-derived hydrogel beads may be parental aminoglycoside antibiotic-derived hydrogel beads. In certain embodiments, the aminoglycoside antibiotic-derived hydrogel beads may be quarternized aminoglycoside antibiotic-derived hydrogel beads. Quarternized aminoglycoside antibiotic-derived hydrogel beads are prepared as described herein. After washing, glycidyl trimethylammonium chloride (GTMAC) is used in an aqueous solution with parental aminoglycoside antibiotic-derived hydrogel beads to quarternize amines and hydroxyls present in parental aminoglycoside antibiotic-derived hydrogel beads.

In certain embodiments, the method may further comprise encapsulating the spheroid with a plurality of aminoglycoside antibiotic-derived hydrogel beads, as described herein, thereby creating the encapsulated spheroid. In certain embodiments, encapsulating the spheroid with the plurality of aminoglycoside antibiotic-derived hydrogel beads may further comprise subjecting the spheroid and the plurality of aminoglycoside antibiotic-derived hydrogel beads to centrifugation.

In certain embodiments, the encapsulated spheroid further may comprise a bioactive agent. In certain embodiments, the bioactive agent may be a small molecule, biologic, cell or gene therapy. In certain embodiments, the bioactive agent may be selected from the group consisting of vascular endothelial growth factor (VEGF), or derivatives thereof, and combinations thereof. In certain embodiments, the bioactive agent may be encapsulated by the aminoglycoside antibiotic-derived hydrogel beads. In certain embodiments, the bioactive agent may be conjugated to at least one of the aminoglycoside antibiotic-derived hydrogel beads.

In certain embodiments, the method may further comprise conjugating at least one of the aminoglycoside antibiotic-derived hydrogel beads with an additional molecule selected from the group consisting of a fluorescent protein, a magnetic particle, derivatives thereof, and combinations thereof. In certain embodiments, the fluorescent protein may be Rhodamine B or Fluorescein.

In certain embodiments, the method may further comprise cross-linking at least two of the aminoglycoside antibiotic-derived hydrogel beads.

In certain embodiments, the method may further comprise analyzing the function of the encapsulated spheroid.

In an embodiment, a method may comprise administering a compound to an encapsulated spheroid as described herein. In an embodiment, the encapsulated spheroid may comprise an organoid. In certain embodiments, the method may further comprise analyzing a function of the organoid. In certain embodiments, the method may further comprise analyzing a viability of the organoid after about 12 hours to about 78 hours.

In certain embodiments, the method may further comprise analyzing a byproduct of the organoid.

In an embodiment, a method may comprise applying a therapeutic agent to an encapsulated spheroid as described herein. In certain embodiments, the method may further comprise measuring biomarkers of the encapsulated spheroid to determine the safety and efficacy of the therapeutic agent. In an embodiment, the method may be used to perform a drug screening assay.

A variety of figures and images are included herein to help illustrate the concepts disclosed herein. FIG. 1 is a schematic representation of an embodiment an encapsulated spheroid 100. The encapsulated spheroid 100 comprises a spheroid, which comprises a plurality of cells 110. The encapsulated also comprises aminoglycoside antibiotic-derived hydrogel beads 120. The spheroid is encapsulated by the aminoglycoside antibiotic-derived hydrogel beads 120 to form the encapsulated spheroid 100.

Figure 2:
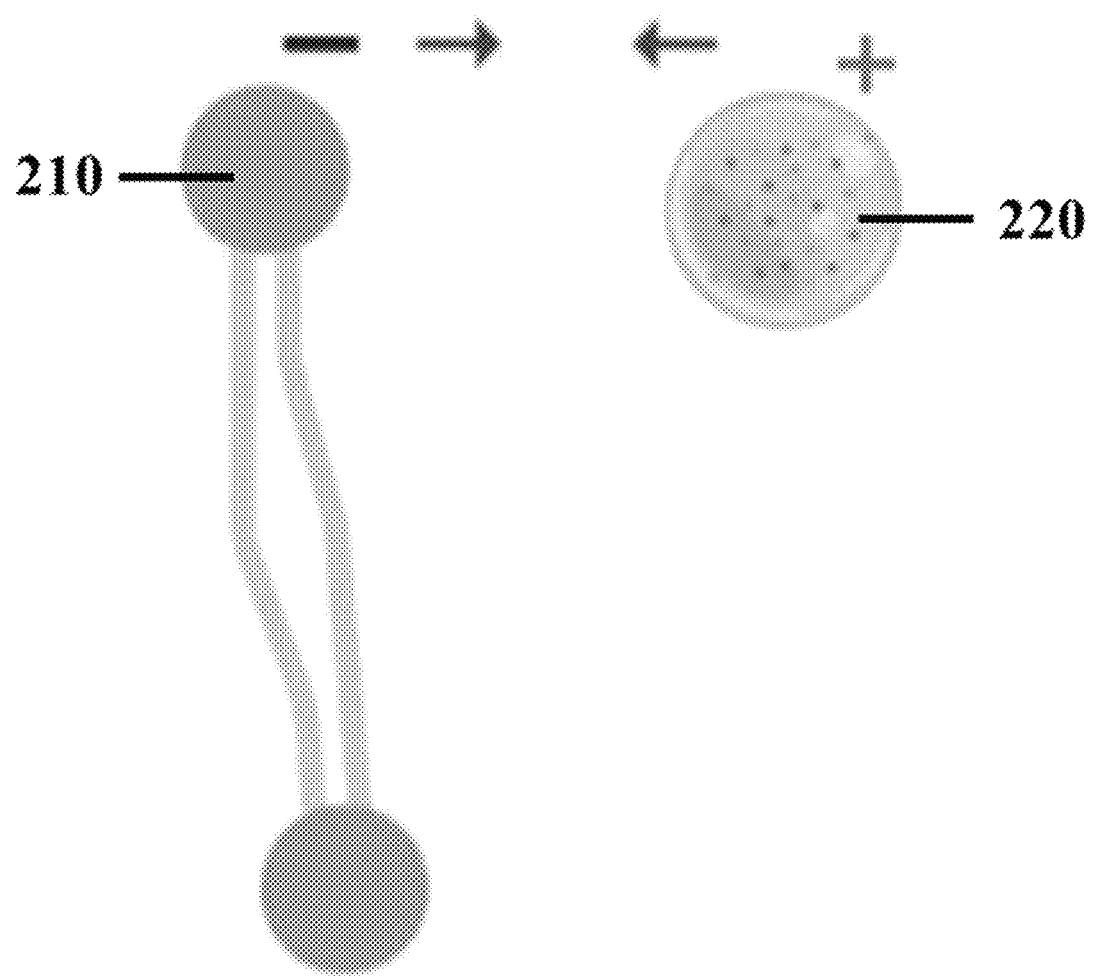
FIG. 2 is a schematic representation of charge interactions between a phospholipid bilayer and aminoglycoside antibiotic-derived hydrogel beads, in accordance with the present disclosure.

FIG. 2 is a schematic representation of charge interactions between a phospholipid bilayer 210 and aminoglycoside antibiotic-derived hydrogel beads 220. The phospholipid bilayer 210 is negatively charged, and the aminoglycoside antibiotic-derived hydrogel beads 220 are positively charged. In an embodiment, the negatively charged phospholipid bilayer 210 on one or more cells can interact with the positively charged aminoglycoside antibiotic-derived hydrogel beads 220 to form an encapsulated spheroid (not shown).

Figure 3:
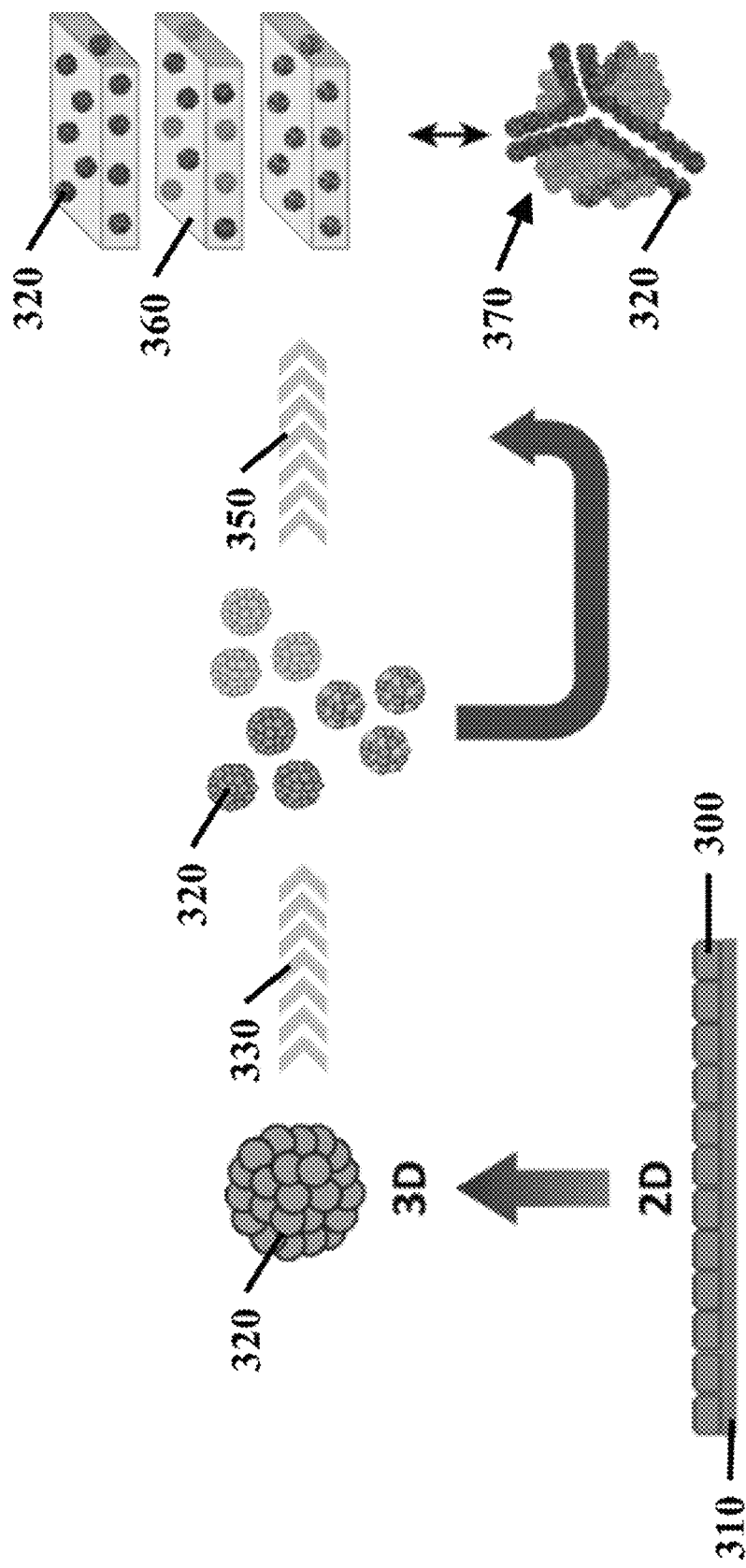
FIG. 3 illustrates an embodiment of a method of administering an encapsulated spheroid in a scaffold for tissue repair, in accordance with the present disclosure.

FIG. 3 illustrates an embodiment of a method of administering an encapsulated spheroid 320 in a scaffold for tissue repair and/or regeneration. First, a plurality of cells 300 are cultured in a monolayer over a aminoglycoside antibiotic-derived hydrogel 310. The plurality of cells may be of a single cell origin or multiple cell origins. Second, cell-cell interactions cause the monolayer to form an encapsulated spheroid 320. Without wishing to be bound by theory, the multidimensional structure of the encapsulated spheroid 320 may exhibit enhanced repair and regeneration properties such as cell viability, proliferation, differentiation, and angiogenesis in comparison to the monolayer. A plurality of encapsulated spheroids 320 may be produced 330 for tissue repair and regeneration. The encapsulated spheroids 320 may optionally be preconditioned or enhanced with biological agents. Encapsulated spheroids 320 from multiple cell culture origins may optionally be combined 350. For example, encapsulated spheroids 320 may be incorporated into a biocompatible scaffold 360, and the biocompatible scaffold 360 may optionally be bioabsorbable or biodegradable, leaving the encapsulated spheroids 320 to initiate the repair and/or regeneration of healthy tissue 370.

Figure 4A:
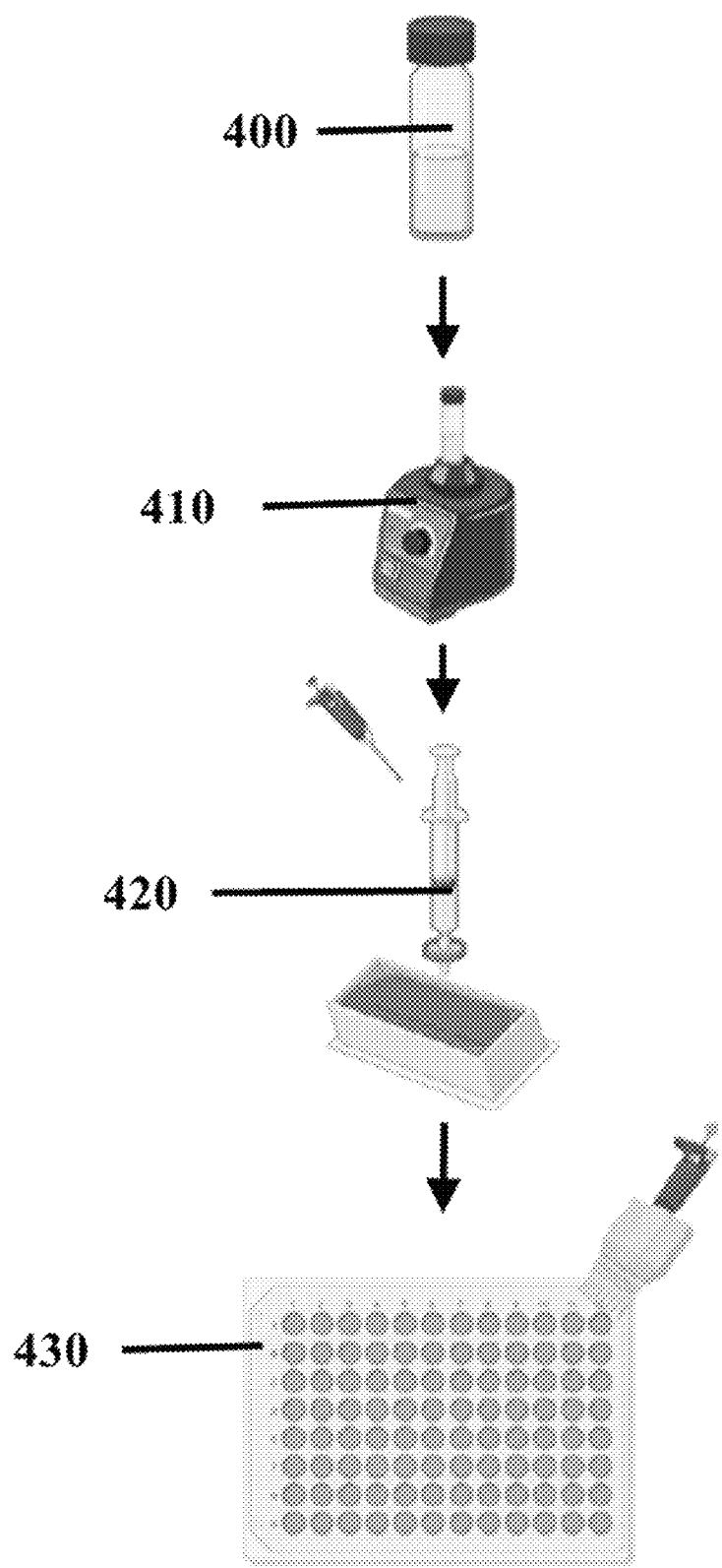
FIG. 4A illustrates an embodiment of a method of making an aminoglycoside antibiotic-derived hydrogel, in accordance with the present disclosure.
Figure 4B:
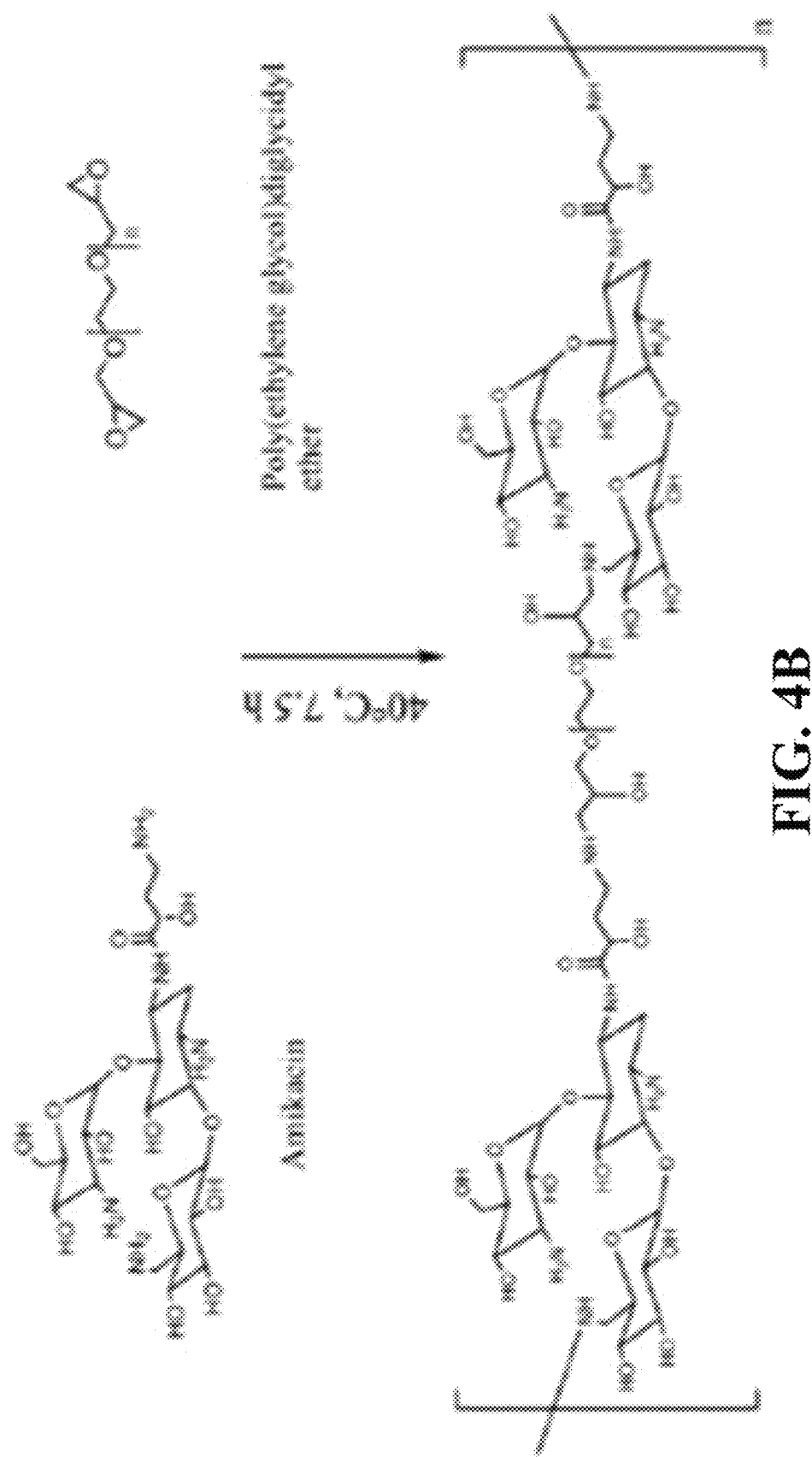
FIG. 4B illustrates an embodiment of a reaction between amikacin hydrate and a poly(ethylene glycol) diglycidyl ether pre-gel solution to form an aminoglycoside antibiotic-derived hydrogel, in accordance with the present disclosure.

FIG. 4A illustrates an embodiment of a method of making an aminoglycoside antibiotic-derived hydrogel. Amikacin hydrate (AH) and poly(ethylene glycol) diglycidyl ether (PEGDE) are combined 400 in NPW to form a pre-gel solution. The pre-gel solution is vortexed 410 until the pre-gel is transparent. The pre-gel is then filtered 420 through a 0.20 μm filter into a reservoir. The pre-gel solution is then added 430 to a culture plate and allowed to gel for 7.5 hours at 40° C. FIG. 4B illustrates an embodiment of a reaction between amikacin hydrate ("Amikacin"; top left) and poly(ethylene glycol) diglycidyl ether (top right) pre-gel solution resulting in the aminoglycoside antibiotic-derived hydrogel (bottom). The reaction occurs at about 40° C. for FIG. 5 illustrates an embodiment of a method of generating spheroids using aminoglycoside antibiotic-derived hydrogel. A culture plate is coated 500 with an aminoglycoside antibiotic-derived hydrogel. Cells are seeded 510 on the aminoglycoside antibiotic-derived hydrogel. In this example T-47D/A375 cells 530 and hMSCs 540 are used. Cells are cultured 520 and incubated at 37° C. and 5% CO2 to form a spheroid comprising T-47D/A375 cells 550 or a spheroid comprising hMSCs 560.

Figure 6:
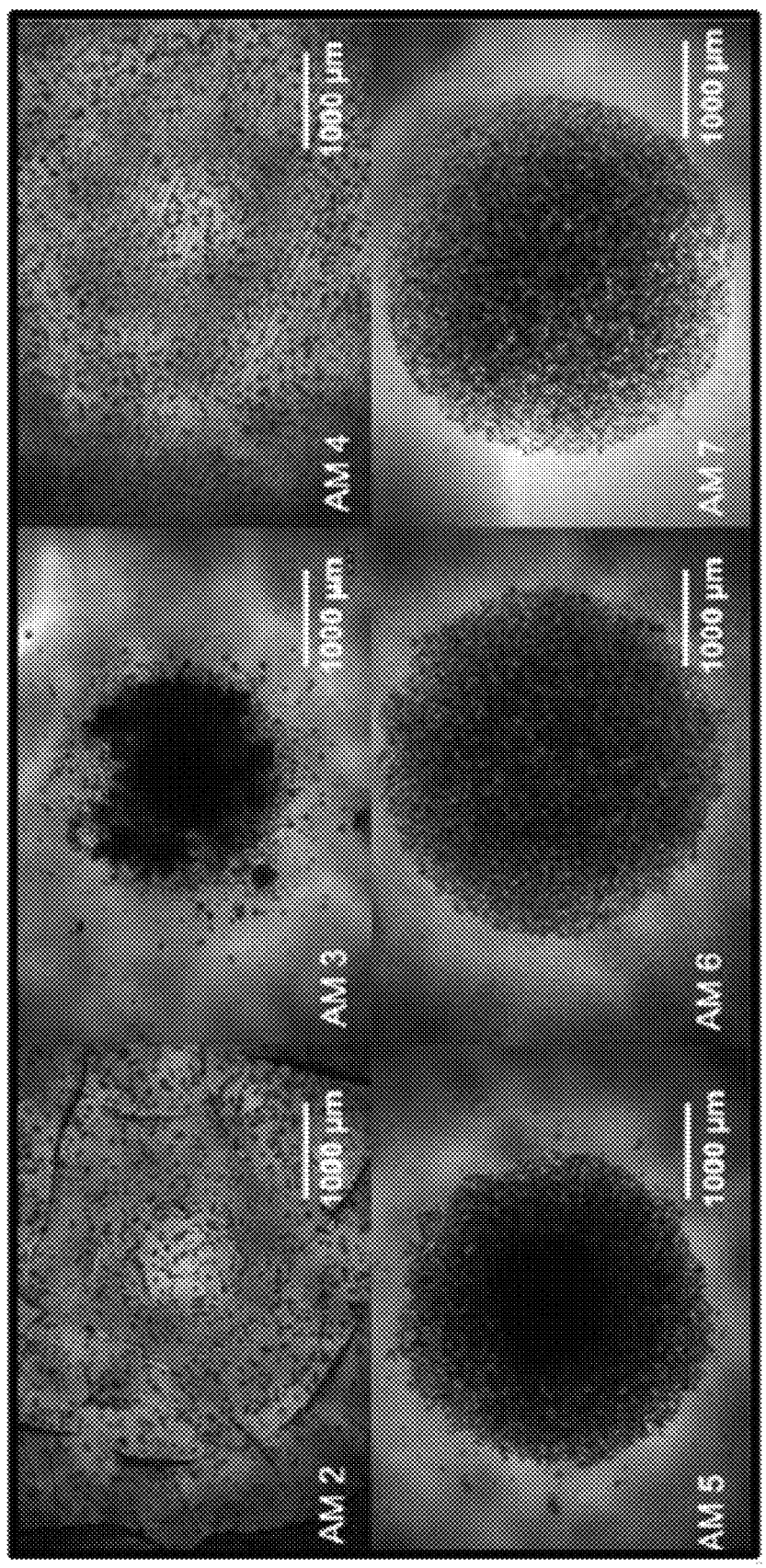
FIG. 6 is a representative image of spheroids comprising hMSCs cultured in 96-well cell culture plates coated with aminoglycoside antibiotic-derived hydrogels, in accordance with the present disclosure.

FIG. 6 is a representative image of spheroids comprising hMSCs cultured in 96-well cell culture plates coated with aminoglycoside antibiotic-derived hydrogels. hMSC cells were plated at an initial cell density of 30,000 cells per well. Each phase-contrast image is taken from a cell-culture plate coated with aminoglycoside antibiotic-derived hydrogels AM2 through AM7 after 3 days of incubation. AM2 through AM4 evidenced loosely spread cells and a cluster of cells was observed in AM5 which broke down when encapsulation studies were performed. AM6 and 7 demonstrated the formation of homogeneously packed spheroids (4× objective, scale bar—1000 μm).

Figure 7:
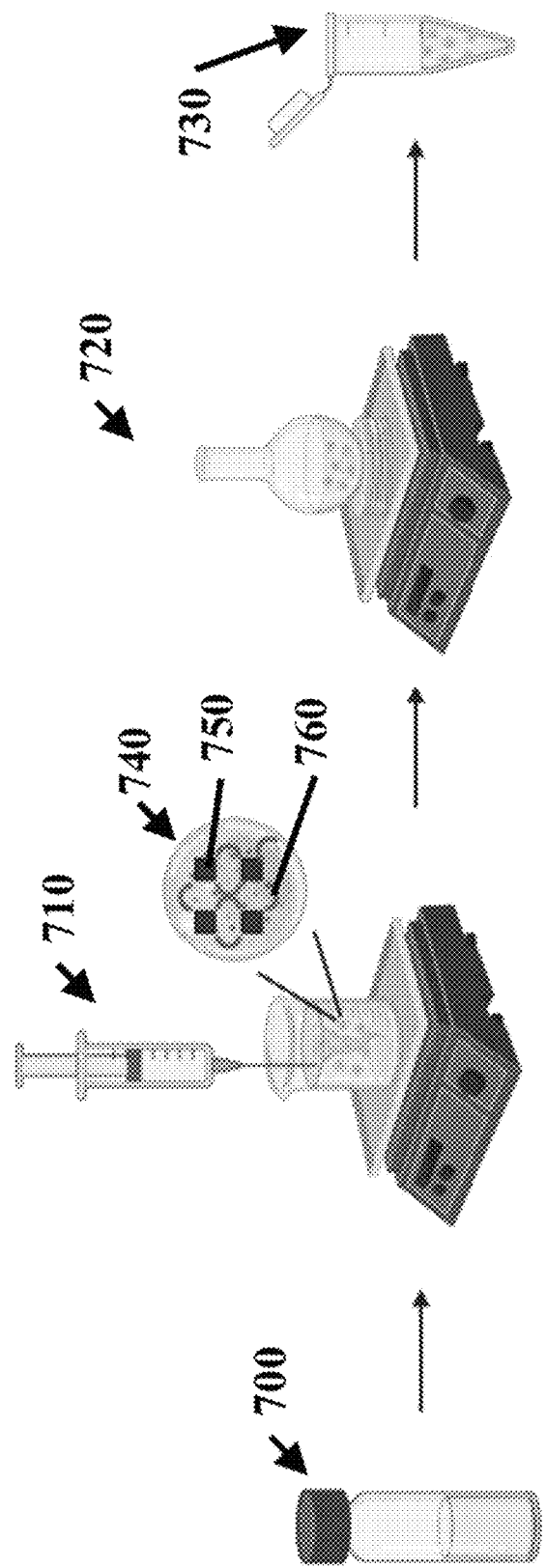
FIG. 7 illustrates an embodiment of a method of synthesizing parental aminoglycoside antibiotic-derived hydrogel beads, in accordance with the present disclosure.

FIG. 7 illustrates an embodiment of a method of synthesizing parental aminoglycoside antibiotic-derived hydrogel beads. Amikacin hydrate (AH) and poly(ethylene glycol) diglycidyl ether (PEGDE) are combined 700 in NPW to form a pre-gel solution 770. The pre-gel solution was added 710 to a mineral oil bath supplemented with 1% span-80 surfactant and maintained at 65° C. and stirring at 260 RPM for 25 minutes to form aminoglycoside antibiotic-derived hydrogel beads 740 comprising amikacin 750 and PEGDE 760. The AH+PEGDE solution is to form a pre-gel solution. Aminoglycoside antibiotic-derived hydrogel beads are washed 720 with Tween-20 and ready for use 730.

Figure 8:
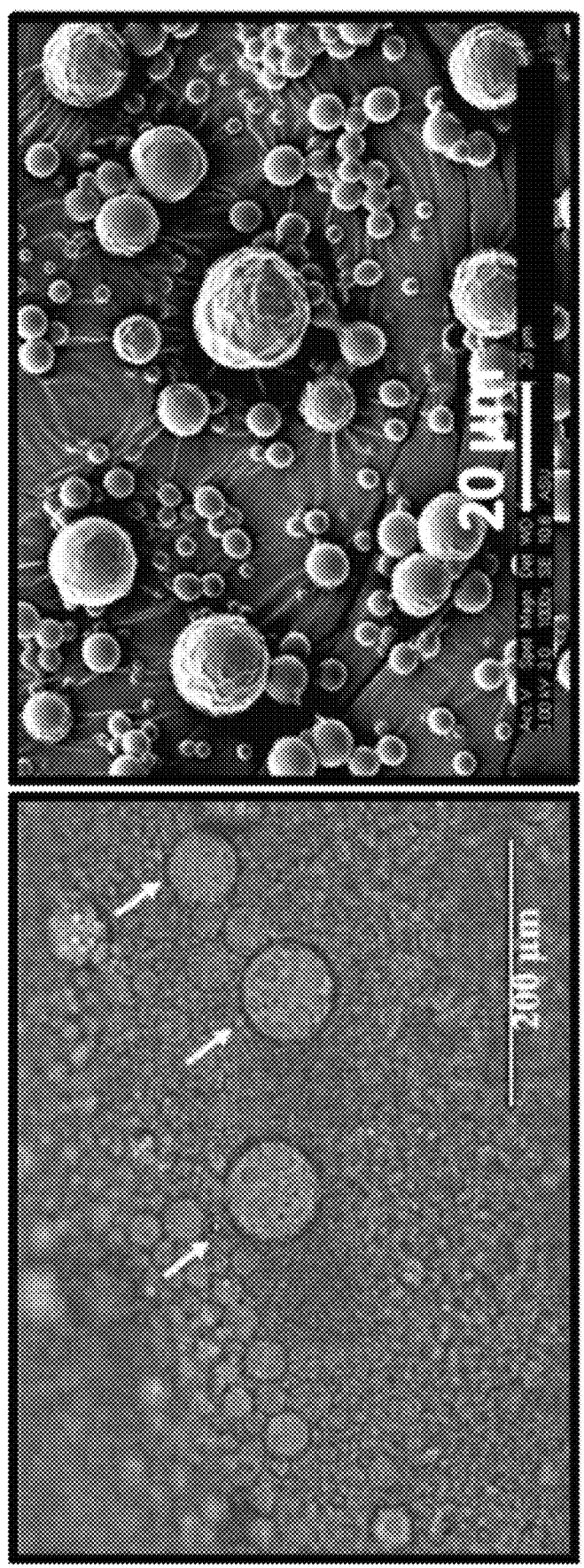
FIG. 8 is a representative image of aminoglycoside antibiotic-derived hydrogel beads, including a phase-contrast image of parental aminoglycoside antibiotic-derived hydrogel beads generated using an emulsion polymerization reaction (left), and spherical particles (right), in accordance with the present disclosure.

FIG. 8 is a representative image of aminoglycoside antibiotic-derived hydrogel beads. Left is a phase-contrast image of parental aminoglycoside antibiotic-derived hydrogel beads generated using an emulsion polymerization reaction. White arrows indicate individual beads with spherical morphology (scale bar is 200 μm). Right is an image from a scanning electron microscope of aminoglycoside antibiotic-derived hydrogel beads visualizing spherical particles with an average diameter of approximately 9 μm+/−4 μm (scale bar is 20 μm).

Figure 9:
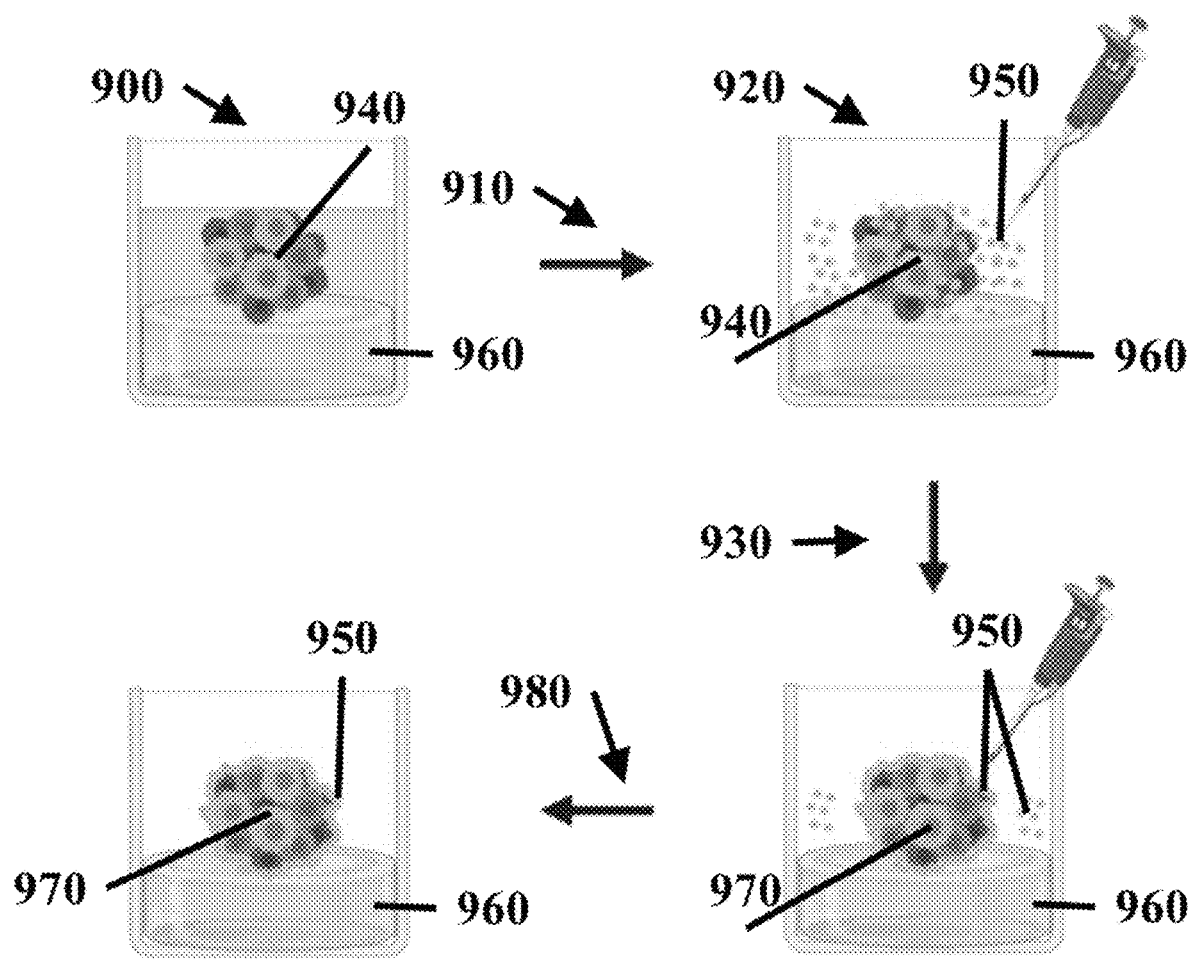
FIG. 9 illustrates an embodiment of a method of producing encapsulated spheroids, in accordance with the present disclosure.

FIG. 9 illustrates an embodiment of a method of producing encapsulated spheroids. Spheroids 940 are formed 900 on aminoglycoside antibiotic-derived hydrogel 960. Media is removed 910 and a solution containing aminoglycoside antibiotic-derived hydrogel beads 950 is added 920 to the spheroid. The spheroid and aminoglycoside antibiotic-derived hydrogel bead solution are incubated 930 at 37° C. for 24 hours to 48 hours. Optionally, the spheroid and aminoglycoside antibiotic-derived hydrogel bead solution may be centrifuged at 100 RPM for 15 minutes. An encapsulated spheroid 970 is formed. The encapsulated spheroid is washed 980 with phosphate buffered saline to remove extra aminoglycoside antibiotic-derived hydrogel beads resulting in aminoglycoside antibiotic-derived hydrogel bead encapsulated spheroids 970.

Figure 10:
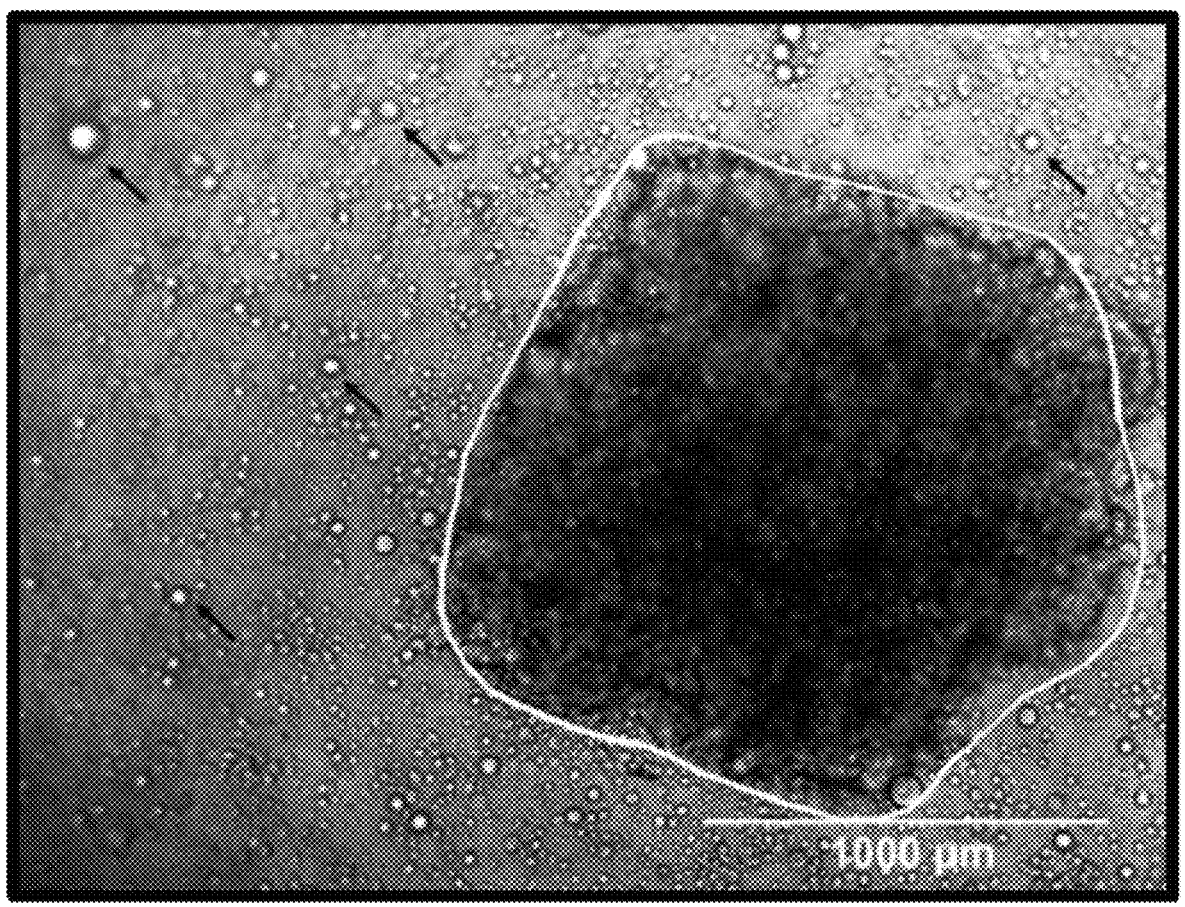
FIG. 10 is a representative image of a spheroid in a solution containing aminoglycoside antibiotic-derived hydrogel beads, in accordance with the present disclosure.

FIG. 10 is a representative image of a spheroid in a solution containing aminoglycoside antibiotic-derived hydrogel beads (arrows). A spheroid of T-47D cells were cultured at an initial cell density of 30,000 cells per well. A solution containing aminoglycoside antibiotic-derived hydrogel beads was added to the well (100 μL of 0.75 mg/mL) with the spheroid of T-47D cells. Image is a phase-contrast image in a 96 well cell culture plate at t=0 using a 4× objective (scale bar is 1000 μm).

Figure 11:
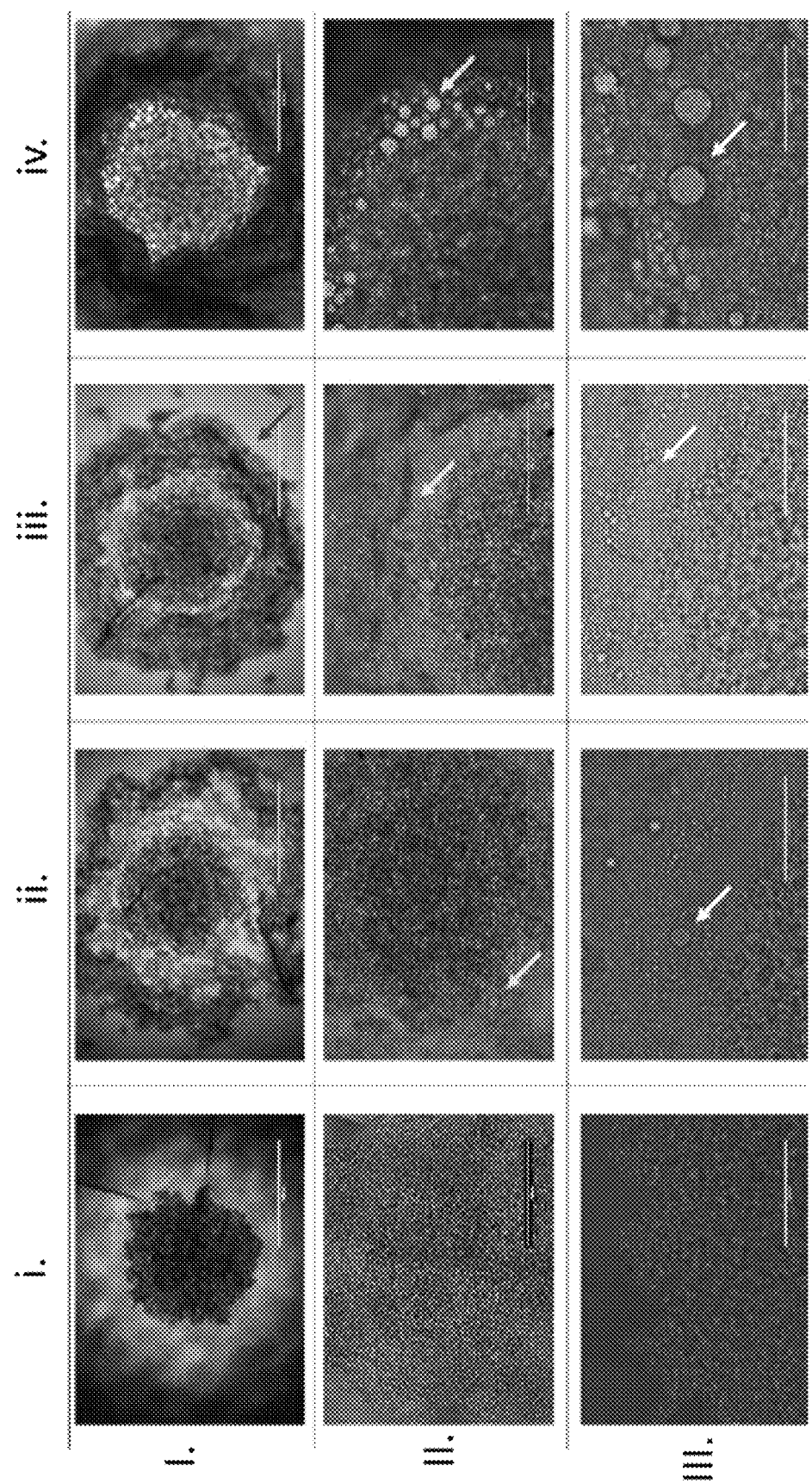
FIG. 11 includes representative images of encapsulated spheroids under a 4× objective (row I; scale bar is 1000 μm), 10× objective (row II; scale bar is 400 μm), or 20× objective (row III; scale bar is 200 μm), in accordance with the present disclosure.

FIG. 11 includes representative images of encapsulated spheroids under a 4× objective (row I; scale bar is 1000 μm), 10× objective (row II; scale bar is 400 μm), or 20× objective (row III; scale bar is 200 μm). Spheroids of T-47D cells (initial cell density=30,000 cells per well) were incubated with no aminoglycoside antibiotic-derived hydrogel beads (column i), 0.15 mg/mL quarternized aminoglycoside antibiotic-derived hydrogel beads (column ii), 0.75 mg/mL quarternized aminoglycoside antibiotic-derived hydrogel beads (column iii), or 1.5 mg/mL quarternized aminoglycoside antibiotic-derived hydrogel beads (column iv). Images were taken 24 hours after incubation. There is a direct correlation between the concentration of aminoglycoside antibiotic-derived hydrogel bead solution and the size and density of the encapsulation layer (red, yellow, and white arrows).

Figure 12:
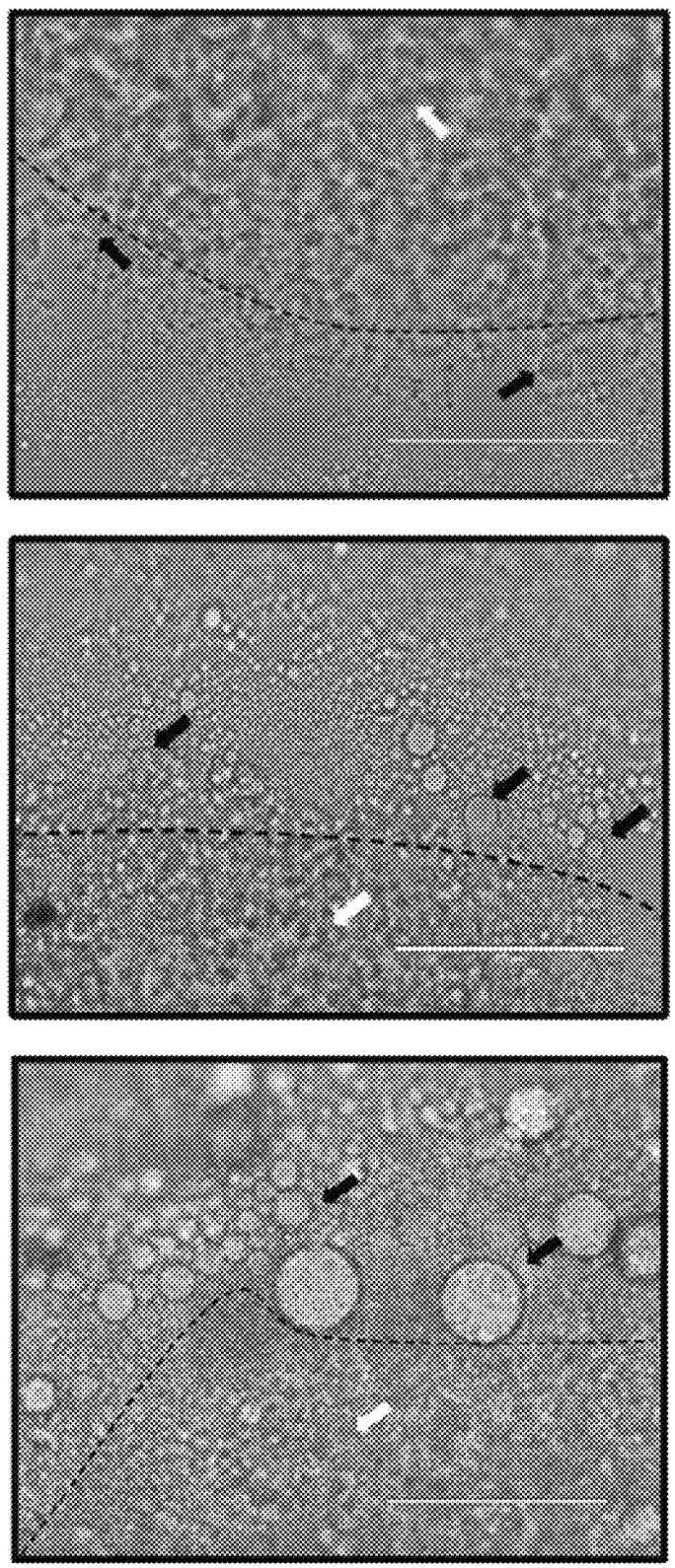
FIG. 12 includes representative bright field images of encapsulated spheroids, in accordance with the present disclosure.

FIG. 12 includes representative bright field images of encapsulated spheroids with 0.15 mg/mL (top), 0.75 mg/mL (middle), and 1.5 mg/mL dilutions of quarternized aminoglycoside antibiotic-derived hydrogel beads. T-47D spheroids (initially plated at 30,000 cells per well) are marked by a black dotted boundary. White arrows indicate the region of spheroids and the black arrow indicate the region of the quarternized aminoglycoside antibiotic-derived hydrogel beads (objective=20×; scale bar is 200 μm).

FIG. 13A is a representative bright field image demonstrating an encapsulated spheroid of T-47D cells. T-47D cells were cultured with an initial cell density of 30,000 cells per well. Aminoglycoside antibiotic-derived hydrogel beads were added to the culture in a concentration of 1.5 mg/mL. The encapsulation layer is outlined in yellow and free space outside the spheroid is represented by white arrows. FIG. 13B includes representative bright field (left; 4×, scale bar is 1000 μm) and phase-contrast (right; 4×, scale bar is 1000 μm) images of encapsulated spheroids cultured in 0.15 mg/mL quarternized aminoglycoside antibiotic-derived hydrogel beads. FIG. 13C includes representative bright field (left; 4×, scale bar is 1000 μm) and phase-contrast (right; 4×, scale bar is 1000 μm) images of encapsulated spheroids cultured in 0.75 mg/mL quarternized aminoglycoside antibiotic-derived hydrogel beads. FIG. 13D includes representative bright field (left; 4×, scale bar is 1000 μm) and phase-contrast (right; 4×, scale bar is 1000 μm) images of encapsulated spheroids cultured in 1.5 mg/mL quarternized aminoglycoside antibiotic-derived hydrogel beads.

Figure 14:
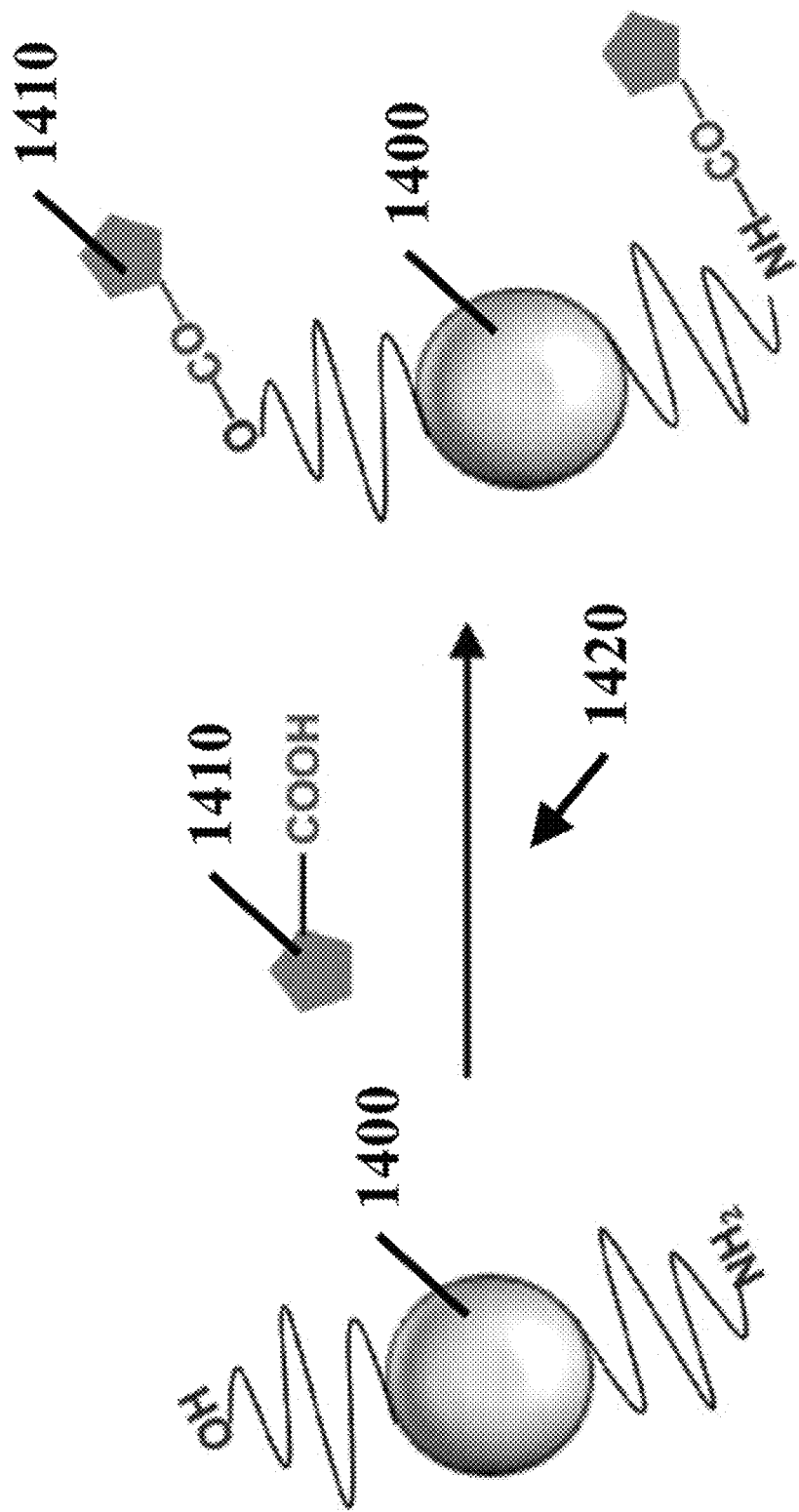
FIG. 14 illustrates an embodiment of a method of conjugating at least one aminoglycoside antibiotic-derived hydrogel beads with an additional molecule, in accordance with the present disclosure.

FIG. 14 illustrates an embodiment of a method of conjugating at least one aminoglycoside antibiotic-derived hydrogel bead 1400 with an additional molecule 1410.

Figure 15A:
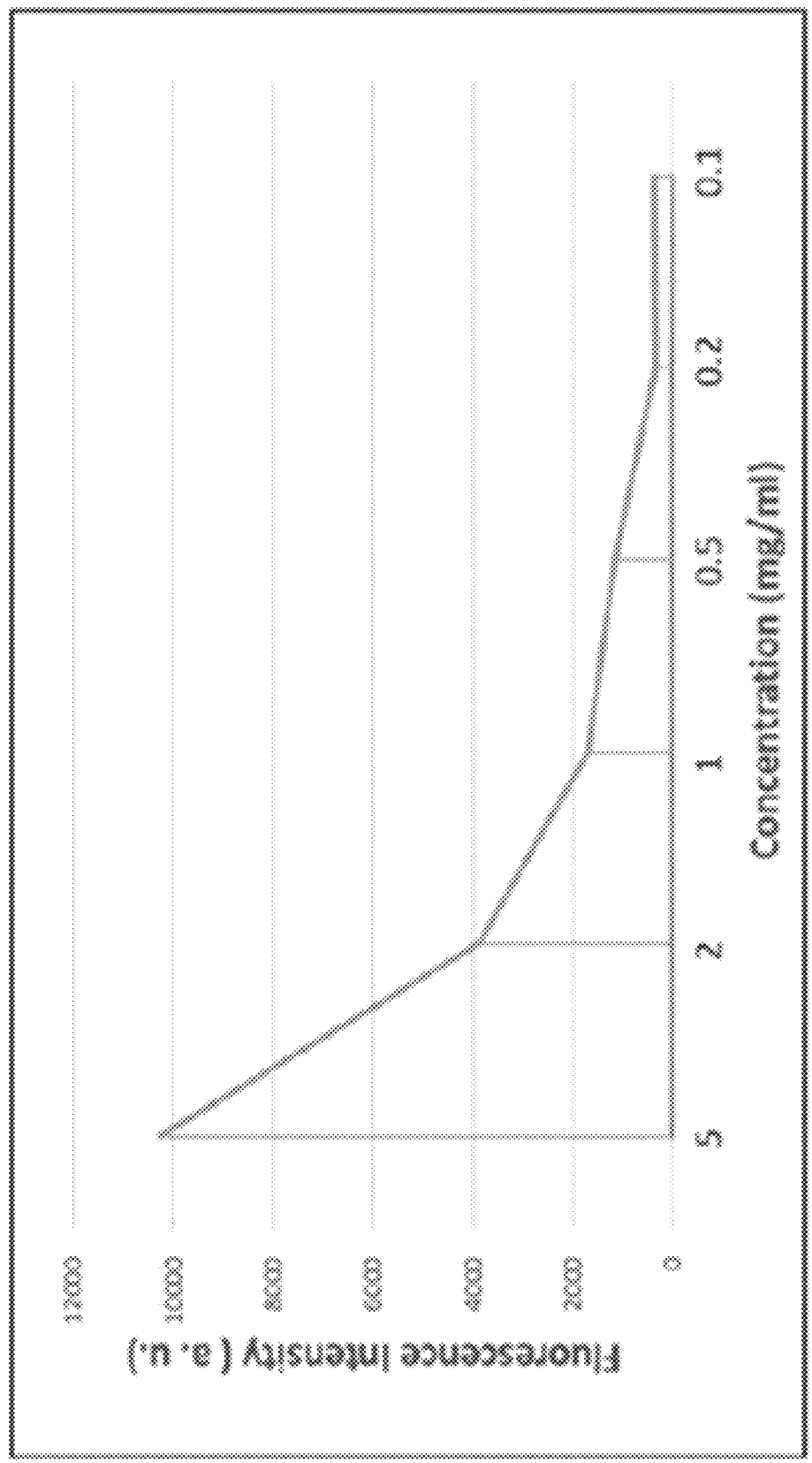
FIG. 15A depicts the fluorescence intensity of serial dilutions of fluorescein-conjugated aminoglycoside antibiotic-derived hydrogel beads using a high concentration of fluorescein conjugation, in accordance with the present disclosure.
Figure 15B:
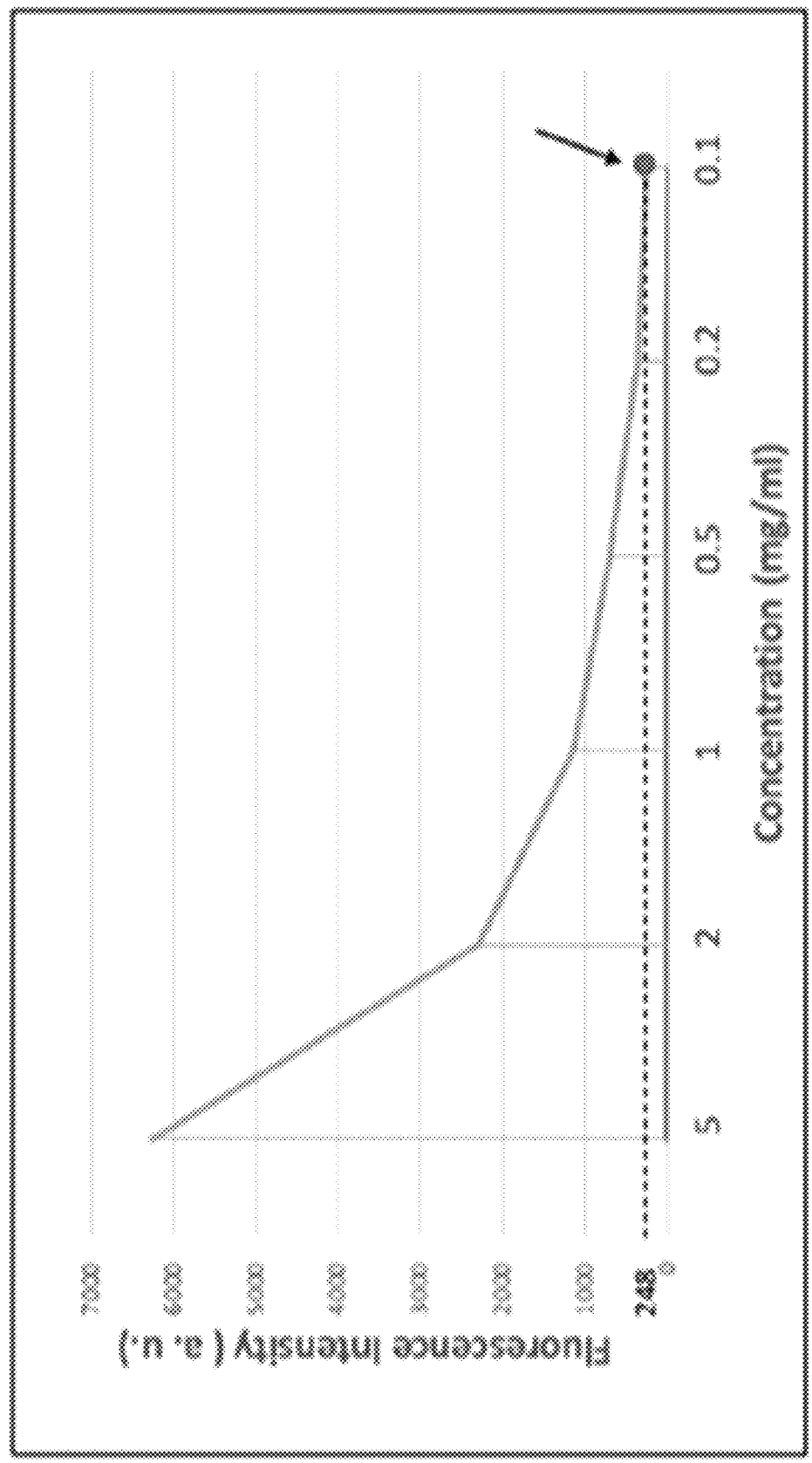
FIG. 15B depicts the fluorescence intensity of serial dilutions of fluorescein-conjugated aminoglycoside antibiotic-derived hydrogel beads using a low concentration of fluorescein conjugation, in accordance with the present disclosure.
Figure 15C:
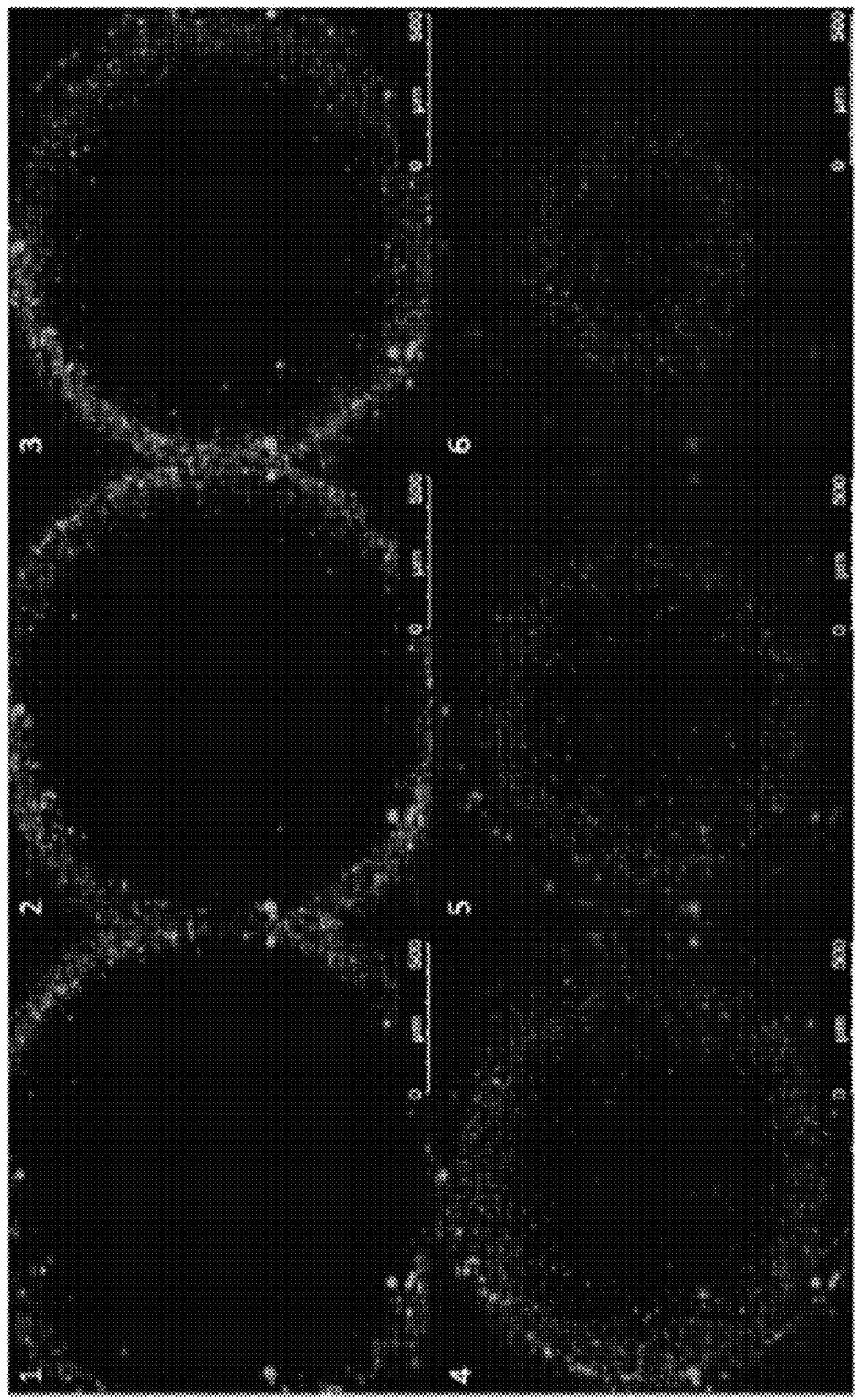
FIG. 15C depicts representative confocal images of an encapsulated spheroid, in accordance with the present disclosure.

FIG. 15A depicts the fluorescence intensity of serial dilutions of fluorescein-conjugated aminoglycoside antibiotic-derived hydrogel beads using a high concentration of fluorescein conjugation. FIG. 15B depicts the fluorescence intensity of serial dilutions of fluorescein-conjugated aminoglycoside antibiotic-derived hydrogel beads using a low concentration of fluorescein conjugation. Optimum intensity was observed at 248 a.u. FIG. 15C are representative confocal images of an encapsulated spheroid of A375 cells (initial cell density of 30,000 cells per well). Spheroids were encapsulated in 0.1 mg/mL of low concentration fluorescein conjugation aminoglycoside antibiotic-derived hydrogel beads. The images represent six sections of 5 μm each from the middle of the spheroid (top left) to the bottom of the spheroid (bottom right). The images demonstrate that the spheroid is completely encapsulated with fluorescein-conjugated aminoglycoside antibiotic-derived hydrogel beads (green), as evidenced by strong fluorescent signal. Objective=10×, scale bar is 500 μm.

Figure 16A:
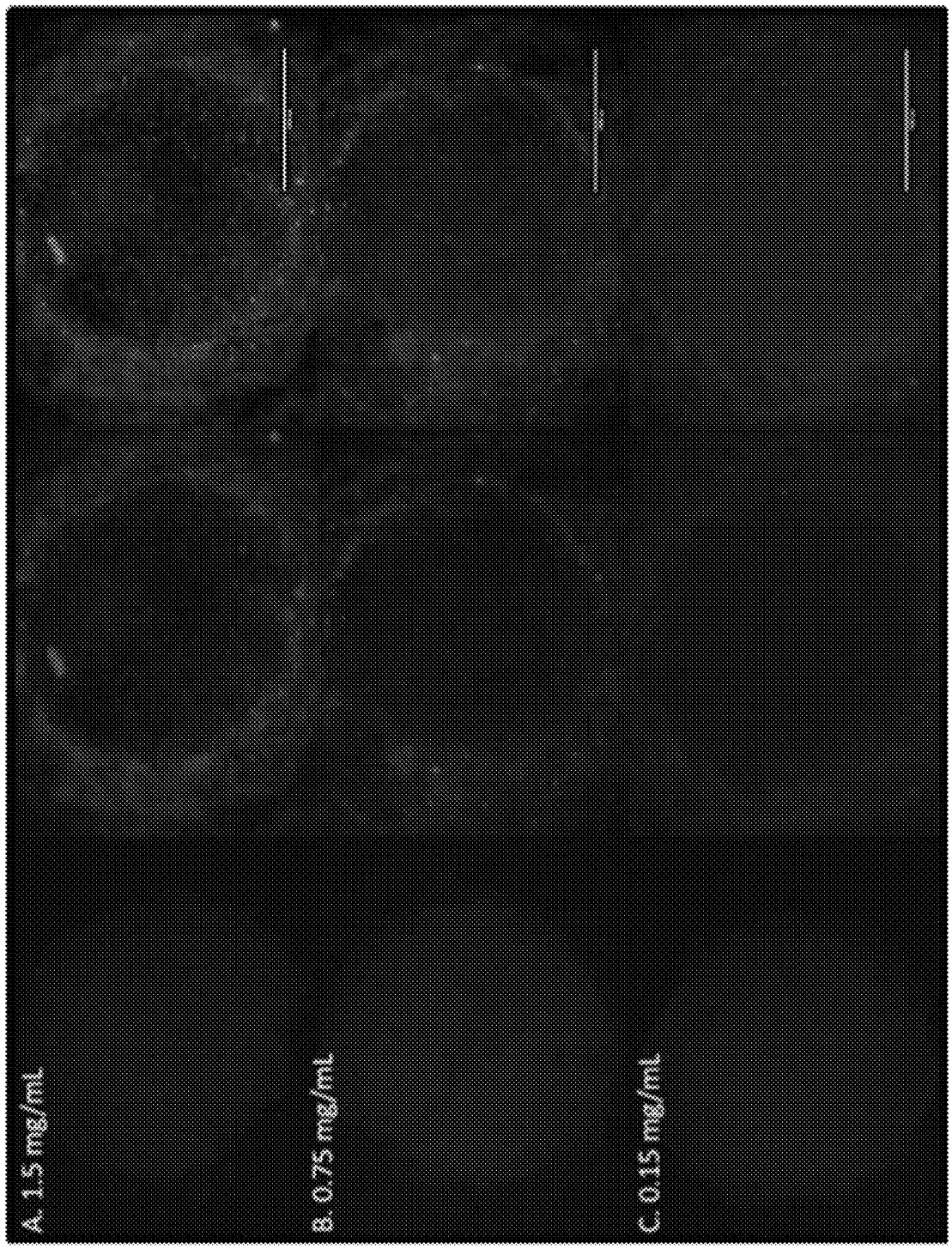
FIG. 16A are representative fluorescence images of an encapsulated spheroid, in accordance with the present disclosure.
Figure 16B:
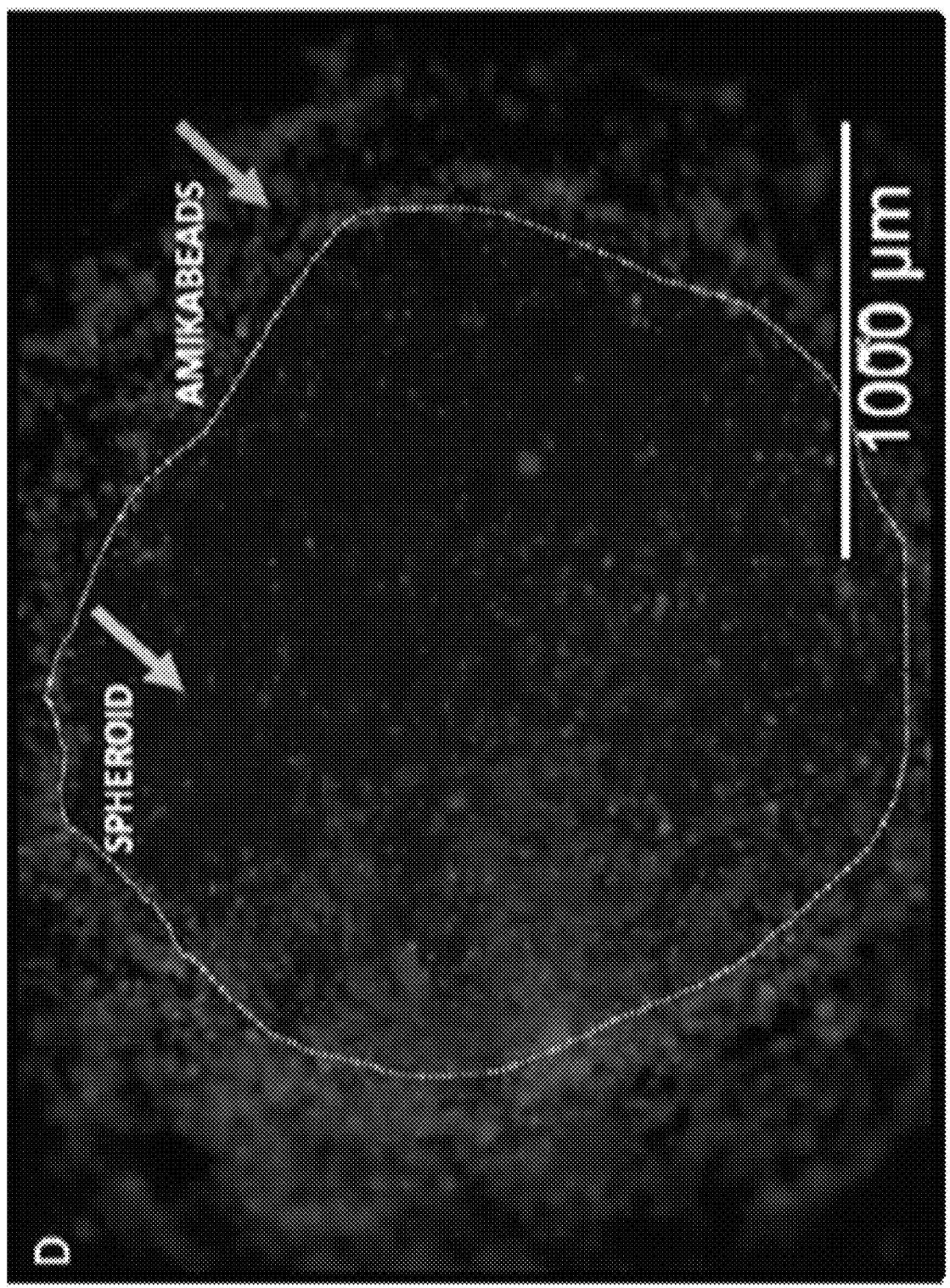
FIG. 16B is a representative fluorescence image of an encapsulated spheroid, in accordance with the present disclosure.

FIG. 16A are representative fluorescence images of an encapsulated spheroid. The spheroid comprises T-47D cells (initial cell density=30,000 cells per well) and is encapsulated with Rho-conjugated aminoglycoside antibiotic-derived hydrogel beads. Encapsulated spheroids were visualized on a polystyrene 96 wells cell culture plate with a standard 10× objective at a depth of approximately 100 μm. T-47D cells were stained with 5 μL DAPI (blue) per well and were encapsulated in a compact layer of Rho-conjugated aminoglycoside antibiotic-derived hydrogel beads at a concentration of 1.5 mg/mL (top), 0.75 mg/mL (middle), and 0.15 mg/mL (bottom). Scale bar is 1000 μm. FIG. 16B is a representative fluorescence image of an encapsulated spheroid demonstrating a distinctive boundary (white dots) between the spheroid comprising T-47D cells (blue arrow) encapsulated in 0.75 mg/mL Rho-conjugated aminoglycoside antibiotic-derived hydrogel beads (red arrow). Scale bar is 1000 μm.

Figure 17:
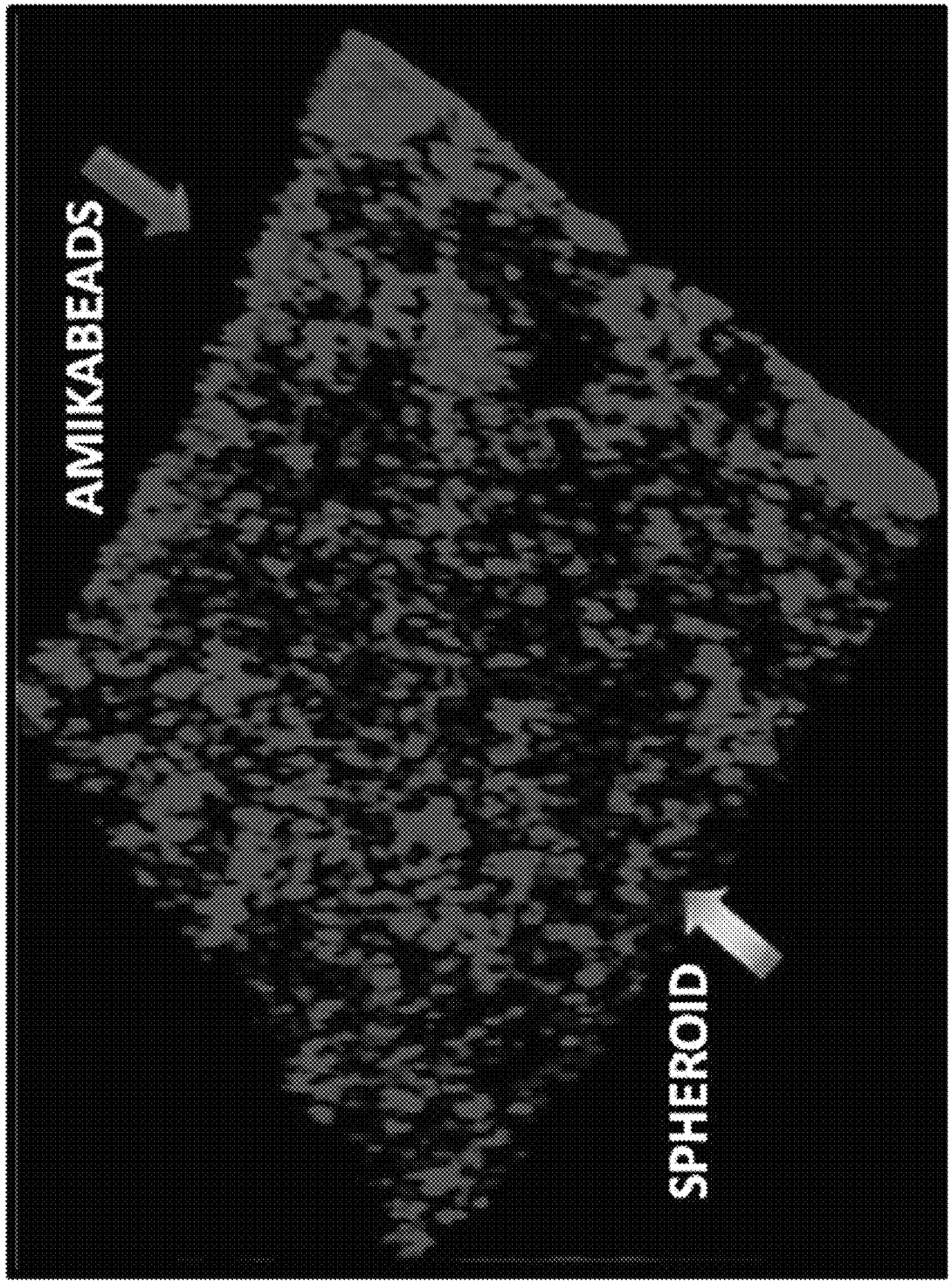
FIG. 17 is a representative image of an encapsulated spheroid, in accordance with the present disclosure.

FIG. 17 is a representative image of an encapsulated spheroid. A z-stack of a spheroid comprising T-47D cells (initial density=30,000 cells per well) were stained with 5 DAPI (blue) per well in 0.75 mg/mL of Rho-conjugated aminoglycoside antibiotic-derived hydrogel beads and imaged using a Light Sheet Confocal Microscope.

Figure 18:
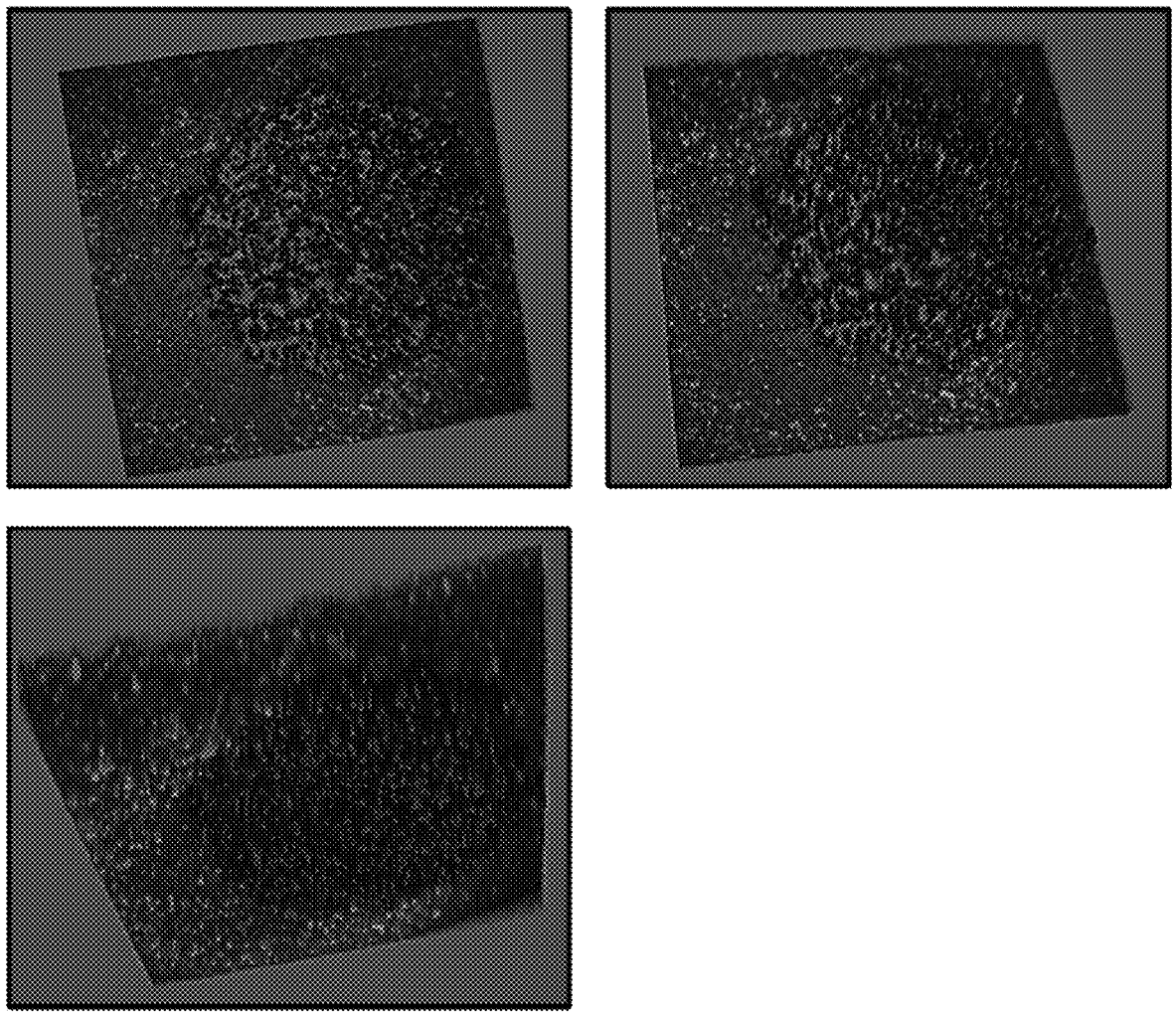
FIG. 18 includes representative z-stack projections of encapsulated spheroids comprising T-47D cells encapsulated with Rho-conjugated aminoglycoside antibiotic-derived hydrogel beads, in accordance with the present disclosure.

FIG. 18 includes representative z-stack projections of encapsulated spheroids comprising T-47D cells encapsulated with Rho-conjugated aminoglycoside antibiotic-derived hydrogel beads. Three-dimensional projections of z-stacks of confocal microscopy images captured from a T-47D spheroid stained with DAPI (blue) encapsulated in 0.75 mg/mL Rho-conjugated aminoglycoside antibiotic-derived hydrogel beads (red).

Figure 19:
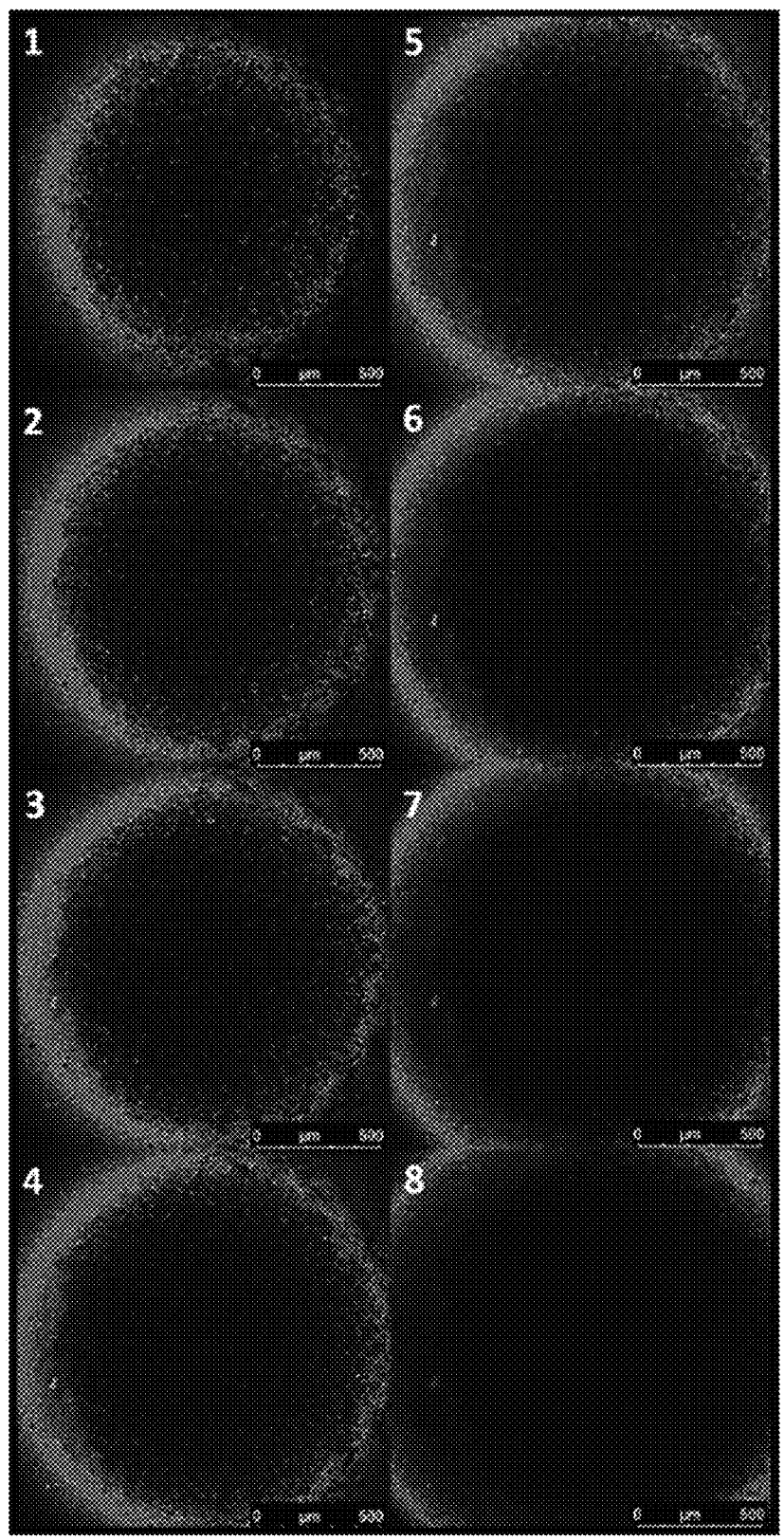
FIG. 19 includes representative images of an encapsulated spheroid, in accordance with the present disclosure.

FIG. 19 includes representative images of an encapsulated spheroid. Spheroids comprising A375 cells (initial cell density=30,000 cells/well) were encapsulated with Rho-conjugated aminoglycoside antibiotic-derived hydrogel beads (0.75 mg/mL) and were stained with Hoechst 33342 to visualize the nucleus. Images were acquired using a laser scanning confocal microscope and 10× objective with a zoom of 0.75. The images illustrate eight sections of 5 μm each from the bottom of the spheroid (1) to the middle of the spheroid (8). The prominent spherical boundary between spheroid (blue) and the Rho-conjugated aminoglycoside antibiotic-derived hydrogel bead layer (red) attests to the overall coverage of the aminoglycoside antibiotic-derived hydrogel beads around the spheroid. Scale bar is 500 μm.

Figure 20:
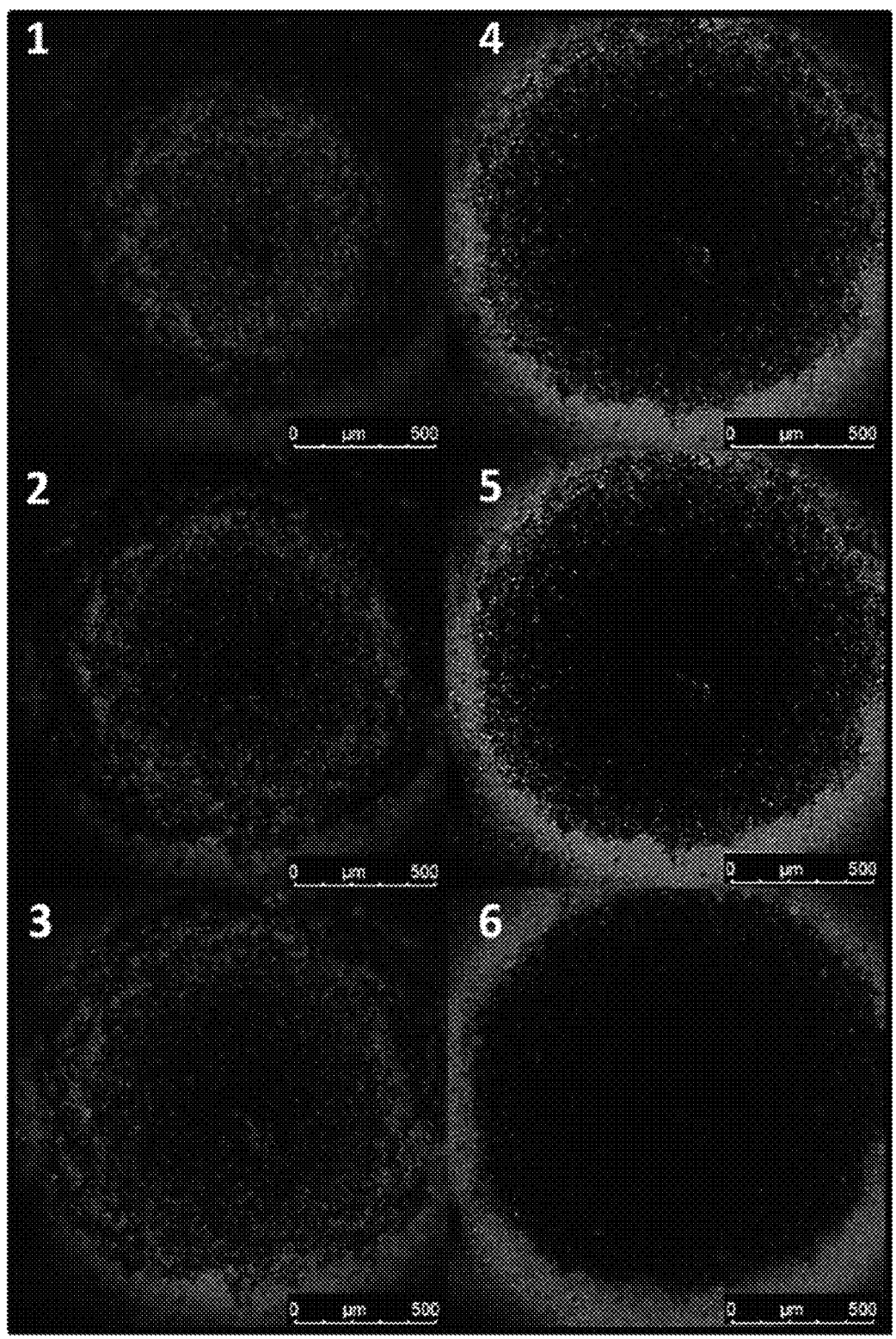
FIG. 20 includes representative images of an encapsulated spheroid, in accordance with the present disclosure.

FIG. 20 includes representative images of an encapsulated spheroid. Spheroids comprising A375 cells (initial cell density=30,000 cells/well) were encapsulated with Rho-conjugated aminoglycoside antibiotic-derived hydrogel beads (0.15 mg/mL) and were stained with Hoechst 33342 to visualize the nucleus. Images were acquired using a laser scanning confocal microscope and 10× objective with a zoom of 0.75. The images illustrate six sections of 5 μm each from the bottom of the spheroid (1) to the middle of the spheroid (6). The prominent spherical boundary between spheroid (blue) and the Rho-conjugated aminoglycoside antibiotic-derived hydrogel bead layer (red) attests to the overall coverage of the aminoglycoside antibiotic-derived hydrogel beads around the spheroid. Scale bar is 500 μm.

Figure 21:
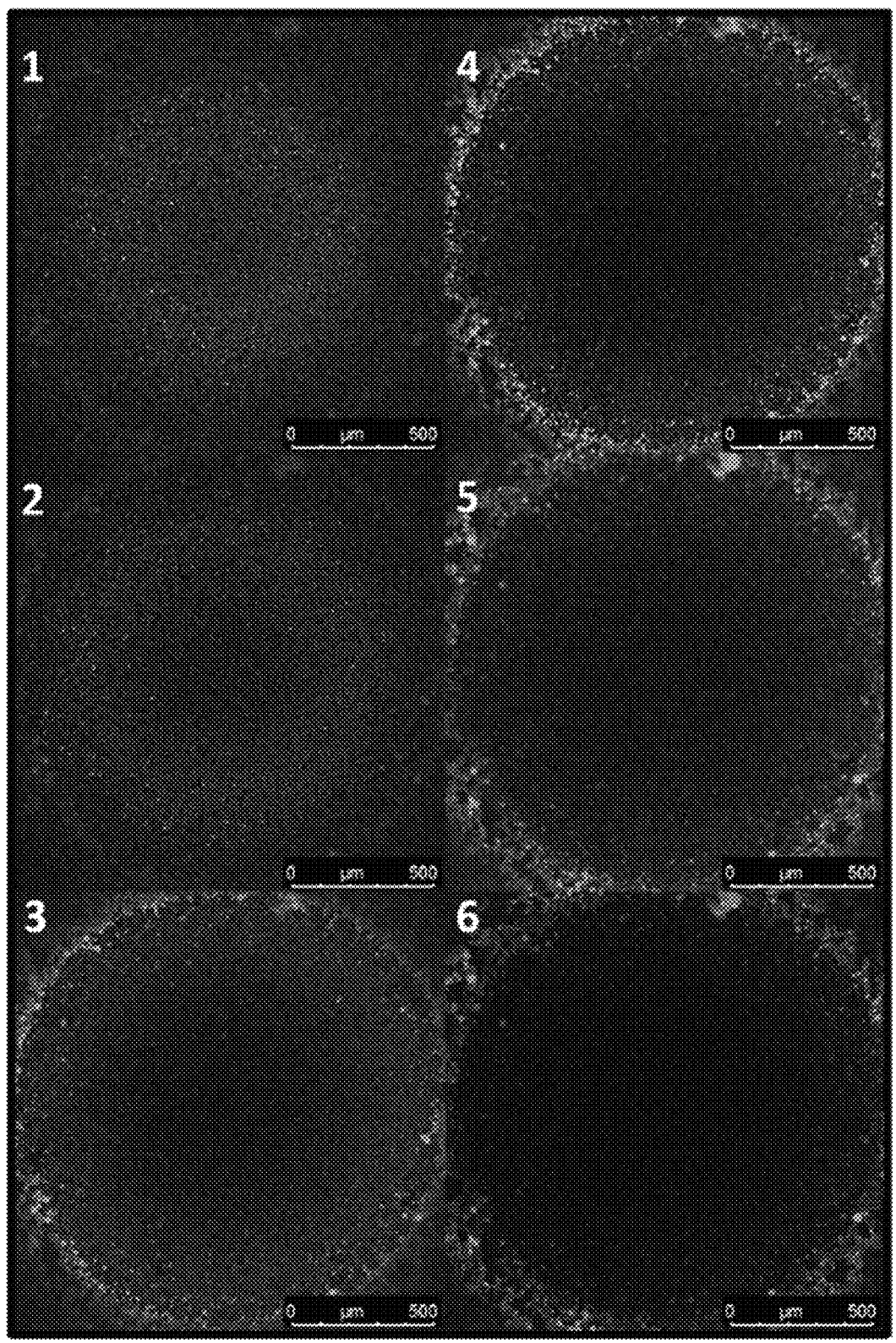
FIG. 21 includes representative images of an encapsulated spheroid, in accordance with the present disclosure.

FIG. 21 includes representative images of an encapsulated spheroid. Spheroids comprising A375 cells (initial cell density=30,000 cells/well) were encapsulated with Fluorescein-conjugated aminoglycoside antibiotic-derived hydrogel beads (0.1 mg/mL) and were stained with DRAQ5TM to visualize the nucleus. Images were acquired using a laser scanning confocal microscope and 10× objective with a zoom of 0.75. The images illustrate six sections of 5 μm each from the bottom of the spheroid (1) to the middle of the spheroid (6). The prominent spherical boundary between spheroid (red) and the Rho-conjugated aminoglycoside antibiotic-derived hydrogel bead layer (green) attests to the overall coverage of the aminoglycoside antibiotic-derived hydrogel beads around the spheroid. Scale bar is 500 μm.

Figure 22B:
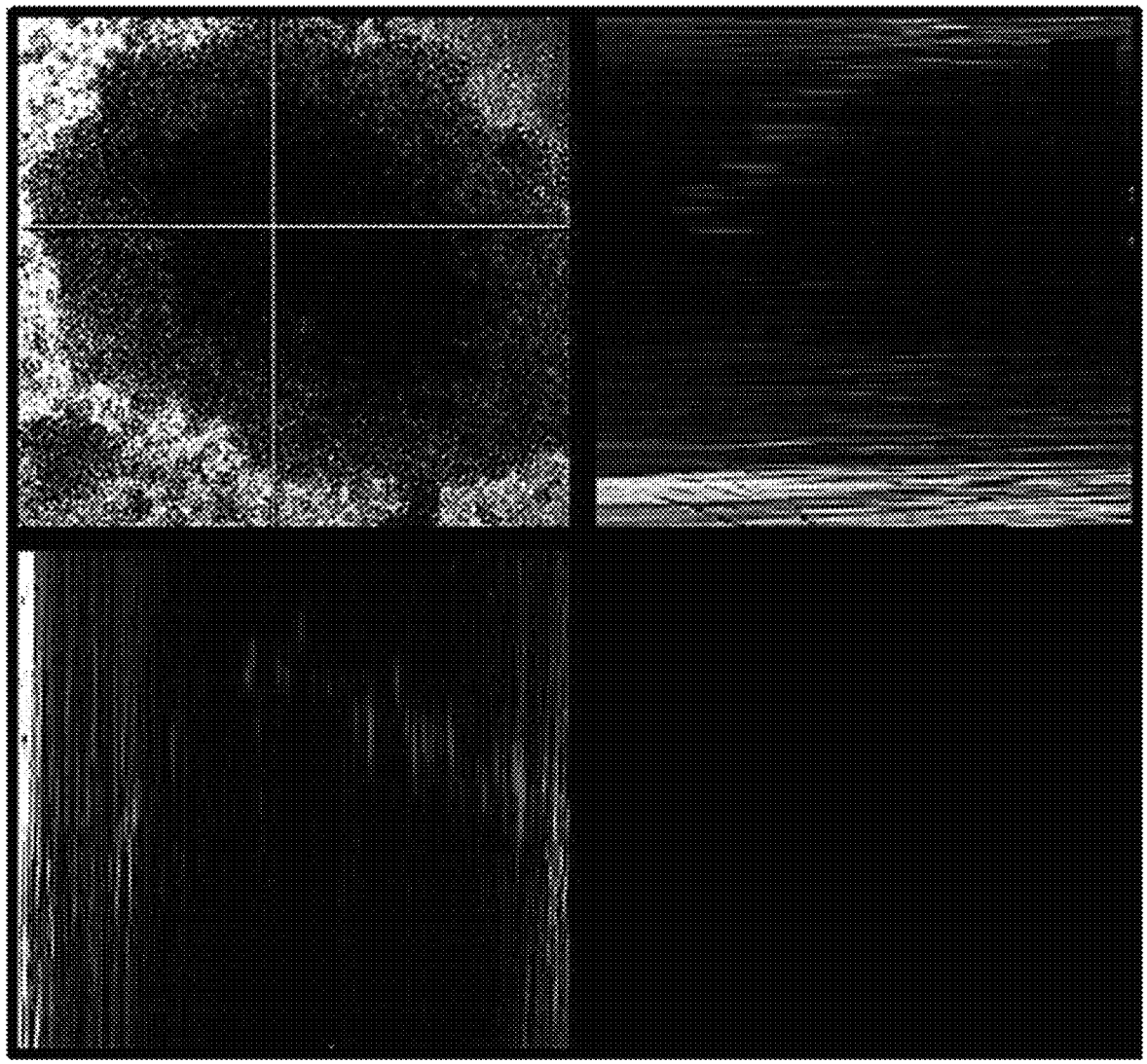
FIG. 22B includes representative images of an encapsulated spheroid, in accordance with the present disclosure.

FIG. 22A includes representative images of an encapsulated spheroid. Spheroids comprising A375 cells were encapsulated with Rho-conjugated aminoglycoside antibiotic-derived hydrogel beads. A bright field image (left) and a confocal microscopy image (right) demonstrate the encapsulation of an A375 spheroid (dark in 0.75 mg/mL Rho-conjugated aminoglycoside antibiotic-derived hydrogel beads (red) using a 10× objective dipping lens. FIG. 22B are representative images of an encapsulated spheroid. A bright field image (left) and a confocal microscopy image (right) using vertical sectioning demonstrate streaks corresponding to the Rho-conjugated aminoglycoside antibiotic-derived hydrogel beads on the surface of the spheroid. Scale bar is 500 μm.

Figure 23A:
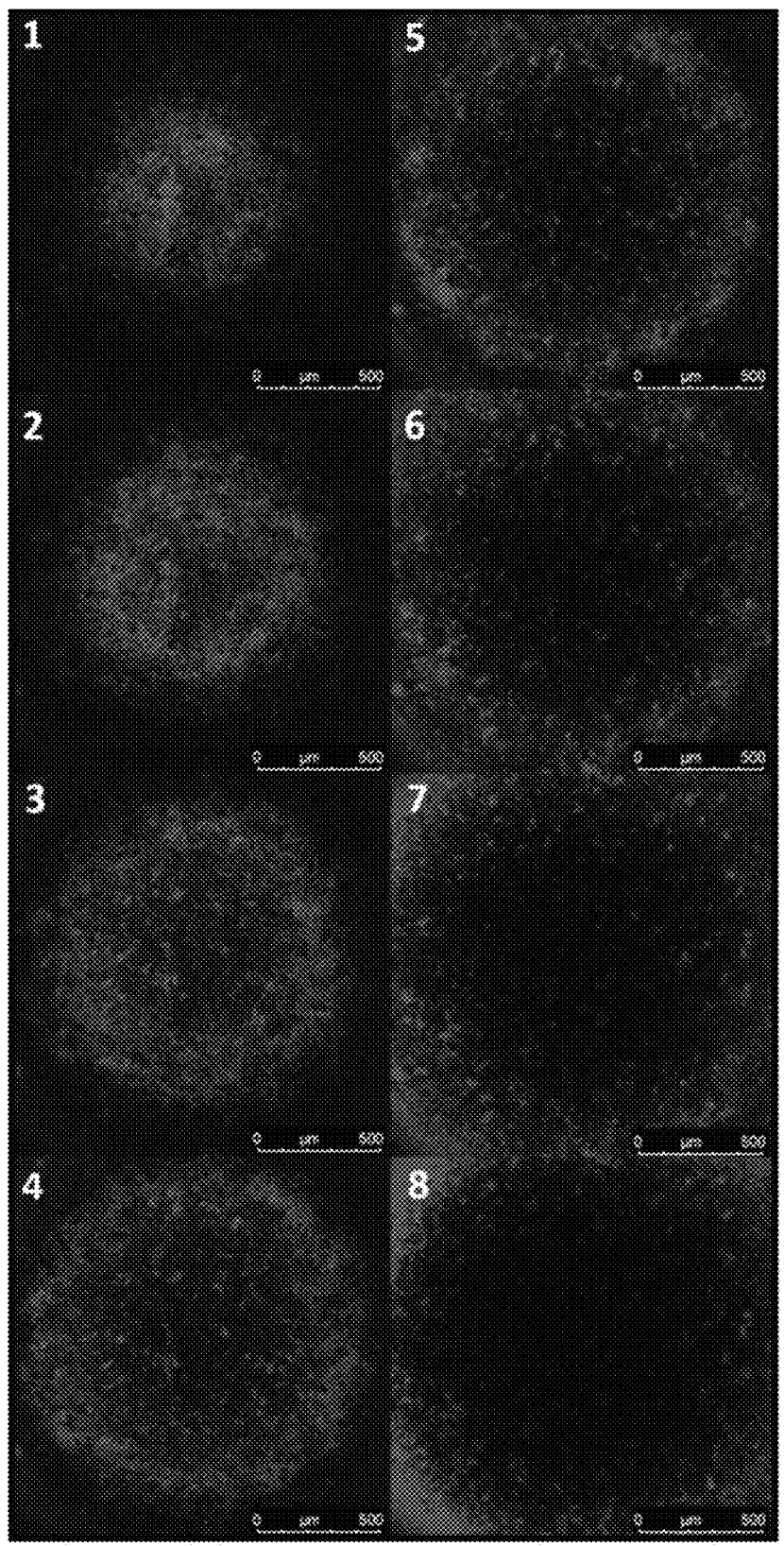
FIG. 23A includes representative images of an encapsulated spheroid, in accordance with the present disclosure.
Figure 23B:
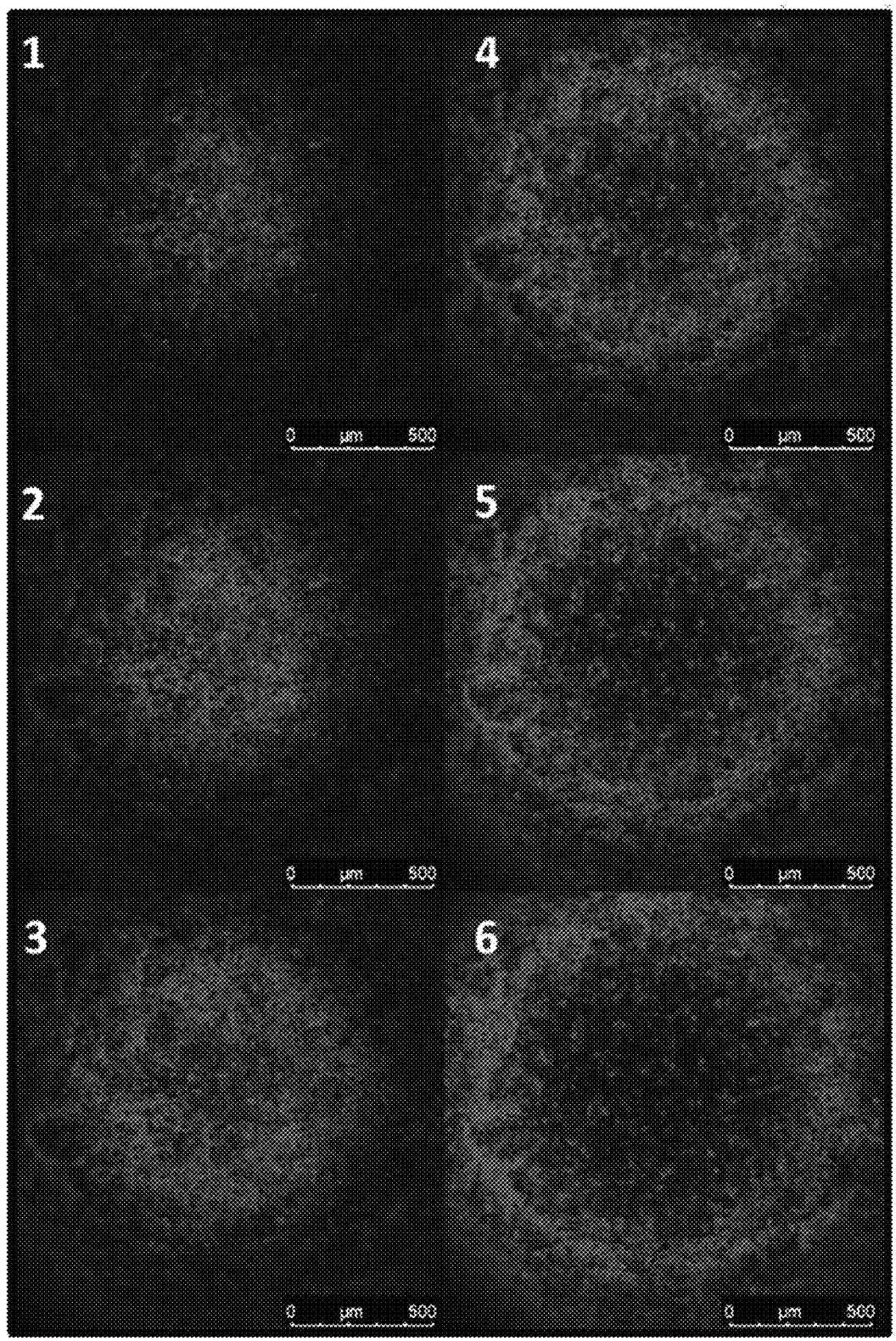
FIG. 23B includes representative images of an encapsulated spheroid, in accordance with the present disclosure.

FIG. 23A includes representative images of an encapsulated spheroid. Spheroids comprising hMSC cells (initial cell density=30,000 cells per well; AM7) were encapsulated by Rho-conjugated aminoglycoside antibiotic-derived hydrogel beads (0.75 mg/mL) and were stained with Hoechst 33342 to visualize the nucleus. Images were acquired using a laser scanning confocal microscope and 10× objective with a zoom of 0.75. The images illustrate eight sections of 5 μm each from the bottom of the spheroid (1) to the middle of the spheroid (8). The prominent spherical boundary between spheroid (blue) and the Rho-conjugated aminoglycoside antibiotic-derived hydrogel bead layer (red) attests to the overall coverage of the aminoglycoside antibiotic-derived hydrogel beads around the spheroid. Scale bar is 500 μm. FIG. 23B are representative images of an encapsulated spheroid. Spheroids comprising hMSC cells (initial cell density=30,000 cells per well; AM6) were encapsulated by Rho-conjugated aminoglycoside antibiotic-derived hydrogel beads (0.75 mg/mL) and were stained with Hoechst 33342 to visualize the nucleus. Images were acquired using a laser scanning confocal microscope and 10× objective with a zoom of 0.75. The images illustrate six sections of 5 μm each from the bottom of the spheroid (1) to the middle of the spheroid (6). The prominent spherical boundary between spheroid (blue) and the Rho-conjugated aminoglycoside antibiotic-derived hydrogel bead layer (red) attests to the overall coverage of the aminoglycoside antibiotic-derived hydrogel beads around the spheroid. Scale bar is 500 μm.

Figure 24A:
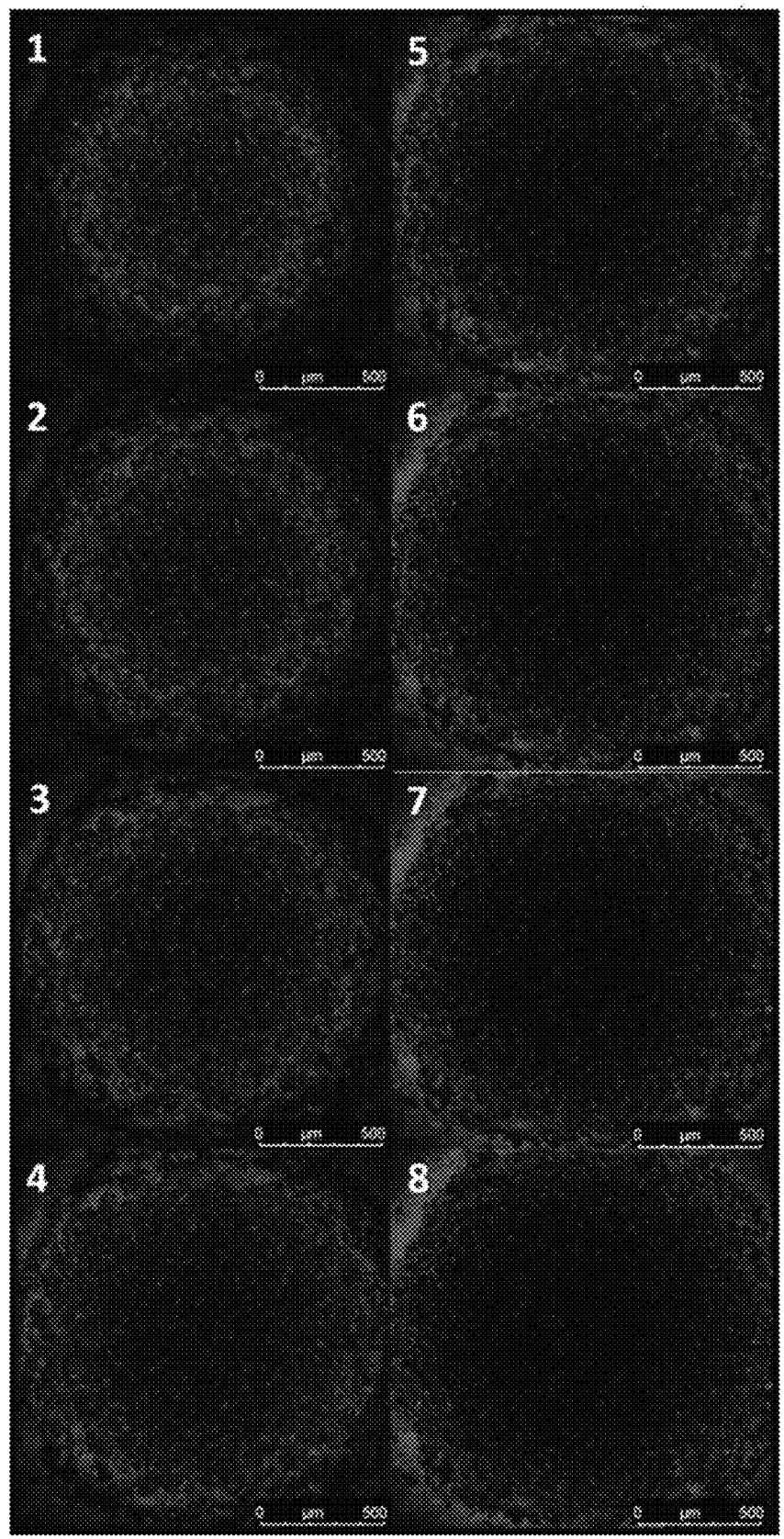
FIG. 24A includes representative images of an encapsulated spheroid, in accordance with the present disclosure.
Figure 24B:
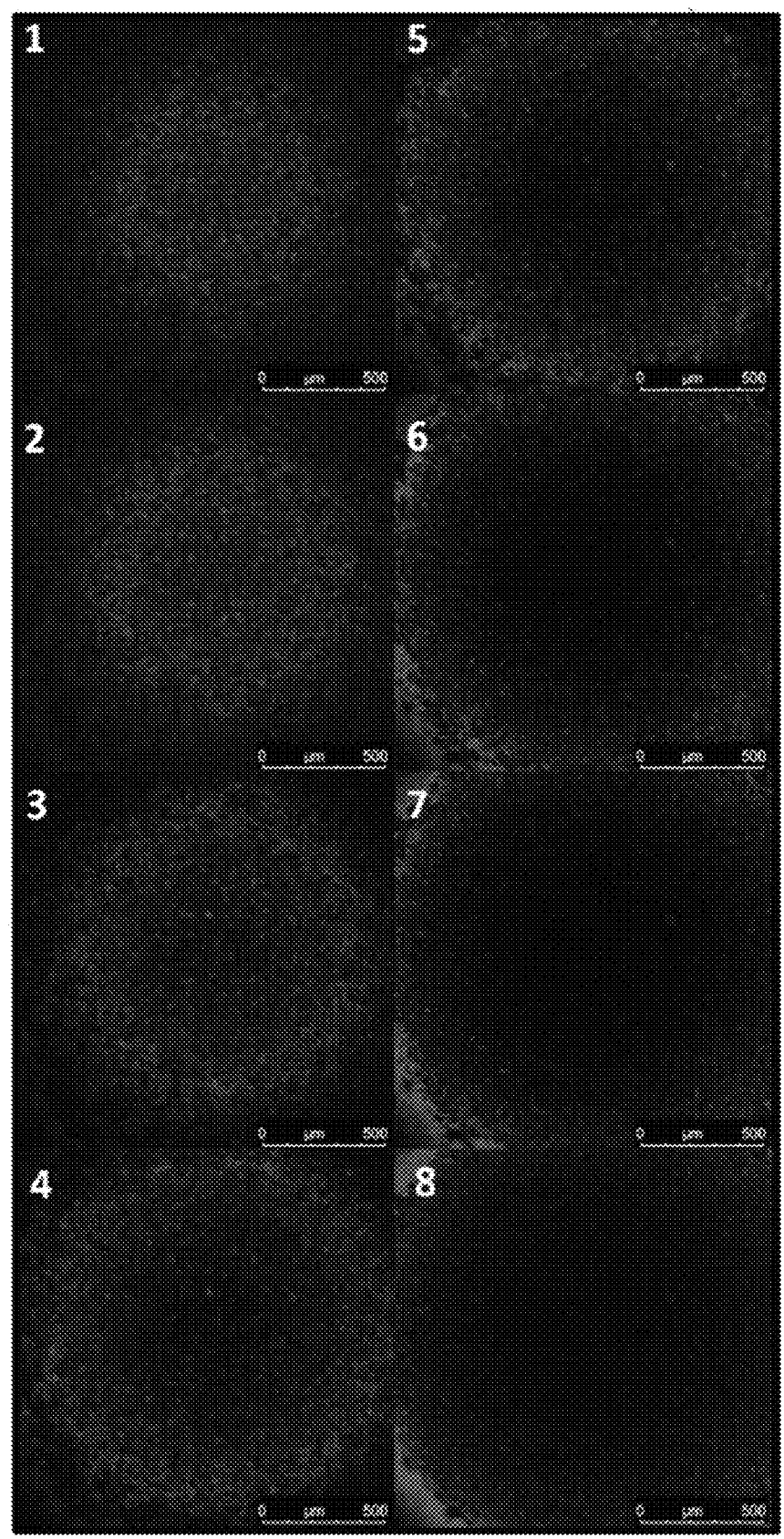
FIG. 24B includes are representative images of an encapsulated spheroid, in accordance with the present disclosure.
Figure 24C:
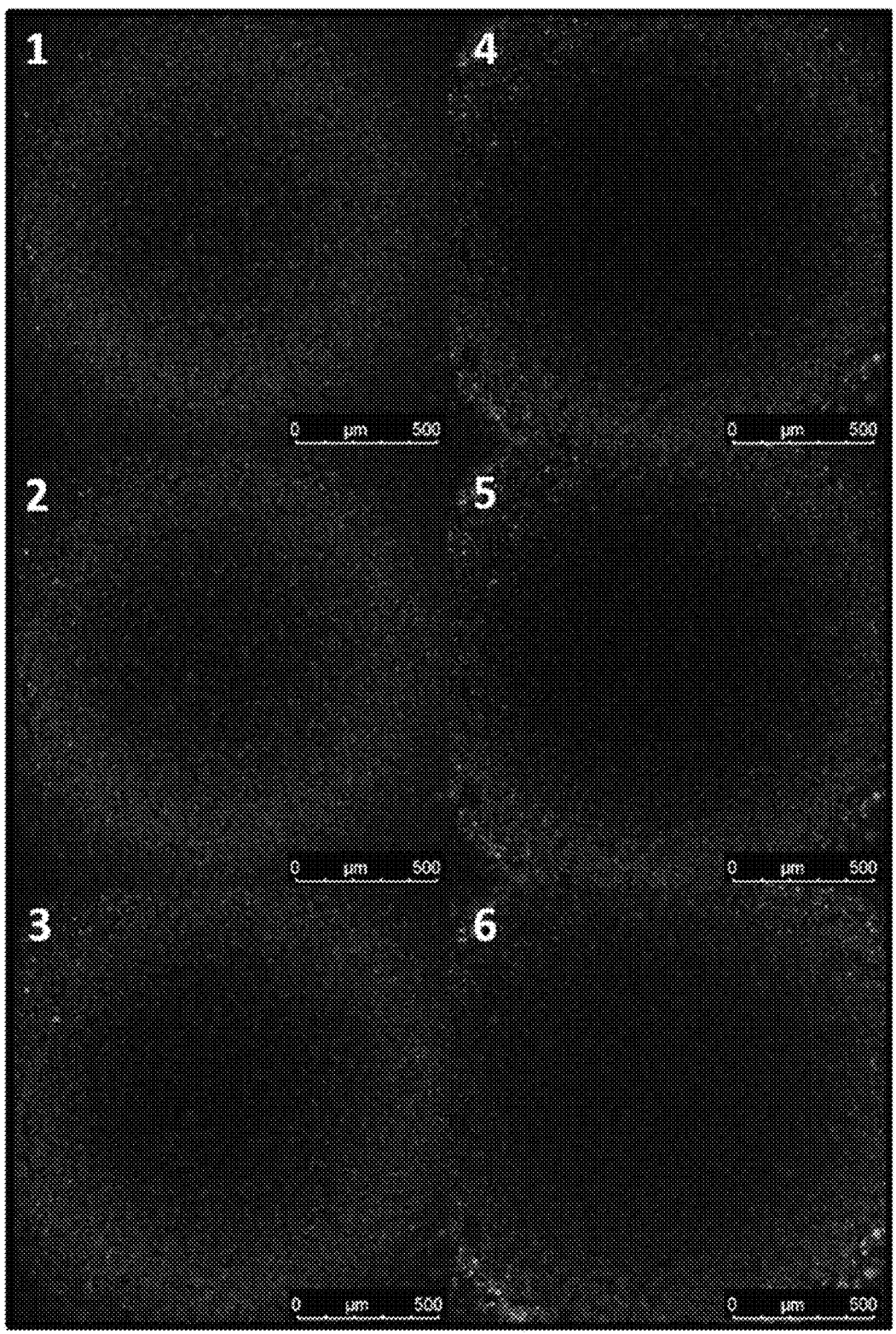
FIG. 24C includes representative images of an encapsulated spheroid, in accordance with the present disclosure.

FIG. 24A includes representative images of an encapsulated spheroid. Spheroids comprising hMSC cells (initial cell density=30,000 cells per well; AM7) were encapsulated by Rho-conjugated aminoglycoside antibiotic-derived hydrogel beads (0.75 mg/mL) and were stained with Hoechst 33342 to visualize the nucleus. Images were acquired using a laser scanning confocal microscope and 10× objective with a zoom of 0.75. The images illustrate six sections of 5 μm each from the bottom of the spheroid (1) to the middle of the spheroid (6). The prominent spherical boundary between spheroid (blue) and the Rho-conjugated aminoglycoside antibiotic-derived hydrogel bead layer (red) attests to the overall coverage of the aminoglycoside antibiotic-derived hydrogel beads around the spheroid. Scale bar is 500 μm. FIG. 24B are representative images of an encapsulated spheroid. Spheroids comprising hMSC cells (initial cell density=30,000 cells per well; AM6) were encapsulated by Rho-conjugated aminoglycoside antibiotic-derived hydrogel beads (0.75 mg/mL) and were stained with Hoechst 33342 to visualize the nucleus. Images were acquired using a laser scanning confocal microscope and 10× objective with a zoom of 0.75. The images illustrate eight sections of 5 μm each from the bottom of the spheroid (1) to the middle of the spheroid (8). The prominent spherical boundary between spheroid (blue) and the Rho-conjugated aminoglycoside antibiotic-derived hydrogel bead layer (red) attests to the overall coverage of the aminoglycoside antibiotic-derived hydrogel beads around the spheroid. Scale bar is 500 μm. FIG. 24C are representative images of an encapsulated spheroid. Spheroids comprising hMSC cells (initial cell density=30,000 cells per well; AM7) were encapsulated by Fluorescein-conjugated aminoglycoside antibiotic-derived hydrogel beads (0.1 mg/mL) and were stained with DRAQ5TM to visualize the nucleus. Images were acquired using a laser scanning confocal microscope and 10× objective with a zoom of 0.75. The images illustrate six sections of 5 μm each from the bottom of the spheroid (1) to the middle of the spheroid (6). The prominent spherical boundary between spheroid (red) and the Fluorescein-conjugated aminoglycoside antibiotic-derived hydrogel bead layer (green) attests to the overall coverage of the aminoglycoside antibiotic-derived hydrogel beads around the spheroid. Scale bar is 500 μm.

Figure 25:
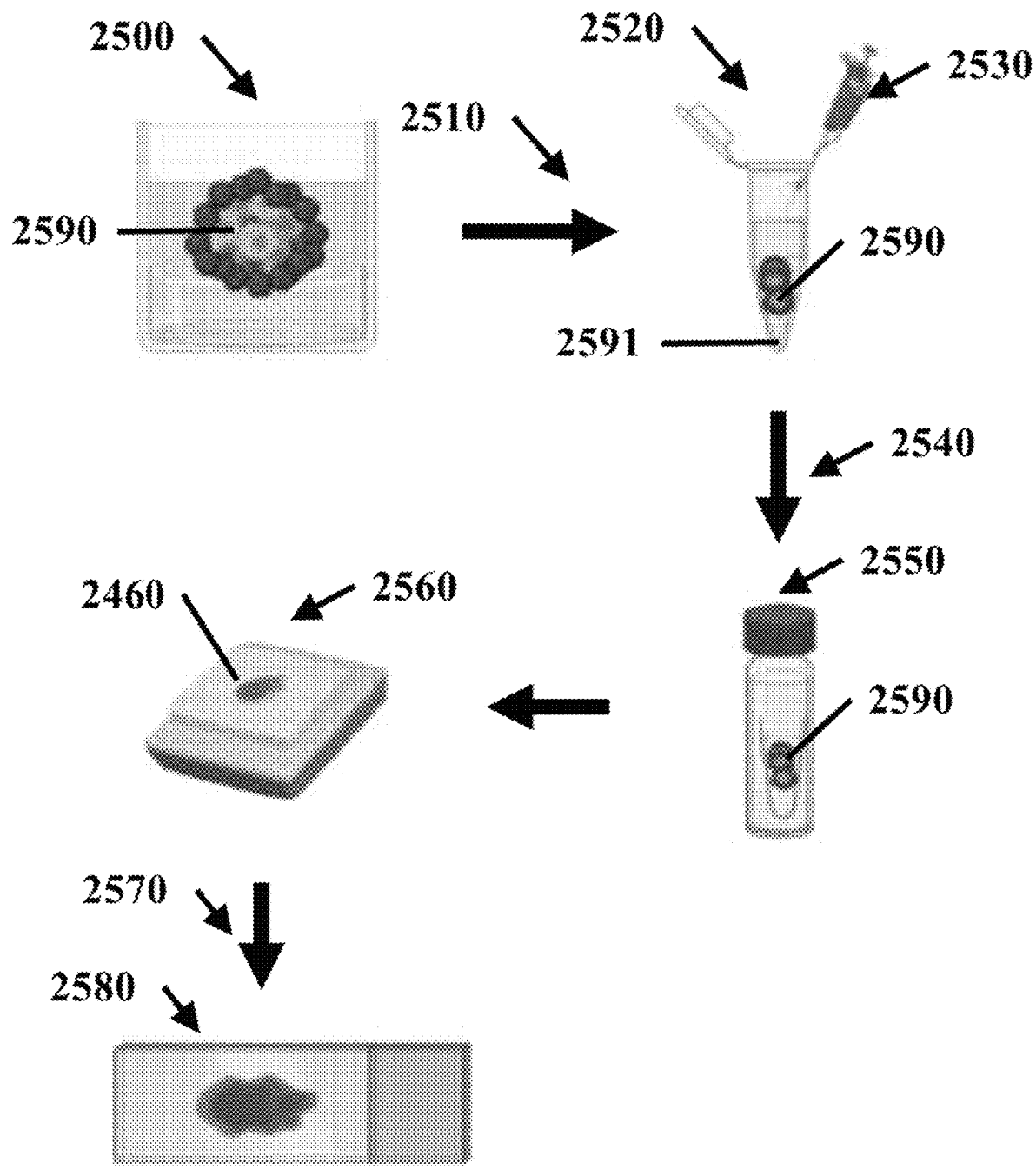
FIG. 25 illustrates an embodiment of a method of generating formalin fixed paraffin embedded encapsulated spheroids, in accordance with the present disclosure.

FIG. 25 illustrates an embodiment of a method of generating formalin fixed paraffin embedded encapsulated spheroids. Encapsulated spheroids 2590 are generated 2500 and fixed 2510 in formalin and transferred 2520 to a microcentrifuge tube 2591. Low melting agarose (2%) is added 2530 to the formalin fixed encapsulated spheroids 2500 and centrifuged 2540 for 1 minute at 100 RPM. Formalin fixed encapsulated spheroids 2590 are dehydrated 2550 using phosphate buffered saline, 20-100% ethanol, xylene, xylene-paraffin, and paraffin. Dehydrated samples are embedded 2560 in paraffin and tissue is sectioned 2570 through a microtome and mounted 2580 on slides for immunocytochemistry.

Figure 26:
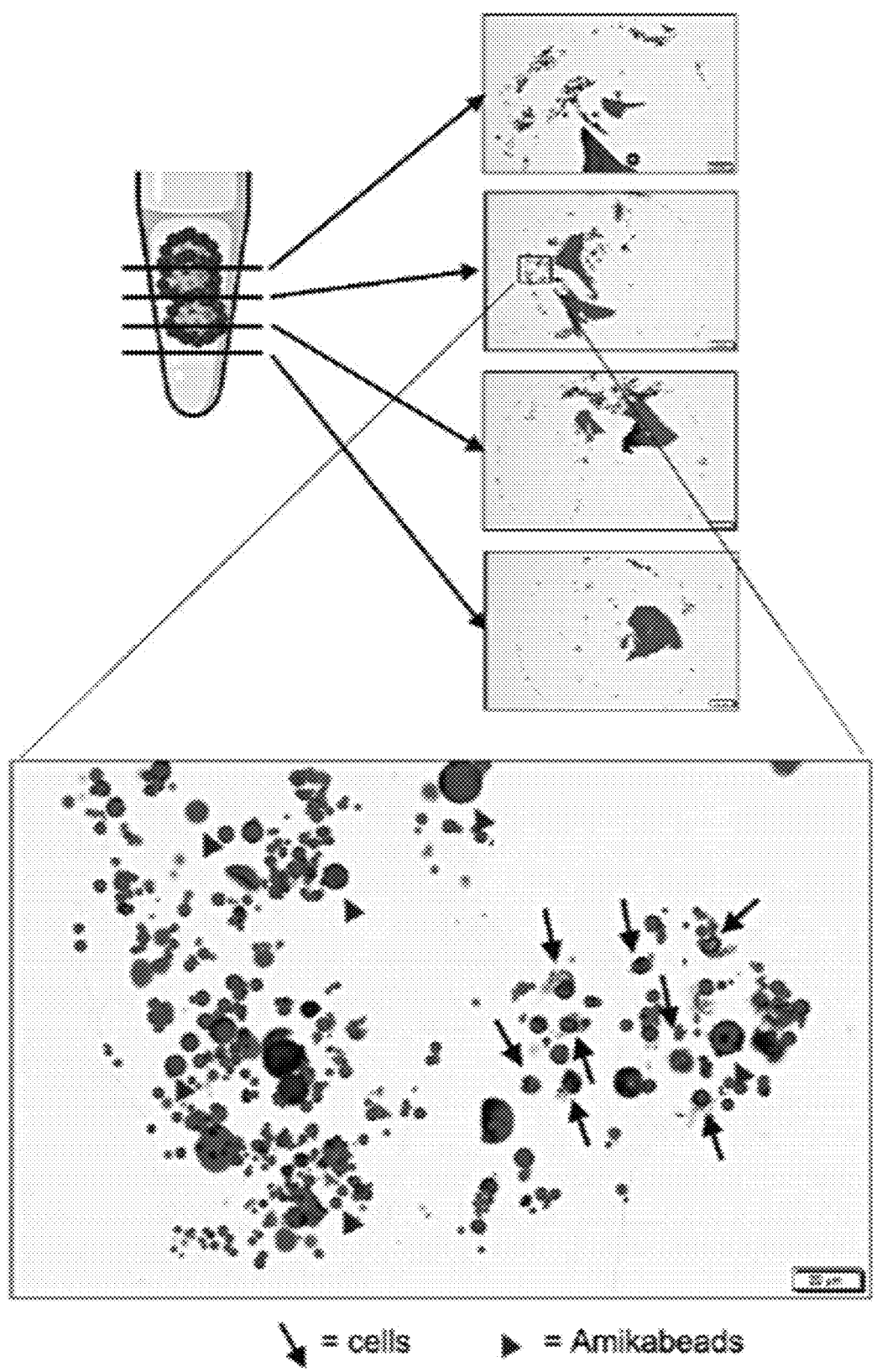
FIG. 26 includes representative images of H&E stained serial sections of fixed encapsulated spheroids, in accordance with the present disclosure.

FIG. 26 includes representative images of H&E stained serial sections of fixed encapsulated spheroids. Encapsulated spheroids (A375 cells, initial cell density=30,000 cells per well) were encapsulated in 0.75 mg/mL of Rho-conjugated aminoglycoside antibiotic-derived hydrogel beads. Rho-conjugated aminoglycoside antibiotic-derived hydrogel beads demonstrate increasing clusters of cells and Rho-conjugated aminoglycoside antibiotic-derived hydrogel beads going deeper into the tissue (objective 20×, scale bar is 500 µm). Cells are marked with black arrowheads.

Figure 27:
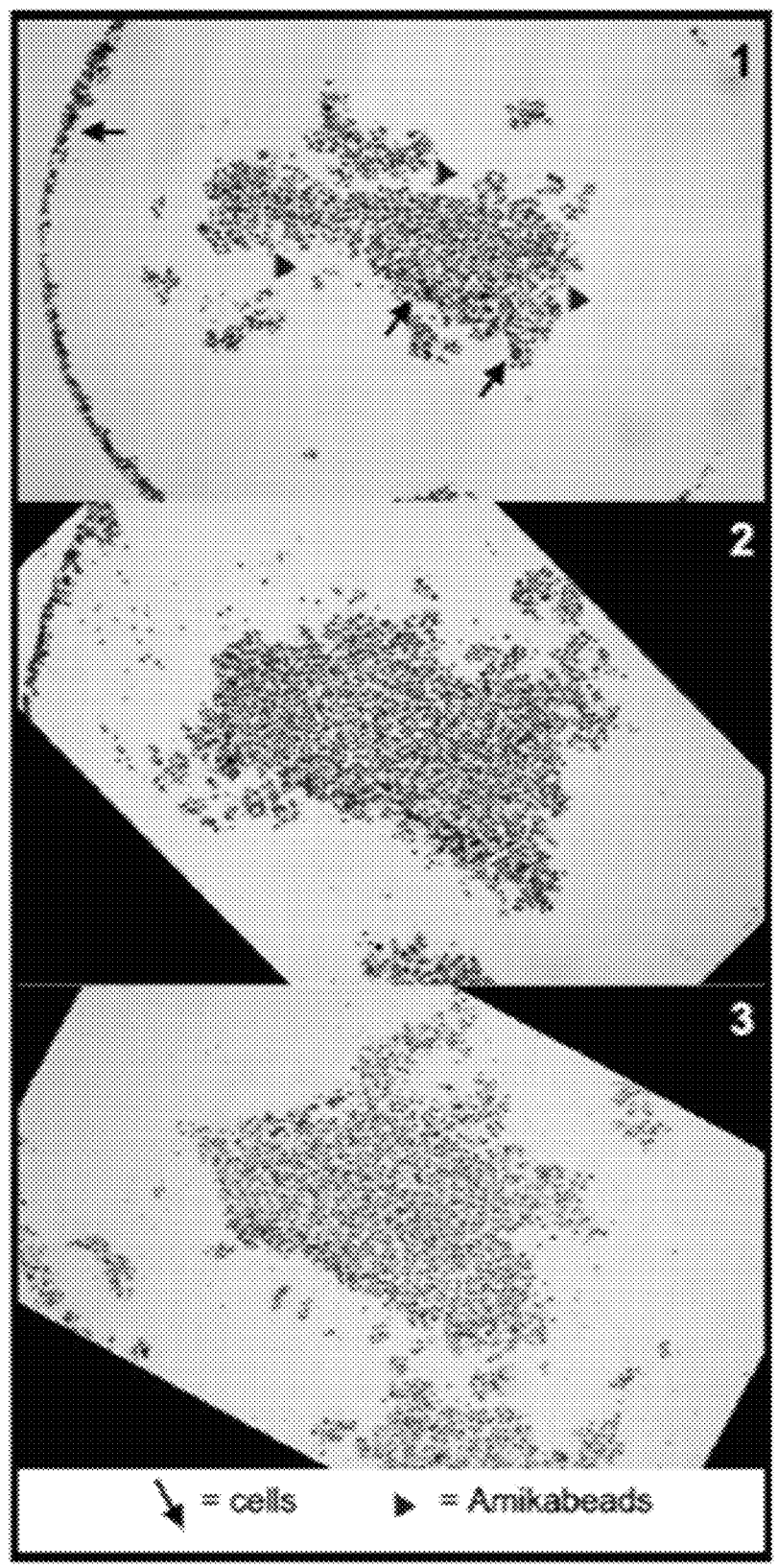
FIG. 27 includes representative images of H&E stained serial sections of fixed encapsulated spheroids, in accordance with the present disclosure.

FIG. 27 includes representative images of H&E stained serial sections of fixed encapsulated spheroids. Encapsulated spheroids (A375 cells, initial cell density=30,000 cells per well) were encapsulated in 0.75 mg/mL of Rho-conjugated aminoglycoside antibiotic-derived hydrogel beads. Rho-conjugated aminoglycoside antibiotic-derived hydrogel beads demonstrate increasing clusters of cells and Rho-conjugated aminoglycoside antibiotic-derived hydrogel beads going deeper into the tissue (objective 20×, scale bar is 500 µm). Cells are marked with black arrowheads.

Figure 28A:
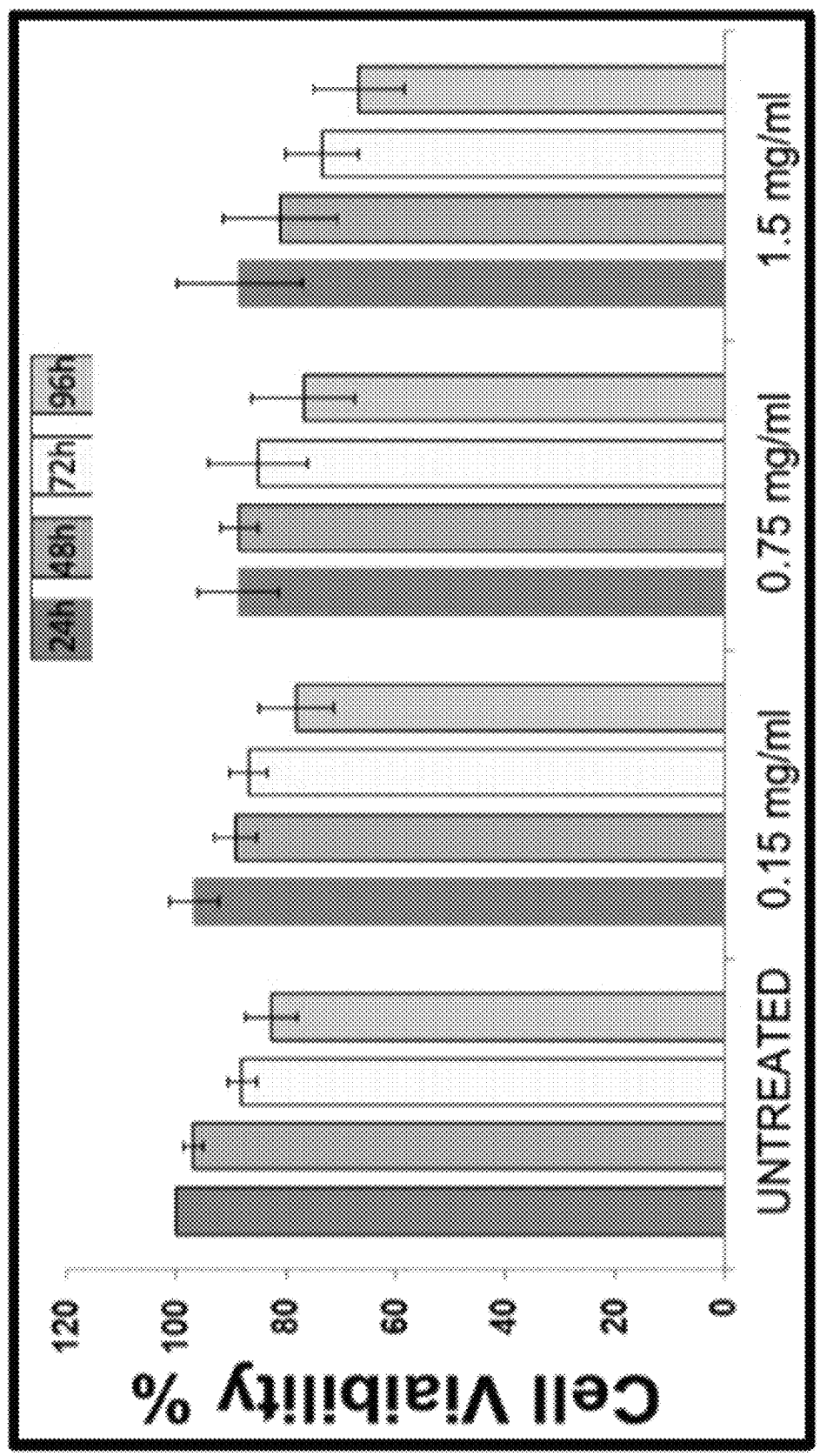
FIG. 28A depicts the cell viability of encapsulated spheroids using a CellTiter-Glo assay, in accordance with the present disclosure.
Figure 28B:
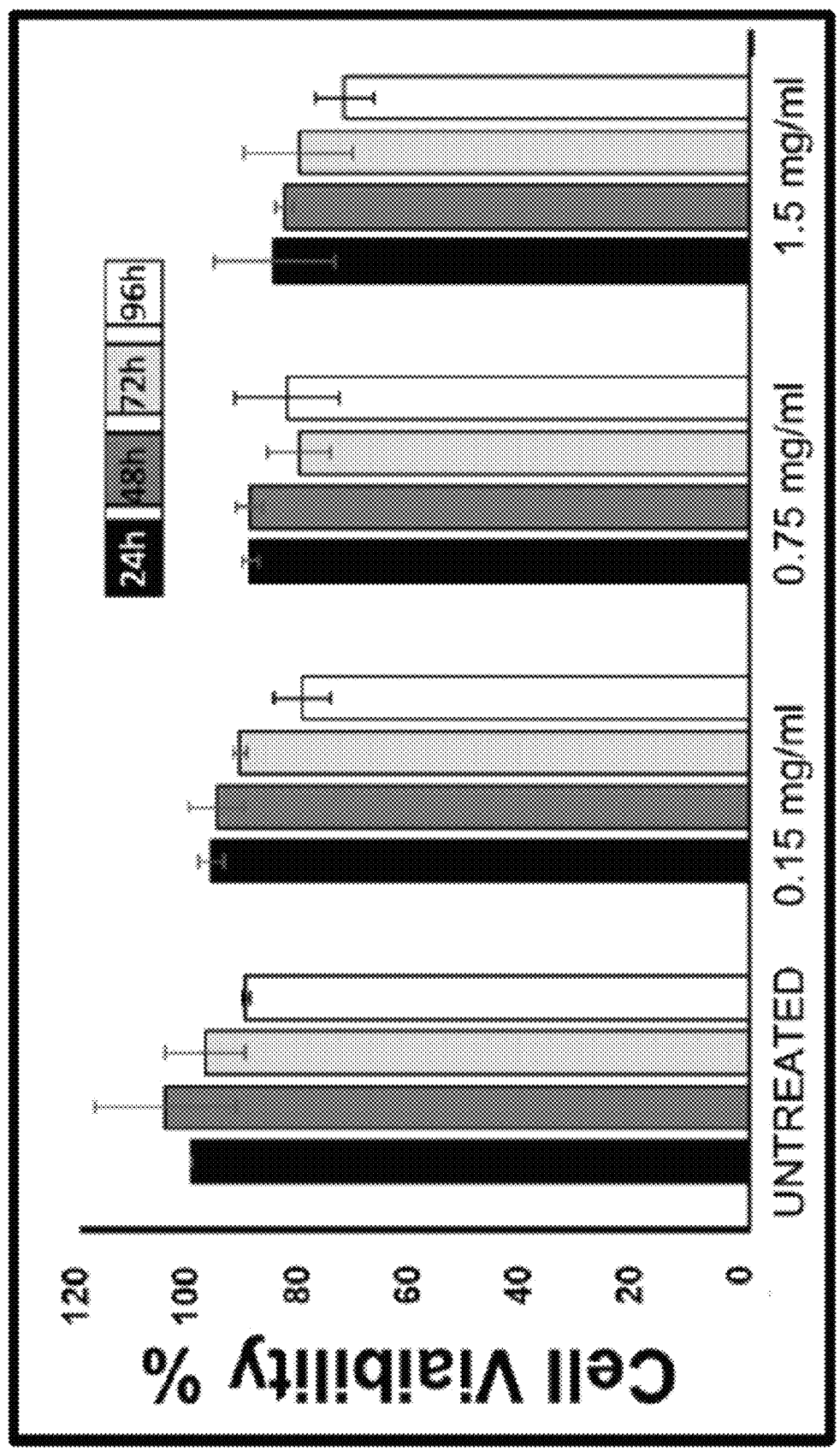
FIG. 28B depicts the cell viability of encapsulated spheroids using a CellTiter-Glo assay, in accordance with the present disclosure.

FIG. 28A depicts the cell viability of encapsulated spheroids using a CellTiter-Glo assay. Encapsulated spheroids with parental aminoglycoside antibiotic-derived hydrogel beads (0.75 mg/mL) demonstrated approximately 85% cell viability after 72 hours. FIG. 28B depicts the cell viability of encapsulated spheroids using a CellTiter-Glo assay. Encapsulated spheroids with quarternized aminoglycoside antibiotic-derived hydrogel beads (0.75 mg/mL) demonstrated approximately 80% cell viability after 72 hours.

Figure 29:
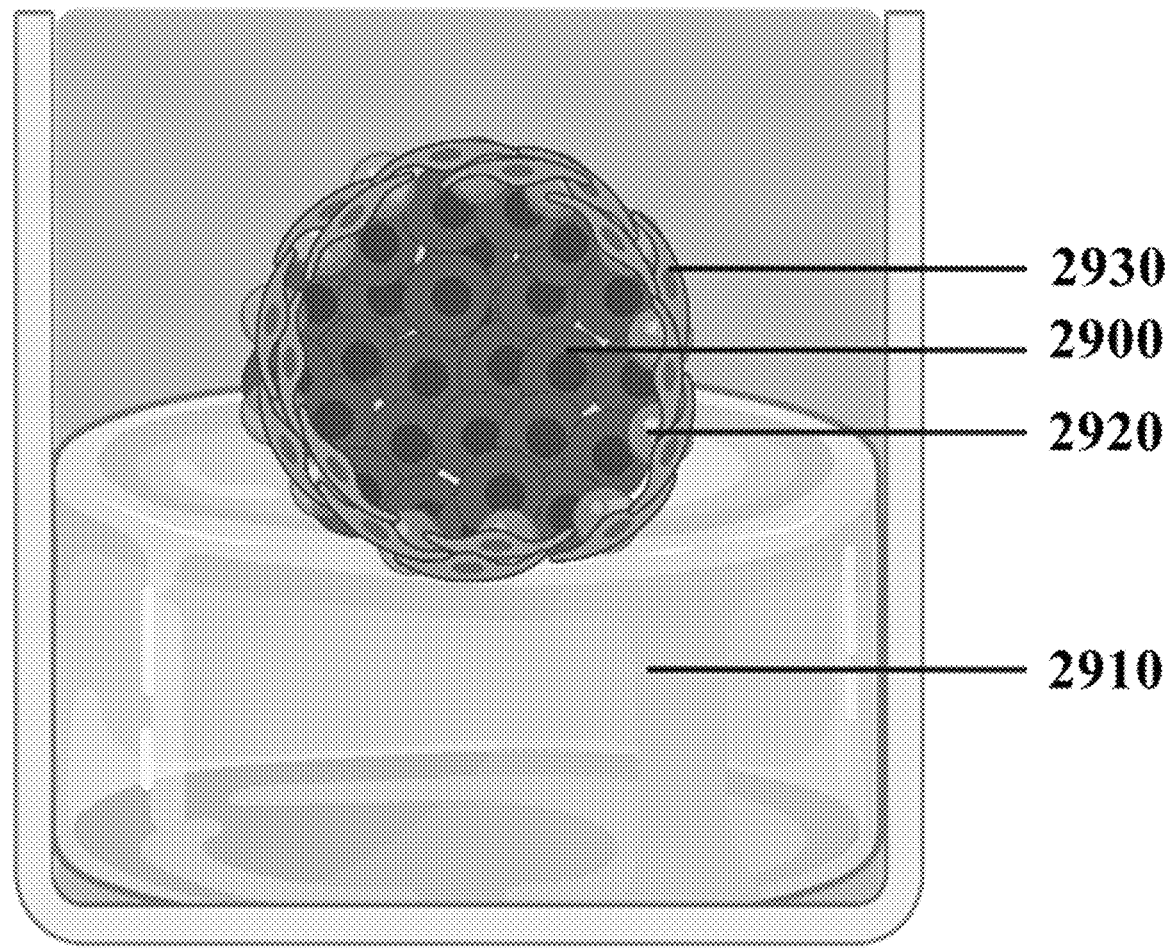
FIG. 29 illustrates an embodiment of a composition comprising an encapsulated spheroid wherein the encapsulated spheroid further comprises at least two layers of cells, in accordance with the present disclosure.

FIG. 29 illustrates an embodiment of a composition comprising an encapsulated spheroid wherein the encapsulated spheroid further comprises at least two layers of cells. The inner spheroid of cancer cells 2900 on an aminoglycoside antibiotic-derived hydrogel 2910 are encapsulated by aminoglycoside antibiotic-derived hydrogel beads 2920 and a second layer of immune cells 2930.

Figure 30:
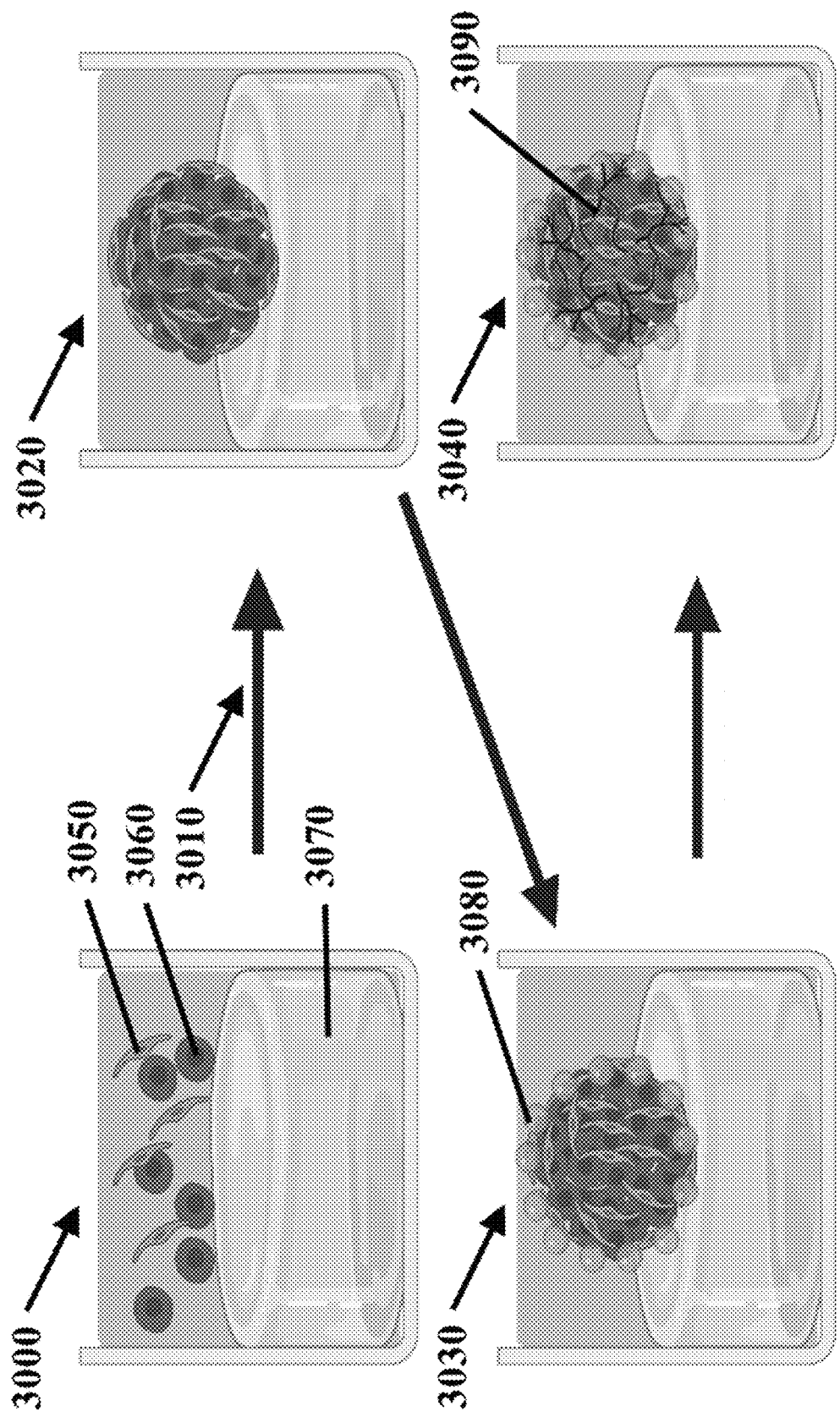
FIG. 30 illustrates an embodiment of a method of producing an encapsulated organoid comprising vascular endothelial growth factor (VEGF), in accordance with the present disclosure.

FIG. 30 illustrates an embodiment of a method of producing an encapsulated organoid comprising the bioactive agent vascular endothelial growth factor (VEGF). Endothelial cells 3050 and stem cells 3060 are seeded 3000 on an aminoglycoside antibiotic-derived hydrogel 3070 and incubated 3010 at 37° C. and 5% CO2 to form a spheroid 3020. VEGF loaded aminoglycoside antibiotic-derived hydrogel beads 3080 are added 3030 to the spheroid and centrifuged at 100 RPM for 20 minutes. The encapsulated spheroid with VEGF loaded aminoglycoside antibiotic-derived hydrogel beads is cultured to allow for endothelialization and vasculature 3090 formation 3040.

Figure 31:
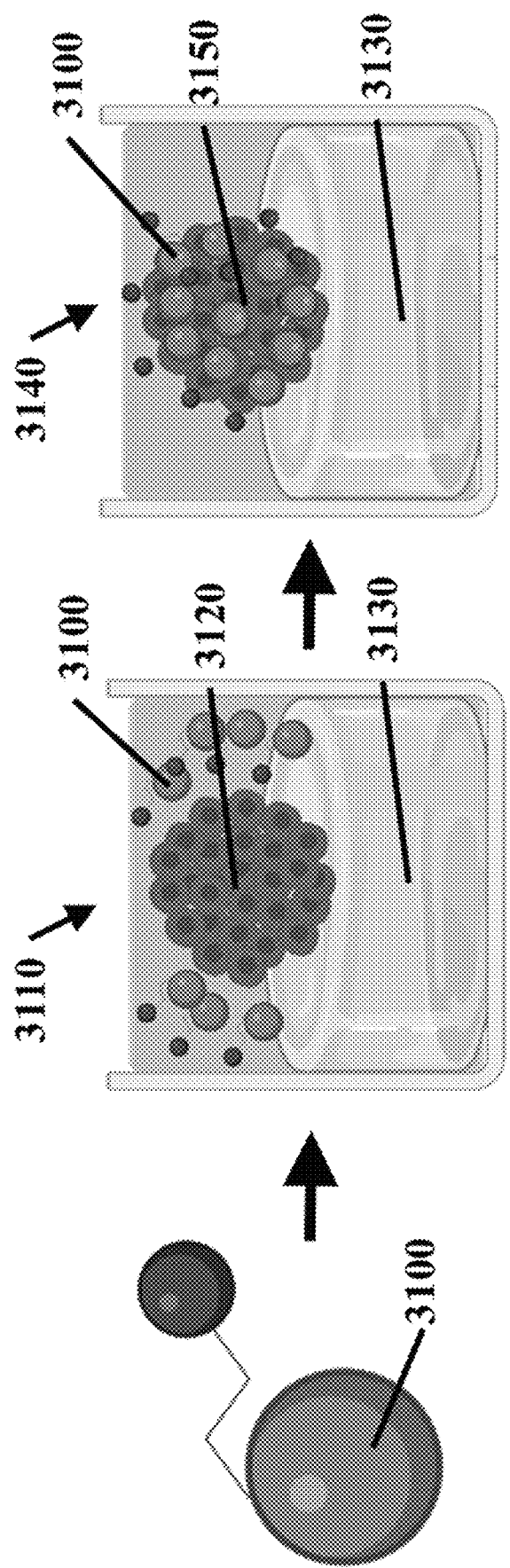
FIG. 31 illustrates an embodiment of a method of using aminoglycoside antibiotic-derived hydrogel beads conjugated to magnetic particles, in accordance with the present disclosure.

FIG. 31 illustrates an embodiment of a method of using aminoglycoside antibiotic-derived hydrogel beads conjugated to magnetic particles. Aminoglycoside antibiotic-derived hydrogel beads are conjugated to magnetic particles 3100 and added 3110 to a spheroid 3120 cultured on a aminoglycoside antibiotic-derived hydrogel 3130. A magnetic source is applied 3140 to the solution comprising spheroids and aminoglycoside antibiotic-derived hydrogel beads conjugated to magnetic particles to form an encapsulated spheroid 3150.

EXAMPLES

Example 1: Aminoglycoside Antibiotic-Derived Hydrogel Synthesis

Aminoglycosides and aminoglycoside-derived materials have been used for molecular biology applications—DNA binding and delivery, but aminoglycoside antibiotic (amikacin) derived microbeads have recently come into light as a potential platform for regenerative medicine applications. Aminoglycoside antibiotic-derived hydrogel beads are positively charged microbeads in the size range of 9±4 gm. These microbeads display quaternary amine functionalities (quarternized aminoglycoside antibiotic-derived hydrogel beads) which increases their positive charge. It is hypothesized that the charge interactions between positively charged aminoglycoside antibiotic-derived hydrogel beads and negatively charged phospholipid bilayer in the cells could play a part in the robust encapsulation of spheroids with aminoglycoside antibiotic-derived hydrogel beads without addition of any chemicals (FIG. 2). Aminoglycoside antibiotic-derived hydrogel beads also consist of various groups that may be conjugated, which can be exploited for drug delivery and regenerative medicine applications (FIG. 3).

Aminoglycoside antibiotic-derived hydrogel was prepared through ring-opening polymerization between anime groups of amikacin hydrate (AH; Sigma Aldrich Inc., St. Louis, MO) and epoxide groups of poly(ethylene glycol) diglycidyl ether (PEGDE; Sigma Aldrich Inc., St. Louis, MO) (Alessandri, K. et al. "Cellular capsules as a tool for multicellular spheroid production and for investigating the mechanics of tumor progression in vitro," *Proc National Acad Sci* 110: 14843-14848 (2013), which is hereby incorporated by reference in its entirety). Monomer AH and cross-linker PEGDE were dissolved in Nanopure® water (NPW) in different stoichiometric ratios to obtain Aminoglycoside antibiotic-derived hydrogel of different compositions, named as AM1, AM2, AM3, AM4, AM5, AM6, and AM7 (Table 1). All the solutions were vortexed for a minute each until transparency was achieved to ensure complete dissolution of the components.

TABLE 1

Aminoglycoside antibiotic-derived hydrogel compositions used for spheroid generation
Aminoglycoside antibiotic-derived hydrogel Compositions

| Aminoglycoside antibiotic-derived hydrogel | Mole Ratio (AH: PEGDE) | NPW |
|---|---|---|
| AM1 | 1:1.5 | 100 mL |
| AM2 | 1:2 | 100 mL |
| AM3 | 1:2.7 | 100 mL |
| AM4 | 1:3 | 100 mL |
| AM5 | 1:4 | 100 mL |
| AM6 | 1:5 | 100 mL |
| AM7 | 1:6 | 100 mL |

Generation of Aminoglycoside Antibiotic-Derived Hydrogel Coated Cell Culture Plates Pre-gels (1 mL AM1-7) were filtered through a 0.20 µm filter and 40 µL of filtrate was added to each well of 96 well cell culture plates (polystyrene plates, Coming, NY; glass bottom plates for confocal microscopy, Cellvis, Mountain View, CA). The plates were sealed with Paraffin tape, and incubated in an oven maintained at 40° C. for 7.5 h. After gelation, the surface of aminoglycoside antibiotic-derived hydrogel coated wells were washed by adding 275 µL, NPW to each well and incubating at 37° C. for 12 h to treat traces of untreated monomers. The gel thickness was approximately 1 mm after gelation.

A similar protocol was followed for generation of aminoglycoside antibiotic-derived hydrogel coated 24 well cell culture plates. 400 µL of filtrate was added to each well instead of 40 µL, and monomer washing was performed by adding 2750 µL, of NPW to each well.

Results: The reaction of amines present in amikacin with epoxides present in PEGDE resulted in the formation of aminoglycoside antibiotic-derived hydrogel (FIG. 4A-4B). AM2-7 showed uniform layering on polystyrene cell culture plates, but AM1 coated plates illustrated lumps of gel, advocating the importance of PEGDE (cross-linker). They were henceforth not used for spheroid generation. Possibly due to the change in hydrophobicity, some cracks were observed sparsely among the wells of the glass-bottom plates coated with AM2-7, but majority of them were uniformly coated.

Cell Culture

T-47D breast cancer and A375 NRAS-mutant isogenic melanoma cell lines were obtained from the American Type Cell Culture (Manassas, VA). Normal bone marrow derived Human Mesenchymal Stem Cells (hMSCs) were obtained from Lonza (PT-2501). Both tumor and stem cells were cultured in Dulbecco's Modified Eagle's medium (DMEM) (Sigma, St. Louis, MO) supplemented with 10% v/v fetal bovine serum (FBS), 1% penicillin-streptomycin solution (Corning, Corning, NY) (10,000 units/mL), and 1% 100× GlutaMAX solution (gibco, Waltham, MA) at 37° C. in 5% carbon dioxide ($CO_2$) in an incubator. At approximately 80% confluence, cells were trypsinized using 0.25% trypsin-EDTA (Sigma, St. Louis, MO) and sub-cultured.

Generation of 3D Spheroids

T-47D and A375 cells were seeded at the densities of 30,000 to 100,000 cells per well in 96 well and 750,000 to 1000,000 cells per well in 24 well AM5 coated cell culture plates. hMSCs were seeded at the densities of 30,000 cells per well in 96 well AM1-7 coated cell culture plates to observe robust spheroid formation. The plates were sealed with Paraffin tape and incubated at 37° C. in 5% carbon dioxide ($CO_2$) in an incubator and allowed to form spheroids. Spheroids were formed overnight in case of tumor cells and in 48 hours in case of hMSCs following culture on aminoglycoside antibiotic-derived hydrogel.

Results: Appropriate concentrations of freshly sub-cultured cells were seeded on aminoglycoside antibiotic-derived hydrogel coated plates and incubated for 1-3 days (FIG. 5). T-47D breast cancer and A375 NRAS-mutant isogenic melanoma cells demonstrated negligible adhesion to the surface of AM5, but they attached and spread on AM2-4 coated cell culture plates. AM6 and AM7 yielded formation of fragile spheroids. On the other hand, human bone marrow derived MSCs appeared to demonstrate no adhesivity on AM6 and AM7; loosely spread cells on AM2-4 and a cluster of cells prone to breakage was indicated on AM5, as mentioned in Table 2 and illustrated in FIG. 6. Non-adhesivity on AM5, 6, and 7 coated plates was simultaneously engendered by lower amine and higher PEG contents. Formation of a single spheroid was observed in every well, likely facilitated by the high reported mechanical stiffness and non-adhesivity of the aminoglycoside antibiotic-derived hydrogel 1. The size of spheroids was modulating by seeding different cell numbers on aminoglycoside antibiotic-derived hydrogel (30,000/50,000/750,000/100,000 cells per well); the dimensions of spheroids, as approximated from confocal microscopy, could be tuned from 300 µm to 1200 µm by increasing cell density. Due to such ease of use of aminoglycoside antibiotic-derived hydrogel platform, it asserts dominance over other approaches of 3D cell culture involving rotating wall bioreactors, liquid overlay cultures, and hanging droplet cultures that are labor intensive and provide low throughput and a heterogenous population of spheroids.

TABLE 2

Spheroid formation on aminoglycoside antibiotic-derived hydrogel coated cell culture plates
Spheroid Formation
Uniform Aminoglycoside Antibiotic-Spheroid Formation Derived Hydrogel Coating

| Aminoglycoside Antibiotic-Derived Hydrogel | Polystyrene Plates | Glass Bottom Plates | T-47D and A375 | hMSCs |
|---|---|---|---|---|
| AM1 | No | No | No | No |
| AM2 | Yes | Sparse cracks | No | No |
| AM3 | Yes | Sparse cracks | No | No |
| AM4 | Yes | Sparse cracks | No | No |
| AM5 | Yes | Yes | Yes | No |
| AM6 | Yes | Yes | No | Yes |
| AM7 | Yes | Yes | No | Yes |

Preparation of Parental Aminoglycoside Antibiotic-Derived Hydrogel Beads

Emulsion polymerization method (Tokuyama, H. & Yazaki, N. "Preparation of poly(N-isopropylacrylamide) hydrogel beads by circulation polymerization," *React Funct Polym* 70: 967-971 (2010), which is hereby incorporated by reference in its entirety) was used to prepare parental aminoglycoside antibiotic-derived hydrogel beads (Grandhi, T. S. P. et al. "Aminoglycoside Antibiotic-Derived Anion-Exchange Microbeads for Plasmid DNA Binding and in Situ DNA Capture," *Acs Appl Mater Inter* 6: 18577-18589 (2014), which is hereby incorporated by reference in its entirety). A uniform mixture was generated by dissolving AH (100 mg, 0.17 mmol) in 1 mL of NPW followed by addition of PEGDE in a molar ratio of 1:2. The mixture was stirred at 100 revolutions per minute (RPM) and pre-gelled for 4 min at 70° C. After 4 min, it was collected in a syringe and dispensed slowly into a solution of mineral oil (Acros Organics, Pittsburgh, PA) and 1% (w/v) Span-80 (TCI America, Portland, OR) through BD Precision Glide 27G1 ¼ needle and 5 mL syringe (Becton, Dickinson and Company, Franklin Lakes, NJ). The mineral oil-surfactant solution was maintained at 65° C. throughout the process. Approximately 500 µL of the pre-gel solution was dispensed into the heated oil phase within 25 min under constant stirring at 260 RPM. The beads (parental aminoglycoside antibiotic-derived hydrogel beads) could gel for 10 min, followed by extensive washing and size measurements.

Parental aminoglycoside antibiotic-derived hydrogel beads were collected by centrifugation for 10 min at 5500 RPM. Oil was washed off their surface by using a solution of 1% (v/v) Tween 20 detergent. Following detergent washes, the beads were finally washed multiple times with NPW. The particle diameters of parental aminoglycoside antibiotic-derived hydrogel beads were measured using phase-contrast microscopy; 50 beads were chosen randomly from each batch and their diameters were recorded. The averaged bead diameter of these samples was used as an indicator of size in subsequent analyses.

Results: Here, the generation of amikacin derived microbeads for potential application in encapsulation of spheroids is illustrated (FIG. 7) The cross-linking of amines present in AH and epoxides in PEGDE resulted in the formation of aminoglycoside antibiotic-derived hydrogel. It has been reported that multiple amines in aminoglycoside antibiotic-derived hydrogel can be exploited for spheroid encapsulation in the form of microbeads. Parental aminoglycoside antibiotic-derived hydrogel beads were generated through emulsion polymerization with AH:PEGDE as 1:2. Based on reported literature the mixture was allowed to pre-gel for 4 min while stirring at 100 RPM at 70° C. The aminoglycoside antibiotic-derived hydrogel solution was then introduced to heated mineral oil phase at 65° C. while stirring at 260 RPM supplemented with 1% Span-80 surfactant (w/v) in order to stabilize the water-in-oil microemulsion. Parental aminoglycoside antibiotic-derived hydrogel beads formed in mineral oil were separated from the oil phase by centrifugation at 5000 RPM for 10 min following which, the microbeads were extensively washed with NPW supplemented with 1% (v/v) Tween 20 to allow the removal of remaining Span-80 and mineral oil (FIG. 7).

Based on phase contrast images and previous reports, it has been observed that aminoglycoside antibiotic-derived hydrogel beads generated using the above emulsion system had spherical morphologies (FIG. 8) and average diameter varying from approximately 9 μm±4 μm.

Preparation of Quaternized Aminoglycoside Antibiotic-Derived Hydrogel Beads

Amines and hydroxyls present in parental aminoglycoside antibiotic-derived hydrogel beads were quaternized to form quaternized aminoglycoside antibiotic-derived hydrogel beads using the procedure reported by Grandhi el al. (Grandhi, T. S. P. et al. "Aminoglycoside Antibiotic-Derived Anion-Exchange Microbeads for Plasmid DNA Binding and in Situ DNA Capture," *Acs Appl Mater Inter* 6: 18577-18589 (2014), which is hereby incorporated by reference in its entirety). Glycidyl trimethylammonium chloride (GTMAC) was used in an aqueous solution with parental aminoglycoside antibiotic-derived hydrogel beads. Excess GTMAC was mixed with aminoglycoside antibiotic-derived hydrogel beads at 200 RPM in NPW for 24 h at 70° C. followed by extensive washing (Grugkiene, et al., "Quaternization of chitosan and partial destruction of the quaternized derivatives making them suitable for electrospinning," *Chemija* 24: 325-334 (2013). The resulting solution was termed as quaternized aminoglycoside antibiotic-derived hydrogel beads.

Results: To use aminoglycoside antibiotic-derived hydrogel beads in loading of bioactive compounds for delivery to spheroids, it is critical that accessible amine moieties which allow for subsequent conjugation chemistries be present. The reaction of 100 μL, ninhydrin reagent with a 0.5 mm parental aminoglycoside antibiotic-derived hydrogel beads model at 70° C. for 10 min resulted in the generation of a bluish-purple colored product, which is an evidence of the presence of reactive primary and secondary amines. Quaternization of these reactive amines during generation of quaternized aminoglycoside antibiotic-derived hydrogel beads was confirmed by the lack of demonstration of a bluish-purple product, unlike the unmodified parental aminoglycoside antibiotic-derived hydrogel beads.

Ninhydrin Assay

Quaternization was qualitatively confirmed in quaternized aminoglycoside antibiotic-derived hydrogel beads solution using the ninhydrin assay (Potta, T. et al. "Discovery of antibiotics-derived polymers for gene delivery using combinatorial synthesis and cheminformatics modeling," *Biomaterials* 35: 1977-1988 (2014), which is hereby incorporated by reference in its entirety). Commercially available ninhydrin reagent (200 μL) was added to 1 mg of parental and quaternized aminoglycoside antibiotic-derived hydrogel beads and incubated at 99° C. for 10 min, and the color change was visually observed and recorded.

Encapsulation of Spheroids 10 mg/mL stock concentrations of parental aminoglycoside antibiotic-derived hydrogel beads and quaternized aminoglycoside antibiotic-derived hydrogel beads were prepared using the methods detailed above. Next, six serial dilutions—2×, 5×, 10×, 20×, 50×, and 100× were prepared in NPW. After robust spheroid formation, 100 media was slowly removed from the wells containing the spheroids. The spheroids were visualized under the microscope to ensure there was no breakage. 100 μL of each dilution of either parental aminoglycoside antibiotic-derived hydrogel beads or quaternized aminoglycoside antibiotic-derived hydrogel beads was added to the wells. The cell culture plates were then slow centrifuged at 100 RPM for a period of 15 min to accelerate the interactions between aminoglycoside antibiotic-derived hydrogel beads and spheroids. Post washing three times with 1×PBS to remove stray aminoglycoside antibiotic-derived hydrogel beads, the spheroids were imaged with phase-contrast to visualize the encapsulating layer.

Results: Encapsulated 3D models could be substantially beneficial in regenerative medicine through delivery of bioactive compounds and drugs to the spheroids and investigating their effects. Thus, efforts were focused on ensuring a complete encapsulation of the top- and bottom surfaces, along with the edges of the spheroid with the aminoglycoside antibiotic-derived hydrogel beads. Initially, it was hypothesized that the spheroid encapsulation could take place through charge interactions between positively charged aminoglycoside antibiotic-derived hydrogel beads and negatively charged phospholipid bilayer of cells if the aminoglycoside antibiotic-derived hydrogel beads coated plates were allowed to incubate for a long duration of time at 37° C. (FIG. 9). Corresponding volumes of the parental aminoglycoside antibiotic-derived hydrogel beads dilutions were added to wells containing the spheroids and phase contrast images were captured at different intervals under EVOS FL Auto Live Cell Imaging Inverted Microscope System, as described previously (FIG. 10). The images demonstrated that using this technique, encapsulation could only be observed after a period of 48 h. It was also noticed that the encapsulated regions were directly proportional to the concentration of aminoglycoside antibiotic-derived hydrogel beads solution. Amikacin has four primary amines, one secondary amine, and eight hydroxyl groups. As reported before, quaternization of amine groups can help increase the positive charge content in aminoglycoside antibiotic-derived hydrogel beads –Q44 that was performed using GTMAC; the amines of amikacin react with the epoxide group of GTMAC at neutral or acidic pH as an addition reaction. As a result of this, a more uniform spheroid encapsulation was anticipated.

As expected, quaternized aminoglycoside antibiotic-derived hydrogel beads formed a ring like layer around the T-47D spheroids within 24 hours of incubation and the size and density of the outer ring expanded with an increase in quaternized aminoglycoside antibiotic-derived hydrogel bead concentration. The encapsulated spheroids were also captured in phase-contrast at a higher resolution to visualize the regions between spheroids and aminoglycoside antibiotic-derived hydrogel beads (FIG. 11). 2D structure image of CID 37768 (amikacin) reproduced from National Center for Biotechnology Information (2020). PubChem Compound Summary for CID 37768, Amikacin Retrieved Oct. 15, 2020 from https://pubchem.ncbi.nlm.nih.gov/compound/Amikacin. (No special permissions required). The images strengthened the position that quaternized aminoglycoside antibiotic-derived hydrogel beads could provide a superior encapsulation with a potential application in delivery of bioactive compounds to the spheroids. Based on this evidence, quarternized aminoglycoside antibiotic-derived hydrogel beads were used for rest of the studies (hen. Bright field images of encapsulated spheroids using 20× objective proffered a definite region of separation between spheroids and aminoglycoside antibiotic-derived hydrogel beads, the interspersed region, as shown in FIG. 12. This approach, although successful, was of labor and time intensive nature. Multiple artificial means have been utilized to accelerate the encapsulation of spheroids, such as microfluidic devices, emulsion droplets, 3D printing, alginate or hydrogel biomaterials, but they come with roadblocks such as disintegration of spheroid and low encapsulated cell viability.

Owing to the challenges posed by the previously mentioned and existing encapsulation techniques, low speed centrifugation of cell culture plates containing spheroids after addition of aminoglycoside antibiotic-derived hydrogel beads was tested for encapsulation efficiency. Centrifugation at lower RPMs (100-1000 RPM) for a longer duration of time has been successfully employed to enhance the transfection rate in suspension cell cultures. After several trial runs, the optimum RPM and centrifugation time that could lead to adequate encapsulation were identified. The integrity of spheroids was confirmed using bright field microscopy. Centrifuging the plate at 100 RPM for 15 minutes after addition of aminoglycoside antibiotic-derived hydrogel beads demonstrated optimum encapsulation, as illustrated in FIG. 13.

Conjugation of Aminoglycoside Antibiotic-Derived Hydrogel Beads with Rhodamine B Aminoglycoside antibiotic-derived hydrogel beads were conjugated with Rhodamine B (Rho-conjugated aminoglycoside antibiotic-derived hydrogel beads) containing carboxylic acid groups using COMU ((1-Cyano-2-ethoxy-2oxoethylidenaminooxy) dimethylamino-morpholino-carbenium hexafluorophosphate) catalyzed aqueous-phase reaction. Approximately 40 mg of aminoglycoside antibiotic-derived hydrogel beads were dispersed in 5 mL of NPW. In this aqueous solution, 500 µL of 5 wt % TPGS-750-M (DL-a-Tocopherol methoxypolyethylene glycol succinate solution) and 100 µL of 2,6-Lutidine was added to activate the conjugation reaction. Afterwards, 580 µL of 1 mM Rhodamine-B was added into the reaction mixture along with 150 mg of COMU, the coupling reagent. Reaction mixture was stirred at room temperature for 12 hours, following which the Rho-conjugated aminoglycoside antibiotic-derived hydrogel beads were isolated by centrifuging the solution. They were further washed thrice with NPW to remove unreacted chemicals and further used for encapsulating the spheroids.

Conjugation of Aminoglycoside Antibiotic-Derived Hydrogel Beads with Fluorescein Aminoglycoside antibiotic-derived hydrogel beads were also conjugated with Fluorescein (also containing carboxylic acid groups) using EDC (N-(3-Dimethylaminopropyl)-N'-ethylcarbodiimide hydrochloride) and NHS (N-Hydroxysuccinimide)-catalyzed aqueous-phase reaction. Approximately 40 mg of aminoglycoside antibiotic-derived hydrogel beads were dispersed in 5 mL of water. 130 mg of EDC and 80 mg of NHS were added to this aqueous solution and it was stirred for 1 hour at room temperature. 400 µL of 1 mM Fluorescein was added into the reaction mixture and it was stirred at room temperature for 24 hours. Fluorescein-conjugated beads were isolated by centrifuging the solution and further washed thrice with NPW to remove unreacted chemicals and further used for encapsulating the spheroids.

Results: Fluorescein-conjugated aminoglycoside antibiotic-derived hydrogel beads: To avoid the overlap of red fluorescing signal from Rho-conjugated aminoglycoside antibiotic-derived hydrogel beads and red spheroid stains (such as DRAQ5TM), aminoglycoside antibiotic-derived hydrogel beads were also conjugated with Fluorescein, an organic green fluorescing tracer dye for contrast (FIG. 14).

Encapsulation of Spheroids in Rho-Conjugated Aminoglycoside Antibiotic-Derived Hydrogel Beads 10 mg/mL stock solutions of Rho-conjugated parental aminoglycoside antibiotic-derived hydrogel beads and quarternized aminoglycoside antibiotic-derived hydrogel beads were prepared using the methods described above. Using these, three working solutions designated as Low (0.15 mg/mL), Medium (0.75 mg/mL), and High (1.5 mg/mL) of both parental aminoglycoside antibiotic-derived hydrogel beads and quarternized aminoglycoside antibiotic-derived hydrogel beads were prepared in DMEM and tested for encapsulation (Table 3).

Results: Rho-conjugated aminoglycoside antibiotic-derived hydrogel beads: After achieving optimum encapsulation, aminoglycoside antibiotic-derived hydrogel beads were conjugated with Rhodamine, a red fluorescing tracer dye to visualize the encapsulation through fluorescence and confocal microscopy, as demonstrated in (FIG. 14). Spheroids were generated using different initial cell densities and encapsulated with Rho-conjugated aminoglycoside antibiotic-derived hydrogel beads, as discussed previously.

TABLE 3

Rho-conjugated parental aminoglycoside antibiotic-derived hydrogel beads and quarternized aminoglycoside antibiotic-derived hydrogel beads working solutions used for spheroid encapsulation Rho-conjugated Aminoglycoside Antibiotic-Derived Hydrogel Beads Solutions

| Stock Solution | Working Solutions |
|---|---|
| Parental aminoglycoside antibiotic-derived hydrogel beads (10 mg/mL) | Low (0.15 mg/mL) |
|  | Medium (0.75 mg/mL) |
|  | High (1.5 mg/mL) |
| Quarternized aminoglycoside antibiotic-derived hydrogel beads (10 mg/mL) | Low (0.15 mg/mL) |
|  | Medium (0.75 mg/mL) |
|  | High (1.5 mg/mL) |

As described above, the spheroids were encapsulated in the above-mentioned working solutions of Rho-conjugated aminoglycoside antibiotic-derived hydrogel beads. Before centrifugation, the corresponding volume of fluorescent label for staining the spheroid as mentioned above was also added for contrast. The resulting encapsulated spheroids were termed as Rho-conjugated aminoglycoside antibiotic-derived hydrogel beads encapsulated spheroids.

Encapsulation of Spheroids in Fluorescein-Conjugated Aminoglycoside Antibiotic-Derived Hydrogel Beads 10 mg/ml stock solutions of Fluorescein-conjugated parental aminoglycoside antibiotic-derived hydrogel beads and quarternized aminoglycoside antibiotic-derived hydrogel beads were prepared using the methods described above. Using these, six working solutions of both parental aminoglycoside antibiotic-derived hydrogel beads and quarternized aminoglycoside antibiotic-derived hydrogel beads prepared in DMEM were tested for encapsulation (Table 4).

TABLE 4

Fluorescein-conjugated parental aminoglycoside
antibiotic-derived hydrogel beads and quarternized aminoglycoside
antibiotic-derived hydrogel beads working solutions used for
spheroid encapsulation
Fluorescein-conjugated Aminoglycoside
Antibiotic-Derived Hydrogel Beads Solutions

| Stock Solution | Working Solutions |
| --- | --- |
| Parental aminoglycoside antibiotic-derived hydrogel beads(10 mg/mL) | 2× (5 mg/mL) |
| | 5× (2 mg/mL |
| | 10× (1 mg/mL) |
| | 20× (0.5 mg/mL) |
| | 50× (0.2 mg/mL) |
| | 100× (0.1 mg/mL) |
| Quarternized aminoglycoside antibiotic-derived hydrogel beads (10 mg/mL) | 2× (5 mg/mL) |
| | 5× (2 mg/mL |
| | 10× (1 mg/mL) |
| | 20× (0.5 mg/mL) |
| | 50× (0.2 mg/mL) |
| | 100× (0.1 mg/mL) |

As described above, the spheroids were fluorescent labeled and encapsulated in the abovementioned working solutions of Fluorescein-conjugated aminoglycoside antibiotic-derived hydrogel beads. The resulting encapsulated spheroids were termed as Rho-conjugated aminoglycoside antibiotic-derived hydrogel beads encapsulated spheroids.

Fluorescence Intensity Optimization

The concentration of Fluorescein-conjugated aminoglycoside antibiotic-derived hydrogel beads used for encapsulation was optimized by preparing serial dilutions of aminoglycoside antibiotic-derived hydrogel beads stock solution in DMEM. The fluorescence intensity of serial dilutions was measured using a fluorometric plate reader and plotted against the concentrations.

All concentrations were then used to encapsulate the spheroids and observed through confocal microscopy, as mentioned above, to choose the optimum intensity. The corresponding concentration of Fluorescein-conjugated aminoglycoside antibiotic-derived hydrogel beads solution was used for further encapsulation studies.

Results: An investigation of the preliminary visualization studies on Fluorescein-conjugated aminoglycoside antibiotic-derived hydrogel beads revealed the high fluorescence intensity shown by the label, leading to a poor image quality and difficulty in differentiating between encapsulated layer and spheroid. To terminate this issue, aminoglycoside antibiotic-derived hydrogel beads were conjugated with two different concentrations of Fluorescein (namely, high and low) and six serial dilutions of each stock solution (10 mg/mL) were made—2×, 5×, 10×, 20×, 50×, 100×—in DMEM. The fluorescence intensity of each dilution was measured (Table 5) using a plate reader and plotted against the respective concentration (FIGS. 15A and 15B). Confocal images of each serial dilution at 0.75 zoom using a 10×. Objective lens pointed towards the concentration of 0.1 mg/mL or 100× dilution to display the optimum intensity to differentiation between each aminoglycoside antibiotic-derived hydrogel beads on different focal planes (FIG. 15C). Further encapsulation experiments with Fluorescein-conjugated aminoglycoside antibiotic-derived hydrogel beads were performed after ensuring the fluorescence intensity of the solution to be 248 arbitrary units (a.u.) using a plate reader.

TABLE 5

Fluorescence Intensity of each serial dilution of Fluorescein-conjugated aminoglycoside antibiotic-derived hydrogel beads
Fluorescence Intensity

| | Fluorescence Intensity (a.u.) | |
| --- | --- | --- |
| Concentration | Low | High |
| 2× (5 mg/mL) | 6268 | 10252 |
| 5× (2 mg/mL | 2297 | 3878 |
| 10× (1 mg/mL) | 1142 | 1705 |
| 20× (0.5 mg/mL) | 705 | 1165 |
| 50× (0.2 mg/mL) | 357 | 347 |
| 100× (0.1 mg/mL) | 248 | 373 |

Fluorescence Labeling of Spheroids

Five fluorescent dyes were used to label spheroids to provide contrast for confocal microscopy as detailed in Table 6.

TABLE 6

Fluorescent labels used to stain spheroids
Spheroid Stains

| Stain | Role | Working Concentration, Volume Used | Maximum $\lambda$absorption | Maximum $\lambda$emission |
| --- | --- | --- | --- | --- |
| 4',6-diamidino-2-phenylindole (DAPI) | Fluorescent stain binding to the adenine-thymine-rich regions of DNA | 1 pg/mL prepared in 1× PBS, 5 µL/well | 358 nm | 461 nm |
| Hoechst 33342 (Thermo Scientific™, Waltham, MA) | Cell permeant nuclear counterstain emitting blue fluorescence | 1 mg/mL in 1× PBS, 0.5 µL/well | 352 nm | 454 nm |
| DRAQ5™ (AATA Bioquest, Inc., Sunnyvale, CA) | far-red emitting anthraquinone compound staining nuclei in live cells | 10 µM prepared in 1× PBS, 50 µL/well | 598/646 nm | 681/697 nm |
| CytoTrace™ CMTPX Bioquest, Inc., Sunnyvale, CA | Red fluorescent cell-permeable dye for tracing cells | 2 µM prepared in (AAT DMSO, 0.5 µL/well | 577 nm | 602 nm |
| Concanavalin A (ConA) CF Inc., Fremont, CA | cell surface stain for mammalian cells Dye (Biotium, sterile NPW | 50 µg/mL prepared in | 593 nm | 614 nm |

The corresponding volume of fluorescent dyes was added along with the aminoglycoside antibiotic-derived hydrogel beads solution before centrifugation to allow optimal spheroid labeling, as mentioned in the sections above.

Phase Contrast Microscopy

The encapsulated spheroids were visualized under EVOS FL Auto Live Cell Imaging Inverted Microscope System (Advanced Light Microscopy Core—Regenerative Medicine and Bioimaging Facility, Arizona State University Core Facilities) to capture phase contrast images. 96 well polystyrene cell culture plates containing encapsulated spheroids were observed using 4× objective lens.

Laser Scanning Confocal Microscopy

The encapsulated spheroids used for confocal microscopy were generated on glass-bottom 96 well cell culture plates and imaged under Leica TCS SP8 White Light Laser Scanning Confocal with Light Sheet Microscope (Advanced Light Microscopy Core—Regenerative Medicine and Bioimaging Facility, Arizona State University Core Facilities). The microscope is equipped with white light tunable laser as well as an Argon 488 nm and 405 nm lasers. The system also has a combination of PMT and HyD GaAsP detectors as well as a DIC bright field detector. The fluorescent labels on aminoglycoside antibiotic-derived hydrogel beads and spheroids provided the contrast, and the images were captured using a 10× objective lens and a compilation of 30-40 sections of 5 µM each were used to reconstruct the 3D z-stack of the encapsulated spheroid.

Confocal Microscopy with Dipping Lens

The encapsulated spheroids were washed thrice with 1×PBS to remove stray aminoglycoside antibiotic-derived hydrogel beads and fixed using 10% neutral buffered formalin (NBF) overnight. The pointy end of 200 µL autopipette tip was chopped and used to remove encapsulated spheroids out of wells. They were suspended in 60 mm polystyrene petri dishes (Fisher Scientific, Hampton, NH) containing 1×PBS. The suspended spheroids were imaged using the Leica SP5 AcoustoOptical Beam Splitter Spectral Confocal Microscope (Advanced Light Microscopy Core—Regenerative Medicine and Bioimaging Facility, Arizona State University Core Facilities). A 10× high numerical aperture dipping objective with an access angle of 41° and a free working distance of 2.5 mm was employed to capture images.

Generation of Formalin Fixed Paraffin Embedded Spheroids (FFPE)

Encapsulated spheroids fixed overnight in 10% NBF were removed from the wells and added to a 1.5 mL Microcentrifuge Tube (MCT; 3 spheroids in each). Following that, 250 µL 2% low melting point agarose (1131 Scientific, Dubuque, IA) was added and allowed to gel at room temperature. The agarose-embedded encapsulated spheroids (hereafter, tissues) were scooped out using a plastic spatula and added to scintillation vials containing 1×PBS for 30 minutes for washing.

Dehydration. Before embedding, all the water from the tissues was removed to allow infiltration of paraffin. The tissues were dehydrated by exposing them to a series of alcohol solutions mentioned in Table 7 with gentle agitation at room temperature (RT).

Clearing. Due to immiscibility of paraffin in alcohols, the alcohol from tissue was cleared using xylene with gentle agitation at RT as reported in Table 8.

TABLE 7

Solutions used for tissue dehydration
Tissue Dehydration

| Solution | Time |
| --- | --- |
| 1X PBS | 30 minutes |
| 20% Ethanol | 30 minutes |
| 40% Ethanol | 30 minutes |
| 60% Ethanol | Overnight |
| 90% Ethanol | 30 minutes |
| 100% Ethanol | 30 minutes |
| 100% Ethanol | 30 minutes |

TABLE 8

Solutions used for tissue clearing
Tissue Clearing

| Solution | Time |
| --- | --- |
| 100% Xylene | 30 minutes |
| 100% Xylene | 30 minutes |

Paraffin Infiltration. Following adequate fixation, dehydration, and clearing, paraffin infiltration was performed with the solutions reported in Table 9.

Paraffin Embedding and Sectioning. The infiltrated tissue block was then placed in a cassette in the correct orientation and surrounded by a coat of paraffin using the Leica EG1160 Paraffin Embedding Station. The paraffin casing was solidified by placing on ice. After it was firm enough, the tissue block was placed into the block holder and sectioned into 5 µm sections (approximate thickness of each cell) using Leica RM165 Rotary Microtome. Consecutive thin sections (ribbons) were placed into a warm water bath to smooth out wrinkles. The chosen sections were scooped using positively charged microscopic slides (Hareta, Durham, NC) so that they stick to the slide.

TABLE 9

Solutions used for paraffin infiltration
Paraffin Infiltration

| Solution | Time | Temperature |
| --- | --- | --- |
| 1:1 Xylene:Paraffin | 60 minutes | 65° C. |
| Paraffin | 60 minutes | 65° C. |
| Paraffin | 60 minutes | 65° C. |

Hematoxylin and Eosin (H&E) Staining

Hematoxylin (Gill No. 3, Millipore Sigma, Burlington, MA) was used as a progressive stain for illustrating nuclear detail in the spheroids in a blue-purple color. Eosin was used as a counterstain to label the positively charged aminoglycoside antibiotic-derived hydrogel beads in a shade of pink. The slides containing freshly sliced samples were placed in a 60° C. incubator oven to help desiccate the sections and to enhance adherence of the sections to the slide. The slides were H&E stained.

Cell Viability Assay

CellTiter-Glo® 3D Cell Viability Assay was conducted to determine the number of viable cells in 3D cell culture based on quantitation of the ATP present, which is a marker for the presence of metabolically active cells after encapsulation of spheroids with parental aminoglycoside antibiotic-derived hydrogel beads and quarternized aminoglycoside antibiotic-derived hydrogel beads at four different time points (24, 48, 72, 96 h). according to the manufacturer's protocols, 150 µL assay reagent per 96 well glass-bottom cell culture plate (equal to the existing well volume) containing encapsulated spheroids was added and the plate was incubated. It was then manually shaken vigorously for 5 minutes to induce cell lysis and effectively extract ATP from the encapsulated spheroids. After allowing incubation at RT for 25 min to stabilize the signal, the luminescence was tested using a plate reader using an integration time of 0.25-1 sec per well. Wells containing only spheroids and only aminoglycoside antibiotic-derived hydrogel beads were used as controls to ascertain absence of any background luminescence.

Results: Toxicity studies using CellTiter-Glo assay were carried out to test the viability of cells in the A375 spheroid following encapsulation with aminoglycoside antibiotic-derived hydrogel beads. The outcomes indicated—85% cell viability in the spheroids encapsulated with parental aminoglycoside antibiotic-derived hydrogel beads and—80% cell viability in the spheroids encapsulated with quarternized aminoglycoside antibiotic-derived hydrogel beads at 72 hours at an identical concentration of 0.75 mg/mL of the aminoglycoside antibiotic-derived hydrogel beads, as demonstrated in FIG. 28. Further studies with Flow Cytometry to analyze the cell cycle were performed to confirm the cell viability post encapsulation.

Flow Cytometry

Flow cytometry preparation required the transfer and subsequent dissociation of three identical encapsulated spheroids into a single MCT and centrifugation at 1000 RPM at 25° C. for 10 min. Majority of the supernatant was removed (−90%) and the cell pellet was resuspended in either 200 mL of 1×PBS for control conditions or a mixture of 1×PBS:Triton X:Propidium Iodide at a ratio of 10:1:1 (v/v/v) for treatment conditions. The tubes were placed on ice or a cold rack that had been pre-frozen to −20° C. until flow cytometry data was collected. Flow cytometry were run by the Flow Core Staff on BD FACSAria IIu Cell Sorter housed in the Flow Cytometry Facility (Arizona State University Core Facilities).

Results: Currently, the cell viability analysis of 3D fluorescence stained spheroids relies on cytotoxicity assays, such as described above, but they are often unreliable due to the morphological change within the spheroids. Techniques like microscopy were time consuming and provided low throughput. Therefore, to analyze the behaviors of cells in the spheroids and provide accurate statistical information about individual cells, cell cycle analysis was performed using flow cytometry. This technique has high-speed and throughput capabilities and therefore, has garnered popularity to study characteristics of single cells as they flow in a fluid stream through a beam of light. 70

A375 models were dissociated along with aminoglycoside antibiotic-derived hydrogel beads only and aminoglycoside antibiotic-derived hydrogel beads+2D cells controls and stained with 1×PBS:Triton X:Propidium Iodide at a ratio of 10:1:1 (v/v/v). Cell cycle analysis was performed at appropriate parameters on FACSAria IIu Cell Sorter.

Example 2: Encapsulated Tumor Models

Fluorescence microscopy. Confocal fluorescence microscopy was employed to visualize the entrapment of spheroids generated on polystyrene 96 well cell culture plates in fluorescently labelled spheroids. As shown in FIG. 16, DAPI stained T-47D spheroids (initial cell density=30,000 cells/well,—1000 µm) portrayed visibly compact layers of Rho-conjugated aminoglycoside antibiotic-derived hydrogel beads of concentration 1.5 mg/mL, 0.75 mg/mL, 0.15 mg/mL around them when imaged using a 10× Objective on the EVOS FL Auto Live Cell Imaging Inverted Microscope System. A blue contrast from the spheroid was demonstrated with red from the aminoglycoside antibiotic-derived hydrogel beads. This study acted as one of the preliminary checkpoints of successful encapsulation of spheroids with aminoglycoside antibiotic-derived hydrogel beads.

Laser scanning confocal microscopy of DAPI-Rho models. Confocal z-stacks were acquired and analyzed to evaluate the total and positional fluorescent signal for T-47D spheroids (initial cell density=30,000 cells/well) generated on 96 well glass-bottomed plates labelled with DAPI and encapsulated with Rho-conjugated aminoglycoside antibiotic-derived hydrogel beads.

As demonstrated in FIG. 17, imaging was performed by capturing a series of horizontal scans through the spheroids using Leica Digital Light Sheet with a Hamamatsu Orca Flash 4.0 V2 CMOS camera, arranged as a vertical stack/z-stack by means of image analysis software (HyVo2 Deconvolution software—SVI Huygens integrated). Each optical section was acquired at 5 µm interval, with a typical imaging stack consisting of 30 to 40 optical sections per spheroid.

In recent years, the light sheet confocal microscopy in combination with 3D models has been commonly used to study morphologies. For the encapsulated T-47D spheroids, 3D reconstruction per stack was performed to visualize the encapsulation on different spots as illustrated in FIG. 18. Image size was 2048×2048 pixels. These projections were especially useful in visualizing the 3D microenvironment of the encapsulated spheroid (hereafter, model).

Laser scanning confocal microscopy of Hoechst-Rho models. A375 spheroids were generated using initial cell density of 30,000 cells/well and encapsulated in Rho-conjugated aminoglycoside antibiotic-derived hydrogel beads. The spheroids were then stained with Hoechst 33342 and visualized in the same way as mentioned above. Nuclear staining with 0.5 µL/well Hoechst demonstrated higher quality images than using DAPI and was used in further experiments (FIG. 19 and FIG. 20).

Laser scanning confocal microscopy of DRAQ5711-Fluorescein models. As discussed above, A375 spheroids were generated using initial cell density of 30,000 cells/well and encapsulated in Fluorescein-conjugated aminoglycoside antibiotic-derived hydrogel beads with concentration 0.1 mg/mL. The spheroids were then stained with DRAQ5TM and visualized using laser scanning confocal microscopy. The images demonstrated less contrast than the Hoechst-Rho model due to overlap of red fluorescence signal from the spheroids and the green fluorescence signal from the aminoglycoside antibiotic-derived hydrogel beads. Although, an overall encapsulation of the spheroid was verified, as demonstrated in FIG. 21.

Dipping lens confocal microscopy. To study full depth images of models, dipping lens confocal microscopy was performed using Leica SP5 AOBS Spectral Confocal microscope with a 200-degree field rotation and pixel resolution of up to 8000×8000, as shown in FIG. 22A. A375 spheroids with initial cell density of 30,000 cells/well encapsulated with Rho-conjugated aminoglycoside antibiotic-derived hydrogel beads were fixed with 10% NBF overnight. The fixed spheroids were removed from the wells and suspended in 1×PBS in a clear petri dish. The sample was placed on the stage and imaged using 10× objective dipping lens. The multi-dimensional image series were acquired and analyzed using Leica Confocal Software (LSC). The images captured through dipping lens aligned with those captured using confocal microscope in terms of a densely packed aminoglycoside antibiotic-derived hydrogel beads layer entirely encapsulating the spheroid. Vertical sectioning of the image also showed red streaks corresponding to the aminoglycoside antibiotic-derived hydrogel beads covering the spheroid surface, as demonstrated in FIG. 22.

Example 3: Visualization of Encapsulated hMSC Models

Laser scanning confocal microscopy of Hoechst-Rho models. Hoechst stained A375 spheroids revealed exceedingly high-quality images of the contrast between them and the aminoglycoside antibiotic-derived hydrogel beads layer. The same combination was tried with hMSC spheroids of initial cell density 30,000 cells/well cultured on AM6 and AM7 and encapsulated with 0.75 mg/mL (FIG. 23) and 0.15 mg/mL (FIG. 24) concentrations of Rho-conjugated aminoglycoside antibiotic-derived hydrogel beads. The images captured using 10× objective at 0.75 zoom demonstrated comprehensive coverage of the spheroid from bottom to top for both the concentrations. It was observed that encapsulation with 0.75 mg/mL aminoglycoside antibiotic-derived hydrogel beads solution exhibited a stronger red fluorescence signal and more spheroid coverage than with 0.15 mg/mL, which exhibited a more homogeneous wrapping of spheroid with the aminoglycoside antibiotic-derived hydrogel beads but a signal of comparatively lower intensity.

Laser scanning confocal microscopy of DRAQ5711-Fluorescein models. hMSC spheroids generated on AM6 and AM7 coated cell culture plates were stained with DRAQ5TM and encapsulated in 0.1 mg/mL Fluorescein-conjugated aminoglycoside antibiotic-derived hydrogel beads, followed by confocal microscopy using a 10× objective. Both spheroids showed identical encapsulation—a clear boundary visible between spheroid and aminoglycoside antibiotic-derived hydrogel beads layer, evidencing the compact packing of aminoglycoside antibiotic-derived hydrogel beads around the spheroids due to charge interactions. The overlap of fluorescent signals from aminoglycoside antibiotic-derived hydrogel beads encapsulating the bottom surface of the spheroid with the nuclear stain demonstrated an orange tinge in the middle, as illustrated in FIG. 24C.

30,000 cell spheroids. FFPE Rho-conjugated spheroids (initial cell density=30,000 cells/well, Rho-conjugated aminoglycoside antibiotic-derived hydrogel bead concentration=0.75 mg/mL) were generated followed by their sectioning and staining with H&E, using the protocol illustrated in FIG. 25.

H&E staining of FFPE spheroids showed presence of significant amounts of aminoglycoside antibiotic-derived hydrogel beads and cells, but no concrete spheroid was observed (FIG. 26). It is possible that the spheroids broke down due to sheer stress of transferring from wells to MCT or the addition of agarose and further washing steps. Nevertheless, the images captured using a 20× objective demonstrated clusters of cells with aminoglycoside antibiotic-derived hydrogel beads which indicate towards their presence in the tissue even after transferring multiple times and thus, attesting to the strong interactions between the aminoglycoside antibiotic-derived hydrogel beads and cell surface. The cells were stained purple (nuclear components stained by Hematoxylin) and the aminoglycoside antibiotic-derived hydrogel beads were stained pink due to positive charge (Eosin). Chunks of aminoglycoside antibiotic-derived hydrogel possibly removed while scooping out the spheroid were also observed to be stained pink with Eosin due to the positive charge on them.

100,000 cell spheroids. To overcome the challenge posed by breakdown of spheroids, A375 spheroids with initial cell density of 100,000 cells/well and approximate diameter of 1000 gm were generated and encapsulated with 0.75 mg/mL of Rho-conjugated aminoglycoside antibiotic-derived hydrogel beads. The fixed and dehydrated spheroids (tissues) were embedded with paraffin and sectioned. Serial sections of H&E stained tissues were imaged for comparison. An increase in the number of cells was distinctively seen in these sections, in the form of larger cell clusters, but as earlier, no definite boundary of spheroids or the aminoglycoside antibiotic-derived hydrogel beads layer was observed, as shown in FIG. 27.

106 cell spheroids generated on 24 well plates. To be able to visualize the spheroids clearly while scooping them out of the wells of the cell culture plate, A375 spheroids were then generated on 24-well polystyrene bottom cell culture plates. Initial cell density was 106 cells/well and plates were incubated for 48 hours to allow for robust spheroid formation. The spheroids demonstrated substantial frailty and broke down in the wells while transferring them from incubator to a sterile hood.

FIG. 6 is a representative image of spheroids comprising hMSCs cultured in 96-well cell culture plates coated with aminoglycoside antibiotic-derived hydrogels. hMSC cells were plated at an initial cell density of 30,000 cells per well. Each phase-contrast image is taken from a cell-culture plate coated with aminoglycoside antibiotic-derived hydrogels AM2 through AM7 after 3 days of incubation. AM2 through AM4 evidenced loosely spread cells and a cluster of cells was observed in AM5 which broke down when encapsulation studies were performed. AM6 and 7 demonstrated the formation of homogeneously packed spheroids (4× objective, scale bar—1000 μm).

Example 4: Multicellular Spheroid Formation

Spheroids encapsulated using aminoglycoside antibiotic-derived hydrogel beads can be further used for addition of further layers of different cell lines. A multilayered encapsulated spheroid (FIG. 29) will be formed with a layer of either fibroblast cells or immune cells around an encapsulated spheroid to study the effect these cells may have on the tumor cells and also to develop an in situ tumor microenvironment model which will help further understand response of the environment to drugs and the efficacy of the drugs in killing these cancer cells.

Example 5: Crosslinking Encapsulated Cells

Cross-linked encapsulated spheroids will be generated through use of crosslinkers like PEGDE to further strengthen the encapsulation of the spheroids by the aminoglycoside antibiotic-derived hydrogel beads (FIG. 30). Biocompatible crosslinkers such as PEGDE and BDDE (1,4-Butanediol diglycidyl ether) may be used.

Example 6: Delivery of Bioactive Agents

Aminoglycoside antibiotic-derived hydrogel beads will be loaded with bioactive agents. Bioactive agents may be selected from pharmaceutical compounds, growth factors, stem cell differentiation factors as well as other compounds or macromolecules. Aminoglycoside antibiotic-derived hydrogel beads loaded with bioactives may be used for a variety of functions ranging from killing cancer cells or for stem cell differentiation Example 7: Magnetic Aminoglycoside Antibiotic-Derived Hydrogel Beads Aminoglycoside antibiotic-derived hydrogel beads conjugated with magnetic particles will be developed to provide alternate methods of encapsulation (FIG. 31). Centrifugation based methods to encapsulate the spheroids can be used in situations where the a compact spheroid is desired. In methods using larger, more unstable spheroids that do not withstand the pressures of centrifugation, aminoglycoside antibiotic-derived hydrogel beads conjugated to magnetic particles can be used to facilitate spheroid formation. The beads can be pulled towards the spheroid through the use of magnetic well ring drives (Greiner Bio One).

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A composition comprising:
a spheroid comprising a plurality of cells; and
aminoglycoside antibiotic-derived hydrogel beads;
wherein the spheroid is encapsulated by the aminoglycoside antibiotic-derived hydrogel beads to form an encapsulated spheroid.

2. The composition of claim 1, wherein the plurality of cells comprises a plurality of cell types.

3. The composition of claim 1, wherein the spheroid comprises an organoid.

4. The composition of claim 3, wherein the organoid comprises vasculature, immune cells, or a combination thereof.

5. The composition of claim 1, wherein the plurality of cells are selected from the group consisting of mesenchymal stem cells, T-47D cells, A375 cells, and combinations thereof.

6. The composition of claim 1, wherein at least one of the aminoglycoside antibiotic-derived hydrogel beads is conjugated to an additional molecule.

7. The composition of claim 6, wherein the additional molecule is selected from the group consisting of a fluorescent protein, a magnetic particle, derivatives thereof, and combinations thereof.

8. The composition of claim 1, wherein a plurality of the aminoglycoside antibiotic-derived hydrogel beads are cross-linked.

9. The composition of claim 1, wherein the encapsulated spheroid further comprises a bioactive agent.

10. The composition of claim 9, wherein the bioactive agent is selected from the group consisting of vascular endothelial growth factor (VEGF), derivatives thereof, and combinations thereof.

11. The composition of claim 9, wherein the bioactive agent is encapsulated by the aminoglycoside antibiotic-derived hydrogel beads.

12. The composition of claim 9, wherein the bioactive agent is conjugated to at least one of the aminoglycoside antibiotic-derived hydrogel beads.

13. The composition of claim 1:
further comprising a second layer of cells;
wherein the second layer of cells at least partially encases the encapsulated spheroid.

14. A method comprising administering, to a subject in need thereof, an effective amount of the composition of claim 1.

15. The composition of claim 1, wherein:
the spheroid is configured to mimic a diseased tissue; and
the composition is configured to model a disease.

16. A method of creating an encapsulated spheroid, the method comprising:
coating a surface with an aminoglycoside antibiotic-derived hydrogel;
culturing a plurality of cells on the surface, thereby creating a spheroid comprising the plurality of cells; and
encapsulating the spheroid with a plurality of aminoglycoside antibiotic-derived hydrogel beads, thereby creating the encapsulated spheroid.

17. The method of claim 16, further comprising conjugating at least one of the aminoglycoside antibiotic-derived hydrogel beads with an additional molecule selected from the group consisting of a fluorescent protein, a magnetic particle, derivatives thereof, and combinations thereof.

18. A method comprising:
administering a compound to an encapsulated spheroid, wherein the encapsulated spheroid comprises:
a spheroid comprising a plurality of cells; and
aminoglycoside antibiotic-derived hydrogel beads;
wherein the spheroid is encapsulated by the aminoglycoside antibiotic-derived hydrogel beads to form the encapsulated spheroid; and
wherein the spheroid comprises an organoid.

* * * * *